(12) United States Patent
Schiltz et al.

(10) Patent No.: US 10,435,375 B2
(45) Date of Patent: Oct. 8, 2019

(54) CXCR4 CHEMOKINE RECEPTOR MODULATORS

(71) Applicant: NORTHWESTERN UNIVERSITY, Evanston, IL (US)

(72) Inventors: Gary E. Schiltz, Naperville, IL (US); Richard J. Miller, Chicago, IL (US); Rama K. Mishra, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/571,721

(22) PCT Filed: May 5, 2016

(86) PCT No.: PCT/US2016/030891
§ 371 (c)(1),
(2) Date: Nov. 3, 2017

(87) PCT Pub. No.: WO2016/179349
PCT Pub. Date: Nov. 10, 2016

(65) Prior Publication Data
US 2018/0155295 A1    Jun. 7, 2018

Related U.S. Application Data

(60) Provisional application No. 62/157,285, filed on May 5, 2015.

(51) Int. Cl.
| | | |
|---|---|---|
| C07D 231/56 | (2006.01) | |
| C07D 403/12 | (2006.01) | |
| C07D 401/14 | (2006.01) | |
| C07D 405/14 | (2006.01) | |
| C07D 401/04 | (2006.01) | |
| C07D 401/12 | (2006.01) | |
| C07D 403/06 | (2006.01) | |
| C07D 405/12 | (2006.01) | |
| C07D 417/14 | (2006.01) | |
| C07D 471/04 | (2006.01) | |
| C07D 401/06 | (2006.01) | |
| A61P 35/00 | (2006.01) | |

(52) U.S. Cl.
CPC ............ *C07D 231/56* (2013.01); *A61P 35/00* (2018.01); *C07D 401/04* (2013.01); *C07D 401/06* (2013.01); *C07D 401/12* (2013.01); *C07D 401/14* (2013.01); *C07D 403/06* (2013.01); *C07D 403/12* (2013.01); *C07D 405/12* (2013.01); *C07D 405/14* (2013.01); *C07D 417/14* (2013.01); *C07D 471/04* (2013.01)

(58) Field of Classification Search
CPC .. C07D 231/56; C07D 401/04; C07D 401/06; C07D 401/12; C07D 401/14; C07D 403/06; C07D 403/12; C07D 405/12; C07D 405/14; C07D 417/14; C07D 471/04; A61P 35/00
USPC .................................................... 514/217.05
See application file for complete search history.

(56) References Cited

U.S. PATENT DOCUMENTS

| | | | |
|---|---|---|---|
| 4,657,760 A | 4/1987 | Kung | |
| 5,206,344 A | 4/1993 | Katre et al. | |
| 5,225,212 A | 7/1993 | Martin et al. | |
| 7,452,997 B2 | 11/2008 | Lagu et al. | |
| 2006/0235013 A1* | 10/2006 | Georges | C07D 487/04 514/234.2 |
| 2011/0053909 A1 | 3/2011 | Alcaraz et al. | |
| 2012/0207765 A1 | 8/2012 | Kokubo et al. | |
| 2014/0221333 A1* | 8/2014 | De Man | C07D 487/04 514/210.02 |
| 2018/0155295 A1 | 6/2018 | Schiltz et al. | |

FOREIGN PATENT DOCUMENTS

| | | |
|---|---|---|
| WO | WO 2004097009 A2 | 11/2004 |
| WO | WO 2005075465 A1 | 8/2005 |
| WO | WO 2016179349 A1 | 11/2016 |

OTHER PUBLICATIONS

Alsayed et al., Mechanisms of regulation of CXCR4/SDF-1 (CXCL12)-dependent migration and homing in multiple myeloma, Blood, vol. 109(7), pp. 2708-2717, 2007.
Azab et al., CXCR4 inhibitor AMD3100 disrupts the interaction of multiple myeloma cells with the bone marrow microenvironment and enhances their sensitivity to therapy, Blood, vol. 113(18), pp. 4341-4351, 2009.
Beider et al., CXCR4 antagonist 4F-benzoyl-TN14003 inhibits leukemia and multiple myeloma tumor growth, Exp Hematol, vol. 39(3), pp. 282-292, 2011.
Bodner et al., CD4 dependence of gp120IIIB-CXCR4 interaction is cell-type specific, J Neuroimmunol, vol. 140, pp. 1-12, 2003.
Brelot et al., Identification of Residues of CXCR4 Critical for Human Immunodeficiency Virus Coreceptor and Chemokine Receptor Activities, J Biol Chem, vol. 275(31), pp. 23736-23744, 2000.
Bridger et al., Synthesis and structure-activity relationships of azamacrocyclic C-X-C chemokine receptor 4 antagonists: analogues containing a single azamacrocyclic ring are potent inhibitors of T-cell tropic (X4) HIV-1 replication, J Med Chem, vol. 53(3), pp. 1250-1260, 2010.
Busillo et al., Regulation of CXCR4 signaling, Biochimica et Biophysica Acta, vol. 1768(4), pp. 952-963, 2007.
Carter et al., Chapter 12 The Use of Receptor Homology Modeling to Facilitate the Design of Selective Chemokine Receptor Antagonists, Methods in Enzymology, vol. 461, pp. 249-279, 2009.

(Continued)

*Primary Examiner* — Yevgeny Valenrod
(74) *Attorney, Agent, or Firm* — Casimir Jones SC; David W. Staple

(57) ABSTRACT

Provided herein are small molecule modulators of CXCR4 activity (e.g., agonists, antagonists, inverse agonists, partial agonists), and methods of use thereof (e.g., for the treatment of disease).

8 Claims, 27 Drawing Sheets

(56) References Cited

OTHER PUBLICATIONS

Choi et al., Unique Ligand Binding Sites on CXCR4 Probed by a Chemical Biology Approach: Implications for the Design of Selective Human Immunodeficiency Virus Type 1 Inhibitors, J Virol, vol. 79(24), pp. 15398-15404, 2005.
Cross et al., Comparison of Several Molecular Docking Programs: Pose Prediction and Virtual Screening Accuracy, J Chem Inf Model, vol. 49(6), pp. 1455-1474, 2009.
Guyon et al., Baclofen and Other GABAB Receptor Agents Are Allosteric Modulators of the CXCL12 Chemokine Receptor CXCR4, J Neurosci, vol. 33(28), pp. 11643-11654, 2013.
Han, Chapter Nine—Constitutively Active Chemokine CXC Receptors, Adv Pharmacol, vol. 70, pp. 265-301, 2014.
Haribabu et al., Regulation of Human Chemokine Receptors CXCR4: Role of Phosphorylation in Desensitization and Internalization, J Biol Chem, vol. 272(45), pp. 28726-28731, 1997.
Jain, Surflex: Fully Automatic Flexible Molecular Docking Using a Molecular Similarity-Based Search Engine, J Med Chem, vol. 46(4), pp. 499-511, 2003.
Li et al., Multiple roles of chemokine CXCL12 in the central nervous system: A migration from immunology to neurobiology, Prog Neurobiol, vol. 84(2), pp. 116-131, 2008.
Liang et al., Development of a Unique Small Molecule Modulator of CXCR4, PLoS One, vol. 7(4), pp. e34028, 2012.
Lu et al., Abnormal development of the hippocampal dentate gyrus in mice lacking the CXCR4 chemokine receptor, PNAS, vol. 99(10), pp. 7090-7095, 2002.
Mithal et al., CXCL12 Signaling in the Development of the Nervous System, J Neuroimmune Pharmacol, vol. 7(4), pp. 820-834, 2012.
Mysinger et al., Structure-based ligand discovery for the protein-protein interface of chemokine receptor CXCR4, PNAS, vol. 109(14), pp. 5517-5522, 2012.
Nervi et al., Chemosensitization of acute myeloid leukemia (AML) following mobilization by the CXCR4 antagonist AMD3100, Blood, vol. 113(24), pp. 6206-6214, 2009.
Neves et al., Ligand-guided optimization of CXCR4 homology models for virtual screening using a multiple chemotype approach, J Comput Aided Mol Des, vol. 24(12), pp. 1023-1033, 2010.
Perez-Nueno et al., Comparison of Ligand-Based and Receptor-Based Virtual Screening of HIV Entry Inhibitors for the CXCR4 and CCR5 Receptors Using 3D Ligand Shape Matching and Ligand-Receptor Docking, J Chem Inf Model, vol. 48(3), pp. 509-533, 2008.
Perez-Nueno et al., Discovery of Novel HIV Entry Inhibitors for the CXCR4 Receptor by Prospective Virtual Screening, J Chem Inf Model, vol. 49(4), pp. 810-823, 2009.
Pubchem, Substance Record for SID 217694640 Create Date: Oct. 20, 2014. Retreived on Aug. 15, 2016 from the internet:<https://pubchem.ncbi.nlm.nih.gov/substance/217694640>.
Quoyer et al., Pepducin targeting the C-X-C chemokine receptor type 4 acts as a biased agonist favoring activation of the inhibitory G protein, PNAS, vol. 110(52), pp. E5088-E5097, 2013.
Roland et al., Role of the intracellular domains of CXCR4 in SDF-1-mediated signaling, Blood, vol. 101(2), pp. 399-406, 2003.
Singh et al., Targeting HIV-1 Through Molecular Modeling and Docking Studies of CXCR4: Leads for Therapeutic Development, vol. 69(3), pp. 191-203, 2007.
Skerlj et al.,Synthesis and SAR of novel CXCR4 antagonists that are potent inhibitors of T tropic (X4) HIV-1 replication, Bioorg Med Chem Lett, vol. 21(1), pp. 262-266, 2011.
Tavor et al., CXCR4 Regulates Migration and Development of Human Acute Myelogenous Leukemia Stem Cells in Transplanted NOD/SCID Mice, Cancer Res, vol. 64(8), pp. 2817-2824, 2004.
Tavor et al., The CXCR4 antagonist AMD3100 impairs survival of human AML cells and induces their differentiation, Leukemia, vol. 22(12), pp. 2151-2158, 2008.
Thoma et al., Orally Bioavailable Isothioureas Block Function of the Chemokine Receptor CXCR4 In Vitro and In Vivo, J Med Chem, vol. 51(24), pp. 7915-7920, 2008.
Tian et al., Distinct Functional Sites for Human Immunodeficiency Virus Type 1 and Stromal Cell-Derived Factor 1α on CXCR4 Transmembrane Helical Domains, J Virol, vol. 79(20), pp. 12667-12673, 2005.
Tran et al., The HIV-1 coat protein gp120 regulates cxcr4-mediated signaling in neural progenitor cells, J Neuroimmunol, vol. 160, pp. 68-76, 2005.
Ueda et al., Identification of novel non-peptide CXCR4 antagonists by ligand-based design approach, Bioorg Med Chem Lett, vol. 18(14), pp. 4124-4129, 2008.
Urbano et al., Modulators of the Sphingosine 1-Phosphate Receptor 1, Bioorg Med Chem Lett, vol. 23(23), pp. 6377-6389, 2013.
Vabeno et al., Insight into the Binding Mode for Cyclopentapeptide Antagonists of the CXCR4 Receptor, Chem Biol Drug Des, vol. 67(5), pp. 346-354, 2006.
Weisberg et al., Inhibition of CXCR4 in CML cells disrupts their interaction with the bone marrow microenvironment and sensitizes them to nilotinib, Leukemia, vol. 26(5), pp. 985-990, 2012.
Wong et al., Comparison of the potential multiple binding modes of bicyclam, monocylam, and noncyclam small-molecule CXC chemokine receptor 4 inhibitors, Mol Pharmacol, vol. 74(6), pp. 1485-1495, 2008.
Wu et al., Structures of the CXCR4 chemokine receptor in complex with small molecule and cyclic peptide antagonists, Science, vol. 330(6007), pp. 1066-1071, 2010.
Zhang et al., A Point Mutation That Confers Constitutive Activity to CXCR4 Reveals That T140 Is an Inverse Agonist and That AMD3100 and ALX40-4C Are Weak Partial Agonists, J Biol Chem, vol. 277(27), pp. 24515-24521, 2002.
Zhong et al., New G-protein-coupled receptor structures provide insights into the recognition of CXCL12 and HIV-1 gp120 by CXCR4, Acta Biochim Biophys Sin, vol. 43(5), pp. 337-338, 2011.
Zhou et al., Structural and Functional Characterization of Human CXCR4 as a Chemokine Receptor and HIV-1 Co-receptor by Mutagenesis and Molecular Modeling Studies, J Bio Chem, vol. 276(46), pp. 42826-42833, 2001.
International Search Report of related PCT/US2016/30891, dated Sep. 23, 2016, 9 pages.

* cited by examiner

CXCR4 CHEMOKINE RECEPTOR MODULATORS

CROSS-REFERENCE TO RELATED APPLICATIONS

The present application claims the priority benefit of U.S. Provisional Patent Application 62/157,285, filed May 5, 2015, which is incorporated by reference in its entirety.

STATEMENT REGARDING FEDERAL FUNDING

This invention was made with government support under grant numbers R01 AR064251, R01 DA013141, and R01 CA18907 awarded by the National Institutes of Health. The government has certain rights in the invention.

FIELD

Provided herein are small molecule modulators of CXCR4 activity (e.g., agonists, antagonists, inverse agonists, partial agonists), and methods of use thereof (e.g., for the treatment of disease).

BACKGROUND

The chemokine CXCL12 (SDF-1) and its cognate receptor CXCR4 are involved in a large number of physiological processes including HIV infectivity, inflammation, tumorigenesis, stem cell migration, and autoimmune diseases. There has been one approved drug that targets CXCR4, an antagonist which is used for stem cell mobilization prior to autologous stem cell transplantation. However, this drug has the potential for several important side effects such as leukocytosis and possible effects on the cardiovascular system. New CXCR4-acting agents could provide therapeutics against a wide variety of diseases.

Although inflammatory cytokines were originally named for their important role in the regulation of immune cell function, it is now clear that they also have important effects in many other tissues including the nervous system. The "chemotactic cytokines," or chemokines are a case in point. These small secreted proteins exert their effects through the activation of a family of Gprotein coupled receptors (GPCRs) and were originally shown to be key mediators of the inflammatory response due to their powerful chemoattractant effects on different classes of leukocytes. However, it is now known that the most ancient function of chemokine signaling concerned their ability to regulate the migration and development of stem cells. Indeed, CXCR4 chemokine receptor signaling is important in the development of all tissues.(ref. 1; herein incorporated by reference in its entirety) For example, it has been demonstrated that SDF-1/CXCR4 is important for the formation of the hippocampal dentate gyrus (DG)1a, and the importance of CXCR4 signaling in the development of many structures in both the central and peripheral nervous systems has also been demonstrated.(ref. 1; herein incorporated by reference in its entirety) Moreover, the developmental functions of CXCR4 signaling are still apparent in the adult.(refs. 1 b, 1c; herein incorporated by reference in their entireties) The role of CXCR4 in anchoring haemopoietic stem cells in the bone marrow is a well-known example of this. In addition, it is also clear that CXCR4 plays an important role in the regulation of cancer metastasis.(ref. 1; herein incorporated by reference in its entirety) Of great significance is that the CXCR4 receptor acts as a receptor for HIV-1 allowing it to infect lymphocytes and other cells.

Inhibition of CXCR4 signaling may be an important therapeutic strategy in many circumstances including cancer, HIV-1 pathogenesis, and several functions within the nervous system.(refs.1a, 1b; herein incorporated by reference in their entireties) A large number of investigations have sought to produce CXCR4 antagonists for therapeutic purposes.(ref. 2; herein incorporated by reference in its entirety) In addition, CXCR4 agonists or partial agonists which can rapidly desensitize CXCR4 receptors might also inhibit CXCR4 signaling by such a mechanism and may also have other important signaling consequences. However, apart from peptide mimics, no small molecule CXCR4 agonists have been reported.

Previous approaches to the discovery of new CXCR4 antagonists have relied largely on ligand-based techniques because GPCRs are notoriously difficult to crystallize.;ref. 3; herein incorporated by reference in its entirety) CXCR4 antagonists have been discovered through modification of AMD3100,(ref. 2c; herein incorporated by reference in its entirety) peptide deconstruction,(ref. 2d; herein incorporated by reference in its entirety) or high-throughput screening (HTS).(refs.2e, 2f; herein incorporated by reference in their entireties) Recently, several crystal structures of CXCR4 were solved that provide valuable insight into its ligand binding.(ref. 4; herein incorporated by reference in its entirety) Analysis of the binding mode confirmed the importance of the charged residues identified from mutation studies (ref. 5; herein incorporated by reference in its entirety) and in addition, characterized a number of important hydrophobic interactions. Comparing virtual high-throughput screening (vHTS) using a protein homology model and the actual crystal structure indicates that the crystal structure provided a significantly better receptor for docking than did the model.(ref. 6; herein incorporated by reference in its entirety).

SUMMARY

Provided herein are small molecule modulators of CXCR4 activity (e.g., agonists, antagonists, inverse agonists, partial agonists), and methods of use thereof (e.g., for the treatment of disease).

In some embodiments, provided herein are compositions comprising a compound or Formula (1):

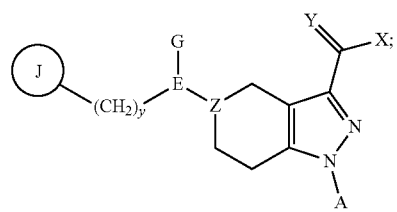

wherein Z is C or N;
wherein E is C, S, N, O, or absent; when E is absent Z and $(CH_2)_y$ are directly linked by a single covalent bond;
wherein G is $CH_3$, CN, halogen (e.g., Cl, Br, F, etc.), trihalomethane (e.g., $CCl_3$, $CBr_3$, $CF_3$, etc.), OH, $NH_2$, $alkyl_{1-6}$-$CH_3$, $alkyl_{1-6}$-CN, $alkyl_{1-6}$-halogen (e.g., Cl, Br, F, etc.), $alkyl_{1-6}$-trihalomethane (e.g., $CCl_3$, $CBr_3$, $CF_3$, etc.), $alkyl_{1-6}$-OH, or $alkyl_{1-6}$-$NH_2$;

wherein y is 0-6;
wherein

is any carbocycle, heterocycle, aryl, heteroaryl, or multi-ring systems thereof, and

is optionally substituted at any suitable positions with $CH_3$, CN, halogen (e.g., Cl, Br, F, etc.), trihalomethane (e.g., $CCl_3$, $CBr_3$, $CF_3$, etc.), OH, $NH_2$, $alkyl_{1-6}$-$CH_3$, $alkyl_{1-6}$-CN, $alkyl_{1-6}$-halogen (e.g., Cl, Br, F, etc.), $alkyl_{1-6}$-trihalomethane (e.g., $CCl_3$, $CBr_3$, $CF_3$, etc.), $alkyl_{1-6}$-OH, or $alkyl_{1-6}$-$NH_2$.

wherein A is $CH_3$, CN, halogen (e.g., Cl, Br, F, etc.), trihalomethane (e.g., $CCl_3$, $CBr_3$, $CF_3$, etc.), OH, $NH_2$, $alkyl_{1-6}$-$CH_3$, $alkyl_{1-6}$-CN, $alkyl_{1-6}$-halogen (e.g., Cl, Br, F, etc.), $alkyl_{1-6}$-trihalomethane (e.g., $CCl_3$, $CBr_3$, $CF_3$, etc.), $alkyl_{1-6}$-OH, $alkyl_{1-6}$-$NH_2$, a carbocycle, a heterocycle, an aryl, a heteroaryl, a multi-ring system thereof, or absent;
wherein Y is C, S, O, or absent;
wherein X is:

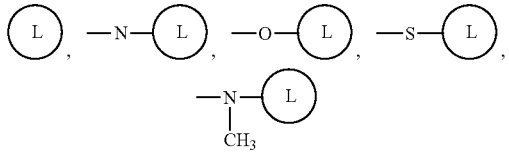

NH-$alkyl_{1-6}$, O-$alkyl_{1-6}$, S-$alkyl_{1-6}$, $CH_2$-$alkyl_{1-6}$, NH-$alkyl_{1-6}$-O-methyl, O-$alkyl_{1-6}$-O-methyl, S-$alkyl_{1-6}$-O-methyl, $CH_2$-$alkyl_{1-6}$-O-methyl, wherein N-dimethyl; and wherein

is any carbocycle, heterocycle, aryl, heteroaryl, or multi-ring systems thereof, and

is optionally substituted at any suitable positions with $CH_3$, CN, halogen (e.g., Cl, Br, F, etc.), trihalomethane (e.g., $CCl_3$, $CBr_3$, $CF_3$, etc.), OH, $NH_2$, $alkyl_{1-6}$-$CH_3$, $alkyl_{1-6}$-CN, $alkyl_{1-6}$-halogen (e.g., Cl, Br, F, etc.), $alkyl_{1-6}$-trihalomethane (e.g., $CCl_3$, $CBr_3$, $CF_3$, etc.), $alkyl_{1-6}$-OH, or $alkyl_{1-6}$—$NH_2$; or
a pharmaceutically acceptable salt therof.

In some embodiments, the compound binds to CXCR4. In some embodiments, the compound is a modulator of CXCR4 activity. In some embodiments, the compound is a CXCR4 agonist. In some embodiments, the compound is a CXCR4 antagonist. In some embodiments, the compound is selected from the compounds of Table 2. In some embodiments, the compound is selected from the group consisting of: NUCC-0176286, NUCC-0176287, NUCC-0176288, NUCC-0176289, NUCC-0176290, NUCC-0176291, NUCC-0176292, NUCC-0176293, NUCC-0176294, NUCC-0176295, NUCC-0176296, NUCC-0176297, NUCC-0176298, NUCC-0176299, NUCC-0176300, NUCC-0176301, NUCC-0176302, NUCC-0176303, NUCC-0176304, NUCC-0176305, NUCC-0176306, NUCC-0176307, NUCC-0176308, NUCC-0176309, NUCC-0176310, NUCC-0176311, NUCC-0176312, NUCC-0176313, NUCC-0176314, NUCC-0176315, NUCC-0176316, NUCC-0176317, NUCC-0176318, NUCC-0176319, NUCC-0196315, NUCC-0196316, NUCC-0196317, NUCC-0196318, NUCC-0196319, NUCC-0196320, NUCC-0196321, NUCC-0196322, NUCC-0196323, NUCC-0196324, NUCC-0196325, NUCC-0196326, NUCC-0196327, NUCC-0196328, NUCC-0196329, NUCC-0196330, NUCC-0196331, NUCC-0196332, NUCC-0196333, NUCC-0196334, NUCC-0196335, NUCC-0196336, NUCC-0196337, NUCC-0196338, and NUCC-0196339.

In some embodiments, provided herein are methods of treating a subject comprising administering to the subject a composition and/or compound described herein. In some embodiments, the subject is treated for cancer.

In some embodiments, provided herein are methods of modulating CXCR4 activity comprising contacting CXCR4 with a composition and/or compound described herein (e.g., CXCR4 agonist, CXCR4 antagonist, etc.). In some embodiments, the disease is a cancer.

DEFINITIONS

Figure 1:
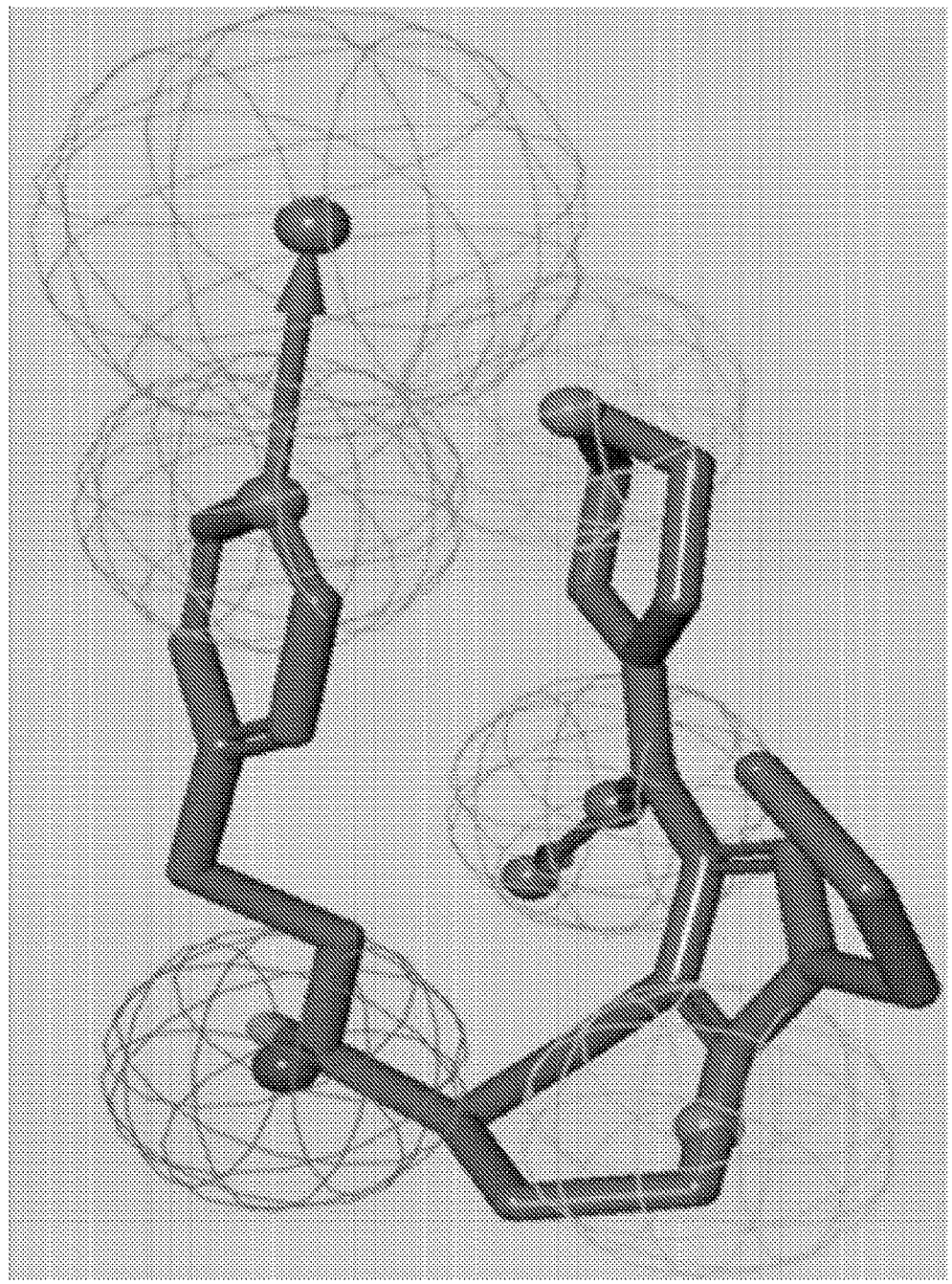
FIG. 1. Five-point pharmacophore used in virtual screening. Compound NUCC-390 is shown with the pharmacophore overlaid. Green=Hydrogen Bond Acceptor, Red=Positive Ionizable, Cyan=Hydrophobic. (b)

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a CXCR4 antagonist" is a reference to one or more CXCR4 antagonists and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

All chemical names of substituents should be interpreted in light of IUPAC and/or a modified format in which functional groups within a substituent are read in the order in which they branch from the scaffold or main structure. For example, in the modified nomenclature, methyl-sulfonyl-propanol refers to $CH_2SO_2CH_2CH_2CH_2OH$ or:

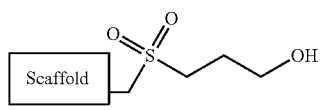

As another example, according to the modified nomenclature, a methyl-amine substituent is:

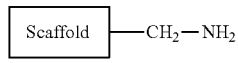

while an amino-methyl substituent is:

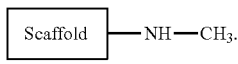

All chemical names of substituents should be interpreted in light of IUPAC and/or the modified nomenclature and with reference to the chemical structures depicted and/or described herein.

As used herein, the term "subject" broadly refers to any animal, including but not limited to, human and non-human animals (e.g., dogs, cats, cows, horses, sheep, poultry, fish, crustaceans, etc.). As used herein, the term "patient" typically refers to a subject that is being treated for a disease or condition.

As used herein, the term "subject at risk for a disease," for example, "a subject at risk for cancer" refers to a subject with one or more risk factors for developing the disease (e.g., cancer). Depending upon the specific disease, risk factors may include, but are not limited to, gender, age, genetic predisposition, environmental exposures, infections, and previous incidents of diseases, lifestyle, etc.

As used herein, the term "effective amount" refers to the amount of a composition sufficient to effect beneficial or desired results. An effective amount can be administered in one or more administrations, applications or dosages and is not intended to be limited to a particular formulation or administration route.

As used herein, the terms "administration" and "administering" refer to the act of giving a drug, prodrug, or other agent, or therapeutic treatment to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the terms "co-administration" and "co-administering" refer to the administration of at least two agent(s) (e.g., a CXCR4 antagonist and one or more additional therapeutics) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "pharmaceutical composition" refers to the combination of an active agent with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintigrants (e.g., potato starch or sodium starch glycolate), and the like. The compositions also can include stabilizers and preservatives. For examples of carriers, stabilizers and adjuvants, see, e.g., Martin, Remington's Pharmaceutical Sciences, 15th Ed., Mack Publ. Co., Easton, Pa. (1975), incorporated herein by reference in its entirety.

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like. Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds herein are contemplated as being pharmaceutically acceptable. However, salts of acids and bases that are non-pharmaceutically acceptable may also find use, for example, in the preparation or purification of a pharmaceutically acceptable compound.

As used herein, the term "instructions for administering said compound to a subject," and grammatical equivalents thereof, includes instructions for using the compositions contained in a kit for the treatment of conditions (e.g., providing dosing, route of administration, decision trees for treating physicians for correlating patient-specific characteristics with therapeutic courses of action).

As used herein, the term "alkyl" refers to a moiety consisting of carbon and hydrogen containing no double or triple bonds. An alkyl may be linear, branched, cyclic, or a combination thereof, and may contain from one to fifty carbon atoms, such as straight chain or branched $C^1$-$C^{20}$ alkane. Examples of alkyl groups include but are not limited to methyl, ethyl, propyl, isopropyl, cyclopropyl, butyl isomers (e.g. n-butyl, iso-butyl, tert-butyl, etc.) cyclobutyl isomers (e.g. cyclobutyl, methylcyclopropyl, etc.), pentyl isomers, cyclopentane isomers, hexyl isomers, cyclohexane isomers, and the like. Unless specified otherwise (e.g., substituted alkyl group, heteroalkyl, alkoxy group, haloalkyl, alkylamine, thioalkyl, etc.), an alkyl group contains carbon and hydrogen atoms only.

As used herein, "alkylene" or "alkylene chain" refers to a straight or branched divalent hydrocarbon chain linking the rest of the molecule to a radical group, consisting solely of carbon and hydrogen, containing no unsaturation, and preferably having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group may be through any two carbons within the chain. In certain embodiments, an alkylene comprises one to ten carbon atoms (i.e., $C_1$-$C_{10}$ alkylene). In certain embodiments, an alkylene comprises one to eight carbon atoms (i.e., $C_1$-$C_8$ alkylene). In other embodiments, an alkylene comprises one to five carbon atoms (i.e., $C_1$-$C_5$ alkylene). In other embodiments, an alkylene comprises one to four carbon atoms (i.e., $C_1$-$C_4$ alkylene). In other embodiments, an alkylene comprises one to three carbon atoms (i.e., $C_1$-$C_3$ alkylene). In other embodiments, an alkylene comprises one to two carbon atoms (i.e., $C_1$-$C_2$ alkylene). In other embodiments, an alkylene comprises one carbon atom (i.e., $C_1$ alkylene). Unless stated otherwise specifically in the specification, an alkylene chain is optionally substituted by one or more substituents such as those substituents described herein.

As used herein, the term "alkenyl" refers to a straight or branched hydrocarbon chain radical group consisting solely of carbon and hydrogen atoms, containing at least one carbon-carbon double bond, and preferably having from two to twelve carbon atoms (i.e., $C_2$-$C_{12}$ alkenyl). In certain embodiments, an alkenyl comprises two to eight carbon atoms (i.e., $C_2$-$C_8$ alkenyl). In certain embodiments, an alkenyl comprises two to six carbon atoms (i.e., $C_2$-$C_6$ alkenyl). In other embodiments, an alkenyl comprises two to four carbon atoms (i.e., $C_2$-$C_4$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more substituents such as those substituents described herein.

As used herein, "alkenylene" or "alkenylene chain" refers to a straight or branched divalent hydrocarbon chain linking the rest of the molecule to a radical group, consisting solely of carbon and hydrogen, containing at least one carbon-carbon double bond, and preferably having from two to twelve carbon atoms. The alkenylene chain is attached to the rest of the molecule through a single bond and to the radical group through a single bond. The points of attachment of the alkenylene chain to the rest of the molecule and to the radical group may be through any two carbons within the chain. In certain embodiments, an alkenylene comprises two to ten carbon atoms (i.e., $C_2$-$C_{10}$ alkenylene). In certain embodiments, an alkenylene comprises two to eight carbon atoms (i.e., $C_2$-$C_8$ alkenylene). In other embodiments, an alkenylene comprises two to five carbon atoms (i.e., $C_2$-$C_5$ alkenylene). In other embodiments, an alkenylene comprises two to four carbon atoms (i.e., $C_2$-$C_4$ alkenylene). In other embodiments, an alkenylene comprises two to three carbon atoms (i.e., $C_2$-$C_3$ alkenylene). In other embodiments, an alkenylene comprises two carbon atom (i.e., $C_2$ alkenylene). Unless stated otherwise specifically in the specification, an alkenylene chain is optionally substituted by one or more substituents such as those substituents described herein.

As used herein, the term "alkynyl" refers to a straight or branched hydrocarbon chain radical group consisting solely of carbon and hydrogen atoms, containing at least one carbon-carbon triple bond, and preferably having from two to twelve carbon atoms (i.e., $C_2$-$C_{12}$ alkynyl). In certain embodiments, an alkynyl comprises two to eight carbon atoms (i.e., $C_2$-$C_8$ alkynyl). In other embodiments, an alkynyl comprises two to six carbon atoms (i.e., $C_2$-$C_6$ alkynyl). In other embodiments, an alkynyl comprises two to four carbon atoms (i.e., $C_2$-$C_4$ alkynyl). The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more substituents such as those substituents described herein.

As used herein "alkynylene" or "alkynylene chain" refers to a straight or branched divalent hydrocarbon chain linking the rest of the molecule to a radical group, consisting solely of carbon and hydrogen, containing at least one carbon-carbon triple bond, and preferably having from two to twelve carbon atoms. The alkynylene chain is attached to the rest of the molecule through a single bond and to the radical group through a single bond. The points of attachment of the alkynylene chain to the rest of the molecule and to the radical group may be through any two carbons within the chain. In certain embodiments, an alkynylene comprises two to ten carbon atoms (i.e., $C_2$-$C_{10}$ alkynylene). In certain embodiments, an alkynylene comprises two to eight carbon atoms (i.e., $C_2$-$C_8$ alkynylene). In other embodiments, an alkynylene comprises two to five carbon atoms (i.e., $C_2$-$C_5$ alkynylene). In other embodiments, an alkynylene comprises two to four carbon atoms (i.e., $C_2$-$C_4$ alkynylene). In other embodiments, an alkynylene comprises two to three carbon atoms (i.e., $C_2$-$C_3$ alkynylene). In other embodiments, an alkynylene comprises two carbon atom (i.e., $C_2$ alkynylene). Unless stated otherwise specifically in the specification, an alkynylene chain is optionally substituted by one or more substituents such as those substituents described herein.

As used herein, the term "amine" or "amino" includes primary, secondary, and tertiary amines wherein each non-hydrogen group on nitrogen may be selected from alkyl, aryl, and the like. Amines include but are not limited to —$NH_2$, —NH-phenyl, —NH—$CH_3$, —NH—$CH_2CH_3$, and —N($CH_3$)benzyl.

The term "amide" or "amido" includes C- and N-amide groups, e.g., —C(O)$NR_2$, and —NRC(O)R groups, respectively, where R can be H, alkyl, aryl, etc. Amide groups therefore include but are not limited to —C(O)$NH_2$, —NHC(O)H, —C(O)$NHCH_2CH_3$, —NHC(O)$CH_3$, —C(O)N($CH_2CH_3$)phenyl.

As used herein, the term "linear alkyl" refers to a chain of carbon and hydrogen atoms (e.g., ethane, propane, butane, pentane, hexane, etc.). A linear alkyl group may be referred to by the designation —$(CH_2)_qCH_3$, where q is 0-49. The designation "$C_{1-12}$ alkyl" or a similar designation, refers to alkyl having from 1 to 12 carbon atoms such as methyl, ethyl, propyl isomers (e.g. n-propyl, isopropyl, etc.), butyl isomers, cyclobutyl isomers (e.g. cyclobutyl, methylcyclopropyl, etc.), pentyl isomers, cyclopentyl isomers, hexyl isomers, cyclohexyl isomer, heptyl isomers, cycloheptyl isomers, octyl isomers, cyclooctyl isomers, nonyl isomers, cyclononyl isomers, decyl isomer, cyclodecyl isomers, etc. Similar designations refer to alkyl with a number of carbon atoms in a different range.

The term "$C_{x-y}$" when used in conjunction with a chemical moiety, such as alkyl, alkenyl, alkynyl, or carbocycle is meant to include groups that contain from x to y carbons in the chain or ring. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. The terms "$C_{x-y}$alkenyl" and "$C_{x-y}$alkynyl" refer to substituted or unsubstituted unsaturated aliphatic groups analogous in length and possible substitution to the alkyls described above, but that contain at least one double or triple bond respectively. The term "$C_{x-y}$carbocycle" refers to a substituted or unsubstituted carbocycle, that contain from x to y ring carbons.

As used herein, the term "branched alkyl" refers to a chain of carbon and hydrogen atoms, without double or triple bonds, that contains a fork, branch, and/or split in the chain (e.g., 3,5-dimethyl-2-ethylhexane, 2-methyl-pentane, 1-methyl-cyclobutane, ortho-diethyl-cyclohexane, etc.). "Branching" refers to the divergence of a carbon chain, whereas "substitution" refers to the presence of non-carbon/non-hydrogen atoms in a moiety. Unless specified otherwise (e.g., substituted branched alkyl group, branched heteroalkyl, branched alkoxy group, branched haloalkyl, branched alkylamine, branched thioalkyl, etc.), a branched alkyl group contains carbon and hydrogen atoms only.

As used herein, the term "carbocycle" refers to a saturated, unsaturated or aromatic ring in which each atom of the ring is carbon. Carbocycle includes monocyclic, bicyclic and polycyclic rings, wherein bicyclic or polycyclic rings may include fused, or Spiro rings. Carbocycle may include 3- to 10-membered monocyclic rings, 6- to 12-membered bicyclic rings, and 6- to 12-membered bridged rings. Each ring of a bicyclic or polycyclic carbocycle may be selected from saturated, unsaturated, and aromatic rings. In an exemplary embodiment, an aromatic carbocycle, e.g., phenyl, may be fused to a saturated or unsaturated ring, e.g., cyclohexane, cyclopentane, or cyclohexene. In some embodiments, the carbocycle is an aromatic carbocycle. In some embodiments, the carbocycle is a cycloalkyl. In some embodiments, the carbocycle is a cycloalkenyl. Exemplary carbocycles include cyclopentyl, cyclohexyl, cyclohexenyl, adamantyl, phenyl, indanyl, and naphthyl. Unless stated otherwise specifically in the specification, a carbocycle is optionally substituted by one or more substituents such as those described herein. A "non-aromatic carbocycle" includes rings and rign systems that are saturated, unsaturated, substituted, unsubstituted, etc., but not aromatic or aryl rings or ring systems.

As used herein, the term "cycloalkyl" refers to a completely saturated mono- or multi-cyclic hydrocarbon ring system. When composed of two or more rings, the rings may be joined together in a fused, bridged or spiro-connected fashion. Cycloalkyl groups of the present application may range from three to ten carbons ($C_3$ to $C_{10}$). A cycloalkyl group may be unsubstituted, substituted, branched, and/or unbranched. Typical cycloalkyl groups include, but are not limited to, cyclopropyl, cyclobutyl, cyclopentyl, cyclohexyl, and the like. If substituted, the substituent(s) may be an alkyl or selected from those indicated above with regard to substitution of an alkyl group unless otherwise indicated. Unless specified otherwise (e.g., substituted cycloalkyl group, heterocyclyl, cycloalkoxy group, halocycloalkyl, cycloalkylamine, thiocycloalkyl, etc.), an alkyl group contains carbon and hydrogen atoms only.

As used herein, the term "cycloalkenyl" refers to a stable unsaturated non-aromatic monocyclic, bicyclic or polycyclic hydrocarbon radical consisting solely of carbon and hydrogen atoms, which includes fused or bridged ring systems, preferably having from three to twelve carbon atoms and comprising at least one double bond. In certain embodiments, a cycloalkenyl comprises three to ten carbon atoms. In other embodiments, a cycloalkenyl comprises five to seven carbon atoms. The cycloalkenyl may be attached to the rest of the molecule by a single bond. Examples of monocyclic cycloalkenyls include, e.g., cyclopentenyl, cyclohexenyl, cycloheptenyl, and cyclooctenyl. Unless otherwise stated specifically in the specification, the term "cycloalkenyl" is meant to include cycloalkenyl radicals that are optionally substituted by one or more substituents such as those substituents described herein.

As used herein, the term "heteroalkyl" refers to an alkyl group, as defined herein, wherein one or more carbon atoms are independently replaced by one or more heteroatoms (e.g., oxygen, sulfur, nitrogen, phosphorus, silicon, or combinations thereof). The alkyl group containing the non-carbon substitution(s) may be a linear alkyl, branched alkyl, cycloalkyl (e.g., cycloheteroalkyl), or combinations thereof. Non-carbons may be at terminal locations (e.g., 2-hexanol) or integral to an alkyl group (e.g., diethyl ether). Unless stated otherwise specifically in the specification, the heteroalkyl group may be optionally substituted as described herein. Representative heteroalkyl groups include, but are not limited to —$OCH_2$OMe, —$OCH_2CH_2$OMe, or —$OCH_2CH_2OCH_2CH_2NH_2$.

As used herein, the term "heteroalkylene" refers to an alkyl radical as described above where one or more carbon atoms of the alkyl is replaced with a heteroatom, e.g., O, N or S. "Heteroalkylene" or "heteroalkylene chain" refers to a straight or branched divalent heteroalkyl chain linking the rest of the molecule to a radical group. Unless stated otherwise specifically in the specification, the heteroalkylene group may be optionally substituted as described herein. Representative heteroalkylene groups include, but are not limited to —$OCH_2CH_2O$—, —$OCH_2CH_2OCH_2CH_2O$—, or —$OCH_2CH_2OCH_2CH_2OCH_2CH_2O$—.

The term "substituted" refers to moieties having substituents replacing a hydrogen on one or more carbons or substitutable heteroatoms, e.g., of the structure. It will be understood that "substitution" or "substituted with" includes the implicit proviso that such substitution is in accordance with permitted valence of the substituted atom and the substituent, and that the substitution results in a stable compound, i.e., a compound which does not spontaneously undergo transformation such as by rearrangement, cyclization, elimination, etc. Substitution of a structure depicted herein may result in removal or moving of a double bond or other bond, as will be understood by one in the field. In certain embodiments, substituted refers to moieties having substituents replacing two hydrogen atoms on the same carbon atom, such as substituting the two hydrogen atoms on a single carbon with an oxo, imino or thioxo group. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms.

The term "optionally substituted", as used herein, means that the referenced group (e.g., alkyl, cycloalkyl, etc.) may or may not be substituted with one or more additional group(s). Non-limiting examples of substituents include, for example: halogen, hydroxy, oxo (=O), thioxo (=S), cyano (—CN), nitro (—$NO_2$), imino (=N—H), oximo (=N—OH), hydrazino (=N—$NH_2$), —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t OR^a$ (where t is 1 or 2), and —$R^b$—S(O)$_t$N($R^a$)$_2$ (where t is 1 or 2); and alkyl, alkenyl, alkynyl, each of which may be optionally substituted by halogen, oxo (=O), thioxo (=S), cyano (—CN), nitro (—$NO_2$), imino (=N—H), oximo (=N—OH), hydrazine (=N—$NH_2$), —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t OR^a$ (where t is 1 or 2), —$R^b$—S(O)$_t$N($R^a$)$_2$ (where t is 1 or 2), carbocycle and heterocycle; wherein each $R^a$ is independently selected from hydrogen, alkyl, alkenyl, alkynyl, carbocycle and heterocycle, wherein each $R^a$, valence permitting, may be optionally substituted with halogen, oxo (=O), thioxo (=S), cyano (—CN), nitro (—$NO_2$), imino (=N—H), oximo (=N—OH), hydrazine (=N—$NH_2$), —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t R^a$ (where t is 1 or 2), —$R^b$—S(O)$_t OR^a$ (where t is 1 or 2) and —$R^b$—S(O)$_t$N($R^a$)$_2$ (where t is 1 or 2); and wherein each $R^b$ is independently selected from a direct bond or a straight or branched alkylene, alkenylene, or alkynylene chain, and each $R^c$ is a straight or branched alkylene, alkenylene or alkynylene chain. Substituent groups may be selected from, but are not limited to: alkyl, alkenyl, alkynyl, cycloalkyl, aryl, heteroaryl, heterocycloalkyl, hydroxyl, alkoxy, mercaptyl, cyano, halo, carbonyl, thiocarbonyl, isocyanato, thiocyanato, isothiocyanato, nitro, perhaloalkyl, perfluoroalkyl, and amino, including mono- and di-substituted amino groups, and the protected derivatives thereof.

As used herein, the term "haloalkyl" or "haloalkane" refers to an alkyl radical, as defined above, that is substituted by one or more halogen radicals, for example, trifluoromethyl, dichloromethyl, bromomethyl, 2,2,2-trifluoroethyl, 1-fluoromethyl-2-fluoroethyl, and the like. In some embodiments, the alkyl part of the fluoroalkyl radical is optionally further substituted. Examples of halogen substituted alkanes ("haloalkanes") include halomethane (e.g., chloromethane, bromomethane, fluoromethane, iodomethane), di-and trihalomethane (e.g., trichloromethane, tribromomethane, trifluoromethane, triiodomethane), 1-haloethane, 2-haloethane, 1,2-dihaloethane, 1-halopropane, 2-halopropane, 3-halopropane, 1,2-dihalopropane, 1,3-dihalopropane, 2,3-dihalopropane, 1,2,3-trihalopropane, and any other suitable combinations of alkanes (or substituted alkanes) and halogens (e.g., Cl, Br, F, I, etc.). When an alkyl group is substituted with more than one halogen radicals, each halogen may be independently selected e.g., 1-chloro, 2-fluoroethane.

As used herein, the terms "aromatic ring," "aryl group," and "aryl ring" refer to aromatic carbocycles and aromatic heterocycles. Exemplary atomatic rings include furan, benzofuran, isobenzofuran, pyrrole, indole, isoindole, thiophene, benzothiophene, benzo(c)thiophene, imidazole, benzimidazole, purine, pyrazole, indazole, oxazole, benzooxazole, isoxazole, benzisoxazole, thiazole, benzothiazole, benzene, napthalene, pyridine, quinolone, isoquinoline, pyrazine, quinoxaline, pyrimidine, quinazoline, pyridazine, cinnoline, phthalazine, triazine (e.g., 1,2,3-triazine; 1,2,4-triazine; 1,3,5 triazine), and thiadiazole. The term "aromatic carbocycle" refers to an aromatic ring without heteroatoms present within the ring structure.

As used herein, the terms "heteroaryl" or "heteroaromatic" refer to monocyclic, bicyclic, or polycyclic ring systems, wherein at least one ring in the system is aromatic and contains at least one heteroatom, for example, nitrogen, oxygen and sulfur. Each ring of the heteroaromatic ring systems may contain 3 to 7 ring atoms. Exemplary heteroaromatic monocyclic ring systems include 5- to 7-membered rings whose ring structures include one to four heteroatoms, for example, one or two heteroatoms. Heteroaryl groups include, for example, pyrrole, furan, thiophene, imidazole, oxazole, thiazole, pyrazole, pyridine, pyrazine, pyridazine, and pyrimidine, and the like.

Unless otherwise defined herein, suitable substituents on a heteroaryl group may be selected from halogen; —R, —OR, —SR, —NO$_2$, —CN, —N(R)$_2$, —NRC(O)R, —NRC(S)R, —NRC(O)N(R)$_2$, —NRC(S)N(R)$_2$, —NRCO$_2$R, —NRNRC(O)R, —NRNRC(O)N(R)$_2$, —NRNRCO$_2$R, —C(O)C(O)R, —C(O)CH$_2$C(O)R, —CO$_2$R, —C(S)R, —C(O)N(R)$_2$, —C(S)N(R)$_2$, —OC(O)N(R)$_2$, —OC(O)R, —C(O)N(OR)R, —C(NOR)R, —S(O)$_2$R, —S(O)$_3$R, —SO$_2$N(R)$_2$, —S(O)R, —NRSO$_2$N(R)$_2$, —NRSO$_2$R, —N(OR)R, —C(=NH)—N(R)$_2$, —P(O)$_2$R, —PO(R)$_2$, —OPO(R)$_2$, —(CH$_2$)O$_2$NHC(O)R, phenyl (Ph) optionally substituted with R, —O(Ph) optionally substituted with R, —(CH$_2$)1-2(Ph), optionally substituted with R, or —CH=CH(Ph), optionally substituted with R, wherein each independent occurrence of R is selected from hydrogen, optionally substituted C$_1$-C$_6$ alkyl, optionally substituted C$_1$-C$_6$ alkoxy, an unsubstituted 5-6 membered heteroaryl, phenyl, —O(Ph), or —CH$_2$(Ph), or two independent occurrences of R, on the same substituent or different substituents, taken together with the atom(s) to which each R is bound, to form an optionally substituted 3-12 membered saturated, partially unsaturated, or fully unsaturated monocyclic or bicyclic ring having 0-4 heteroatoms independently selected from nitrogen, oxygen, or sulfur. Non-limiting examples of heteroaryl groups, as used herein, include benzofuranyl, benzofurazanyl, benzoxazolyl, benzopyranyl, benzthiazolyl, benzothienyl, benzazepinyl, benzimidazolyl, benzothiopyranyl, benzo(1,3)dioxole, benzo(b)furyl, benzo(b)thienyl, cinnolinyl, furazanyl, furyl, furopyridinyl, imidazolyl, indolyl, indolizinyl, indolin-2-one, indazolyl, isoindolyl, isoquinolinyl, isoxazolyl, isothiazolyl, 1,8-naphthyridinyl, oxazolyl, oxaindolyl, oxadiazolyl, pyrazolyl, pyrrolyl, phthalazinyl, pteridinyl, purinyl, pyridyl, pyridazinyl, pyrazinyl, pyrimidinyl, quinoxalinyl, quinolinyl, quinazolinyl, 4H-quinolizinyl, thiazolyl, thiadiazolyl, thienyl, triazinyl, triazolyl and tetrazolyl. Any substituents depicted in structures or examples herein, should be viewed as suitable substituents for use in embodiments of the present invention.

As used herein, the term "heterocycle" refers to a saturated, unsaturated or aromatic ring comprising one or more heteroatoms. Exemplary heteroatoms include N, O, Si, P, B, and S atoms. Heterocycles include monocylic, bicylic or polycyclic rings, wherein bicyclic or polycyclic rings may include fused, or spiro rings. For bicyclic and polycyclic rings, at least one ring of the bicyclic or polycyclic ring comprises one or more heteroatoms. Heterocycles may include 3- to 10-membered monocyclic rings, 6- to 12-membered bicyclic rings, and 6- to 12-membered bridged rings. Each ring of a bicyclic or polycyclic heterocycle may be selected from saturated, unsaturated, and aromatic rings, as valence permits. In an exemplary embodiment, a heterocycle, e.g., pyridyl, may be fused to a saturated or unsaturated ring, e.g., cyclohexane, cyclopentane, or cyclohexene. In some embodiments, heterocyclic is selected from heteroaryl, heterocycloalkyl and heterocycloalkenyl.

As used herein, the term "non-aromatic heterocycle" refers to a cycloalkyl or cycloalkenyl, as defined herein, wherein one or more of the ring carbons are replaced by a moiety selected from —O—, —N=, —NR—, —C(O)—, —S—, —S(O)— or —S(O)$_2$—, wherein R is hydrogen, C$_1$-C$_8$ alkyl or a nitrogen protecting group, with the proviso that the ring of said group does not contain two adjacent O or S atoms. Non-limiting examples of non-aromatic heterocycles, as used herein, include morpholino, pyrrolidinyl, pyrrolidinyl-2-one, piperazinyl, piperidinyl, piperidinylone, 1,4-dioxa-8-aza-spiro(4.5)dec-8-yl, 2H-pyrrolyl, 2-pyrrolinyl, 3-pyrrolinyl, 1,3-dioxolanyl, 2-imidazolinyl, imidazolidinyl, 2-pyrazolinyl, pyrazolidinyl, 1,4-dioxanyl, 1,4-dithianyl, thiomorpholinyl, azepanyl, hexahydro-1,4-diazepinyl, tetrahydrofuranyl, dihydrofuranyl, tetrahydrothienyl, tetrahydropyranyl, dihydropyranyl, tetrahydrothiopyranyl, thioxanyl, azetidinyl, oxetanyl, thietanyl, oxepanyl, thiepanyl, 1,2,3,6-tetrahydropyridinyl, 2H-pyranyl, 4H-pyranyl, dioxanyl, 1,3-dioxolanyl, dithianyl, dithiolanyl, dihydropyranyl, dihydrothienyl, dihydrofuranyl, imidazolinyl, imidazolidinyl, 3-azabicyclo(3.1.0)hexanyl, and 3-azabicyclo(4.1.0)heptanyl, 3,8-diazabicyclo(3.2.1)octanyl, and 2,5-diazabicyclo(2.2.1)heptanyl. In certain embodiments, a non-aromatic heterocyclic ring is aziridine, thiirane, oxirane, oxaziridine, dioxirane, azetidine, oxetan, thietane, diazetidine, dioxetane, dithietane, pyrrolidine, tetrahydrofuran, thiolane, imidazolidine, pyrazolidine, oxazolidine, isoxazolidine, thiazolidine, isothiazolidine, dioxolane, dithiolane, piperdine, oxane, thiane, piperazine, morpholine, thiomorpholine, dioxane, dithiane, trioxane, thithiane, azepane, oxepane, thiepane, homopiperazine, or azocane.

As used herein, the term "absent" when used in reference to functional group or substituent, particularly in reference to the chemical structure of a compound, means that the particular functional group or substituent is not present in the compound being described. When used in refernce to a substituent, the absence of the substituent typically means that the bond to the substituent is absent and that absense of the bond is compensated for with a H atom. When used in refernce to a position within a chain or ring, the absence of the position typically means that the two postiions otherwise connetced by the absent positon are instead directly connected bu a covalent bond.

DETAILED DESCRIPTION

Provided herein are small molecule modulators of CXCR4 activity (e.g., agonists, antagonists, inverse agonists, partial agonists), and methods of use thereof (e.g., for the treatment of disease). Experiments conducted during development of embodiments herein have shown their effects in several assays indicative of therapeutic benefit, including cancer cell chemosensitization. In some embodiments, the agonist pharmacology demonstrated by these compounds enables different types of in vivo effects different from known CXCR4 antagonists and allows for therapeutic targeting using CXCR4 for new indications.

CXCR4 receptors play a key role in the biology of stem cells in all tissues as well as in the regulation of cancer metastasis and inflammation.(ref. 1; herein incorporated by reference in its entirety) Activation of CXCR4 receptors has a large number of signaling consequences for the cell including activation of diverse Gprotein and β-arrestin mediated pathways.

The cognate agonist for CXCR4 is the 93 amino acid protein CXCL12 (SDF-1) which fits inside a large binding site (2049 Å$^3$). This large size makes it difficult to find a small molecule that can bind in the pocket tightly, specifically, and predictably. However, mutagenesis refs.3b, 5a, 5b, 16; herein incorporated by reference in their entireties) and recent crystal structure docking studies (ref.6; herein incorporated by reference in its entirety) have provided evidence of several residues that are critical for binding of small molecules. Because of these known difficulties and the relative lack of published structure-based medicinal chemistry for GPCRs, experiments were conducted during development of embodiments described herein using multiple methods for hit identification to sample as large a chemical space as possible and increase the likelihood of successfully identifying multiple diverse drug-like CXCR4 chemotypes.

In an initial (Ca)i screen, it was observed that addition of the known CXCR4-selective antagonist AMD3100 completely blocked stimulation with SDF-1. Similarly, the novel structure NUCC-388 also produced a similar blocking response. On the other hand, when compounds such as NUCC-390 and NUCC-398 were added they produced their own response indicating that they might be CXCR4 agonists. Indeed, further work established the agonist nature of these compounds. In these studies it was demonstrated that the effects of NUCC-390 and NUCC-398 could be completely inhibited by the selective CXCR4 antagonist AMD3100. The observation that molecules like NUCC-390 produce agonist effects in the absence of even small additions of SDF-1 suggest that they are orthosteric agonists rather than PAMs. The observations that the effects of compounds such as NUCC-390 in the Ca imaging, ERK activation, receptor internalization, and chemotaxis assays are very similar to those produced by SDF-1, indicate that they have a mostly agonist-like profile.

The molecules identified and characterized herein are the first small molecule agonists of CXCR4.(ref. 2a; herein incorporated by reference in its entirety)

In some embodiments, provided herein is a dual in silico screening strategy using both ligand- and structure-based approaches to identify novel small molecule modulators of the CXCR4 receptor. Testing these new compounds in a series of in vitro assays demonstrated agonism of the CXCR4 receptor, pharmacology never previously described for small molecules.

Compositions and methods described herein find use in the treatment or prevention of cancer and cancer metastasis, infectious disease (e.g., HIV/AIDS, etc.), neuropathy, chronic pain, autoimmunedisease (e.g., multiple sclerosis, etc.), etc.

In certain embodiments, provided herein is a compound having a structure of Formula (1):

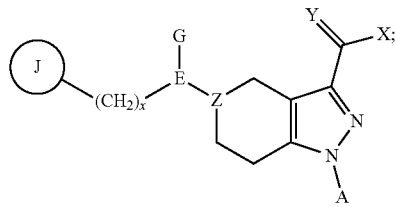

wherein:

Z is C or N;

E is C, S, N, O, or absent; when E is absent Z and (CH2)y are directly linked by a single covalent bond;

G is CH$_3$, CN, halogen (e.g., Cl, Br, F, etc.), trihalomethane (e.g., CCl$_3$, CBr$_3$, CF$_3$, etc.), OH, NH$_2$, alkyl$_{1-6}$-CH$_3$, alkyl$_{1-6}$-halogen (e.g., Cl, Br, F, etc.), alkyl$_{1-6}$-trihalomethane (e.g., CCl$_3$, CBr$_3$, CF$_3$, etc.), alkyl$_{1-6}$-OH, or alkyl$_{1-6}$—NH$_2$;

y is 0-6 (e.g., (CH$_2$)$_y$ is methyl, ethyl, propyl, butyl, pentyl, or hexyl);

is any carbocycle, heterocycle, aryl, heteroaryl, or multi-ring systems thereof, and

is optionally substituted at any suitable positions with CH$_3$, CN, halogen (e.g., Cl, Br, F, etc.), trihalomethane (e.g., CCl$_3$, CBr$_3$, CF$_3$, etc.), OH, NH$_2$, alkyl$_{1-6}$-CH$_3$, alkyl$_{1-6}$-CN, alkyl$_{1-6}$-halogen (e.g., Cl, Br, F, etc.), alkyl$_{1-6}$-trihalomethane (e.g., CCl$_3$, CBr$_3$, CF$_3$, etc.), alkyl$_{1-6}$-OH, or alkyl$_{1-6}$-NH$_2$.

A is CH$_3$, CN, halogen (e.g., Cl, Br, F, etc.), trihalomethane (e.g., CCl$_3$, CBr$_3$, CF$_3$, etc.), OH, NH$_2$, alkyl$_{1-6}$-CH$_3$, alkyl$_{1-6}$-CN, alkyl$_{1-6}$-halogen (e.g., Cl, Br, F, etc.), alkyl$_{1-6}$-trihalomethane (e.g., CCl$_3$, CBr$_3$, CF$_3$, etc.), alkyl$_{1-6}$-OH, alkyl$_{1-6}$-NH$_2$, a carbocycle, a heterocycle, an aryl, a heteroaryl, a multi-ring system thereof, or absent;

Y is C, S, O, or absent;

X is:

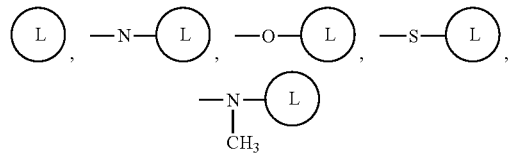

NH-alkyl$_{1-6}$, O-alkyl$_{1-6}$, S-alkyl$_{1-6}$, CH$_2$-alkyl$_{1-6}$, NH-alkyl$_{1-6}$-O-methyl, O-alkyl$_{1-6}$-O-methyl, S-alkyl$_{1-6}$-O-methyl, CH$_2$-alkyl$_{1-6}$-O-methyl, wherein N-dimethyl; and

is any carbocycle, heterocycle, aryl, heteroaryl, or multi-ring systems thereof, and

is optionally substituted at any suitable positions with $CH_3$, CN, halogen (e.g., Cl, Br, F, etc.), trihalomethane (e.g., $CCl_3$, $CBr_3$, $CF_3$, etc.), OH, $NH_2$, $alkyl_{1-6}$-$CH_3$, $alkyl_{1-6}$-CN, $alkyl_{1-6}$-halogen (e.g., Cl, Br, F, etc.), $alkyl_{1-6}$-trihalomethane (e.g., $CCl_3$, $CBr_3$, $CF_3$, etc.), $alkyl_{1-6}$-OH, or $alkyl_{1-6}$-$NH_2$.

In some embodiments, any rings present in Formula (1) (e.g.,

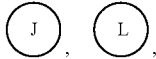

or the central ring system) are optionally substituted at any positions, with one or more functional groups, each independently selected from H, alkyl, substituted alkyl, hydroxy, alkoxy, amine, thioalkyl, halogen, ketone, amide, cyano, sulfonyl, dialkylphosphine oxide, a carbocyclic ring, an aromatic ring, a substituted aromatic ring, a heterocyclic aromatic ring, a substituted heterocyclic aromatic ring, a substituted or non-substituted heterocyclic non-aromatic ring, carbocyclic or heterocyclic aromatic ring fused to another aromatic ring, a hydrogen bond donor, a hydrogen bond acceptor, and combinations thereof.

In some embodiments, G, A, and any optional substituents present on

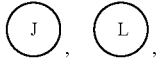

or the central ring system of Formula (1) are selected from: halogen, hydroxy, oxo (=O), thioxo (=S), cyano (—CN), nitro (—$NO_2$), imino (=N—H), oximo (=N—OH), hydrazino (=N—$NH_2$), —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2), and —$R^b$—S(O)$_t$N($R^a$)$_2$ (where t is 1 or 2); and alkyl, alkenyl, alkynyl, each of which may be optionally substituted by halogen, oxo (=O), thioxo (=S), cyano (—CN), nitro (—$NO_2$), imino (=N—H), oximo (=N—OH), hydrazine (=N—$NH_2$), —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2), —$R^b$—S(O)$_t$N($R^a$)$_2$ (where t is 1 or 2), carbocycle and heterocycle; wherein each $R^a$ is independently selected from hydrogen, alkyl, alkenyl, alkynyl, carbocycle and heterocycle, wherein each $R^a$, valence permitting, may be optionally substituted with halogen, oxo (=O), thioxo (=S), cyano (—CN), nitro (—$NO_2$), imino (=N—H), oximo (=N—OH), hydrazine (=N—$NH_2$), —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$R^a$ (where t is 1 or 2), —$R^b$—S(O)$_t$$OR^a$ (where t is 1 or 2) and —$R^b$—S(O)N($R^a$)$_2$ (where t is 1 or 2); and wherein each $R^b$ is independently selected from a direct bond or a straight or branched alkylene, alkenylene, or alkynylene chain, and each $R^c$ is a straight or branched alkylene, alkenylene or alkynylene chain.

In some embodiments, G, A, and any optional substituents present on

or the central ring system of Formula (1) are selected from Substituent groups may be selected from, but are not limited to: alkyl, alkenyl, alkynyl, cycloalkyl, aryl, heteroaryl, heterocycloalkyl, hydroxyl, alkoxy, mercaptyl, cyano, halo, carbonyl, thiocarbonyl, isocyanato, thiocyanato, isothiocyanato, nitro, perhaloalkyl, perfluoroalkyl, and amino, including mono- and di-substituted amino groups, and combinations thereof.

In some embodiments,

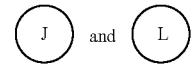

(when present) are independently selected from any carbocycle, non-aromatic carbocycle, cycloalkyl ring, non-aromatic heterocycle, aryl, heteroaryl, or multiring (e.g., 2 rings, 3 rings, etc.) systems thereof. For example, in some embodiments, J and L (when present) are independently selected from: azulenyl, indanyl, indenyl, naphthyl, phenyl, tetrahydronaphthyl, cyclopropyl, cyclobutyl, cyclopentyl, cyclohexyl, cycloheptyl, cyclooctyl, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, and thiopyranopyridine. In some embodiments, such rings and ring systems are optionally substitued at any suitable positions.

In some embodiments,

is a 5-6 member carbocycle (e.g., cyclopentane, cyclohexane, cyclopentene, cyclohexene, 1,3-cyclohexadiene, cyclopentadiene, etc.), non-aromatic carbocycle, cycloalkyl ring, non-aromatic heterocycle (e.g., pyrrolidine, tetrahydrofuran, thiolane, imidazolidine, pyrazolidine, oxazolidine, isoxazolidine, thiazolidine, isothiazolidine, dioxolane, dithiolane, piperdine, oxane, thiane, piperazine, morpholine, thiomorpholine, dioxane, dithiane, trioxane, thrithiane, etc.), aryl (e.g., benzyl), heteroaryl (e.g., furan, pyrrole, thiophene, imidazole, pyrazole, oxazole, isooxazole, thiozole, pyridine, pyrazine, pyrimidine, pyridazine, 1,2,3-trazine, 1,2,4-triazine, 1,3,5-triazine, etc.), or two-ring system thereof (e.g., any suitable combinations of 5-6 member carbocycle, non-aromatic carbocycle, cycloalkyl ring, non-aromatic heterocycle, aryl, and/or heteroaryl).

In some embodiments,

(when present) is a 5-6 member carbocycle (e.g., cyclopentane, cyclohexane, cyclopentene, cyclohexene, 1,3-cyclohexadiene, cyclopentadiene, etc.), non-aromatic carbocycle, cycloalkyl ring, non-aromatic heterocycle (e.g., pyrrolidine, tetrahydrofuran, thiolane, imidazolidine, pyrazolidine, oxazolidine, isoxazolidine, thiazolidine, isothiazolidine, dioxolane, dithiolane, piperdine, oxane, thiane, piperazine, morpholine, thiomorpholine, dioxane, dithiane, trioxane, thrithiane, etc.), aryl (e.g., benzyl), heteroaryl (e.g., furan, pyrrole, thiophene, imidazole, pyrazole, oxazole, isooxazole, thiozole, pyridine, pyrazine, pyrimidine, pyridazine, 1,2,3-trazine, 1,2,4-triazine, 1,3,5-triazine, etc.), or two-ring system thereof (e.g., any suitable combinations of 5-6 member carbocycle, non-aromatic carbocycle, cycloalkyl ring, non-aromatic heterocycle, aryl, and/or heteroaryl).

In some embodiments, when X is not

,

X is OR', —SR', —NHR', —N(R)$_2$, —NR'OR'—N(R')C(O)R', —OC(O)R', —C(O)OR', —C(O)N(R')$_2$, —OC(O)R', —S(O)$_2$R', —S(O)$_2$N(R')$_2$, —N(R)S(O)$_2$R', etc.; wherein R' at each occurrence is independently selected from hydrogen, $C_{1-6}$ alkyl, $C_{2-6}$ alkenyl, and $C_{2-6}$ alkynyl.

In some embodiments, a composition (e.g., pharmaceutical composition) is provided comprising one or the compounds from Table 2 (e.g., NUCC-0176286, NUCC-0176287, NUCC-0176288, NUCC-0176289, NUCC-0176290, NUCC-0176291, NUCC-0176292, NUCC-0176293, NUCC-0176294, NUCC-0176295, NUCC-0176296, NUCC-0176297, NUCC-0176298, NUCC-0176299, NUCC-0176300, NUCC-0176301, NUCC-0176302, NUCC-0176303, NUCC-0176304, NUCC-0176305, NUCC-0176306, NUCC-0176307, NUCC-0176308, NUCC-0176309, NUCC-0176310, NUCC-0176311, NUCC-0176312, NUCC-0176313, NUCC-0176314, NUCC-0176315, NUCC-0176316, NUCC-0176317, NUCC-0176318, NUCC-0176319, NUCC-0196315, NUCC-0196316, NUCC-0196317, NUCC-0196318, NUCC-0196319, NUCC-0196320, NUCC-0196321, NUCC-0196322, NUCC-0196323, NUCC-0196324, NUCC-0196325, NUCC-0196326, NUCC-0196327, NUCC-0196328, NUCC-0196329, NUCC-0196330, NUCC-0196331, NUCC-0196332, NUCC-0196333, NUCC-0196334, NUCC-0196335, NUCC-0196336, NUCC-0196337, NUCC-0196338, and NUCC-0196339). In some embodiments, a compound is provided having the structure of Formula (1):

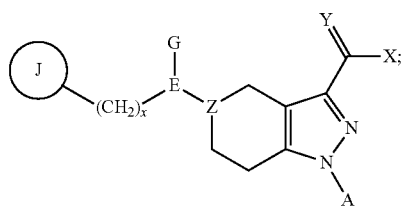

Wherein J, y, E, G, Z, A, Y, and X are selected from the substituents and functional groups of the compounds depicted in Table 2 (e.g., recombined in any suitable combination).

In some embodiments, the compounds described herein find use in the treatment or prevention of disease, and/or the alleviation of symptoms associated therewith. In some embodiments, the compounds herein find use in the treatment of cancer (e.g., breast cancer, ovarian cancer, melanoma, prostate cancer, or metastasis thereof). In some embodiments, pharmaceutical compositions comprising a compound herein are administered to a subject to treat a disease of condition (e.g., cancer).

In some embodiments, provided herein are pharmaceutical compositions comprising a therapeutic agent (e.g., CXCR4 antagonist, CXCR4 agonist, etc.), alone or in combination with at least one other non-therapeutic agent, such as a stabilizing compound, and may be administered in any sterile, biocompatible pharmaceutical carrier, including, but not limited to, saline, buffered saline, dextrose, and water.

As is well known in the medical arts, dosages for any one patient depends upon many factors, including the patient's size, body surface area, age, the particular compound to be administered, sex, time and route of administration, general health, and interaction with other drugs being concurrently administered.

Pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, pharmaceutical compositions may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions are formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions include compositions wherein the active ingredients (e.g., ., CXCR4 antagonist, CXCR4 agonist, etc.) are contained in an effective amount to achieve the intended purpose. Determination of effective amounts is well within the capability of those skilled in the art, especially in light of the disclosure provided herein.

In addition to the active therapeutic ingredients, pharmaceutical compositions may contain suitable pharmaceutically acceptable carriers comprising excipients and auxiliaries that facilitate processing of the active compounds into preparations that can be used pharmaceutically. The preparations formulated for oral administration may be in the form of tablets, dragees, capsules, or solutions. The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (e.g., dosage).

Pharmaceutical preparations for oral administration include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Therapeutic compositions formulated in a pharmaceutical acceptable carrier may be prepared, placed in an appropriate container, and labeled for treatment of the indicated condition.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder, for example, in 1 mM-50 mM histidine, 0.1%-2% sucrose, 2%-7% mannitol at a pH range of 4.5 to 5.5 that is combined with buffer prior to use.

In some embodiments, a therapeutically effective dose may be estimated initially from cell culture assays and/or animal models (particularly murine models). A therapeutically effective dose refers to that amount that effectively addresses and underlying cause and/or ameliorates symptoms of the disease state or unwanted condition. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. Data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration. The exact dosage is chosen by the individual clinician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination (s), reaction sensitivities, and tolerance/response to therapy. Long acting pharmaceutical compositions might be administered every 3 to 4 days, every week, or once every two weeks depending on half-life and clearance rate of the particular formulation.

Typical dosage amounts may vary from 0.1 to 100,000 micrograms, up to a total dose of about 1 g, depending upon the route of administration. Guidance as to particular dosages and methods of delivery is provided in the literature (See, U.S. Pat. Nos. 4,657,760; 5,206,344; 5,225,212; WO2004/097009, or WO2005/075465, each of which are herein incorporated by reference).

In some embodiments, the therapies disclosed herein are combined or used in combination with other agents useful in the treatment of a disease or condition. Or, by way of example only, the therapeutic effectiveness of one of the therapies described herein may be enhanced by administration of an adjuvant (e.g., by itself the adjuvant may only have minimal therapeutic benefit, but in combination with another therapeutic agent, the overall therapeutic benefit to the patient is enhanced).

Such other agents, adjuvants, or drugs, may be administered, by a route and in an amount commonly used therefor, simultaneously or sequentially with a compound as disclosed herein. When a compound as disclosed herein is used contemporaneously with one or more other drugs, a pharmaceutical composition containing such other drugs in addition to the compound disclosed herein may be utilized, but is not required.

In some embodiments, one or more of the therapies provided herein (e.g., CXCR4 antagonist, CXCR4 agonist, etc.) are combined with each other, and/or with one or more other therapeutics or therapies. In some embodiments, one or more therapeutic approaches are co-administered to a subject. In some embodiments, co-administration involves co-formulation of two or more agents together into the same medicament. In other embodiments, the agents are in separate formulations but are administered together, either simultaneously or in sequence (e.g., separated by one or more minutes, hours, days, etc.). In some embodiments, where a synergistic or additive benefit is achieved, the co-administered agent may be provided at a lower dose than would normally be administered if that agent were being used in isolation to treat the disease or condition.

The technology provided herein also includes kits for use in the instant methods. Kits of the technology comprise one or more containers comprising a therapeutic approach described herein and/or a second agent, and in some variations further comprise instructions for use in accordance with any of the methods provided herein. The kit may further comprise a description of selecting an individual suitable treatment. Instructions supplied in the kits of the technology are typically written instructions on a label or package insert (e.g., a paper insert included with the kit), but machine-readable instructions (e.g., instructions carried on a magnetic or optical storage disk) are also contemplated. In some embodiments, the kit is a package containing a sealed container comprising any one of the preparations described above, together with instructions for use. The kit can also include a diluent container containing a pharmaceutically acceptable diluent. The kit can further comprise instructions for mixing the preparation and the diluent. The diluent can be any pharmaceutically acceptable diluent. Well known diluents include 5% dextrose solution and physiological saline solution. The container can be an infusion bag, a sealed bottle, a vial, a vial with a septum, an ampoule, an ampoule with a septum, an infusion bag, or a syringe. The containers can optionally include indicia indicating that the containers have been autoclaved or otherwise subjected to sterilization techniques. The kit can include instructions for administering the various solutions contained in the containers to subjects.

In some embodiments, kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from a variety of materials such as glass or plastic. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment.

The examples and preparations provided below further illustrate and exemplify the compounds of the present invention and methods of preparing such compounds. It is to be understood that the scope of the present invention is not limited in any way by the scope of the following examples and preparations.

EXPERIMENTAL

Exemplary compounds have been obtained, screened, designed, synthesized, and/or tested for biological activity (Table 2 (Example 9), Example 10). Both ligand- (Example 1) and structure-based (Example 3) in silico screening approaches were used to identify receptor-binding molecules without bias towards known antagonists. The dual approach recognizes that the CXCR4 ligand-binding site is quite large,(ref. 4; herein incorporated by reference in its entirety) and so it is difficult to accurately predict the precise ligand binding mode using flexible ligand docking. Biological activity of compounds was determined in a variety of assays, including calcium imaging (Example 5), ERK activation (Example 6), internalization of CXCR4 receptor (Example 7), and mediation of chemotaxis (Example 8).

Example 1

Ligand-based Virtual Screen

Annotated Database Creation

The Chembridge GPCR-focused library containing ~13,000 compounds was used as the database for a ligand-based screen. To generate the low energy conformers, the ConFirm/CatConf module from Accelrys was used in "best" mode.(ref. 7; herein incorporated by reference in its entirety) To refine the conformers, a modified version of the CHARMm force field (ref. 12; herein incorporated by reference in its entirety) was used along with a poling technique (ref. 13; herein incorporated by reference in its entirety) that biased the sampling of conformations towards geometries that were far from a local minimum but energetically near each other.(ref. 14; herein incorporated by reference in its entirety) This method generated ~100 conformers of each compound within an energy cutoff of 10 kcal/mol.

Example 2

Common-feature Pharmacophore Model Building and Compound Database Screening.

Surveying ChEMBL (version 13), 162 CXCR4 antagonists were selected that were reported to have IC50 values in the range of 1 nM to 10 µM. Using cluster analysis protocols implemented in Discovery Studio,(ref. 7b; herein incorporated by reference in its entirety) the compounds were grouped into 5 different clusters. Since these 162 antagonists had been evaluated using different assay conditions from multiple laboratories, it was inappropriate to apply activity-based techniques. After clustering, 2 molecules were selected from each cluster to build a training set. The common feature pharmacophore modeling tool implemented in Discovery Studio (ref. 7a; herein incorporated by reference in its entirety) was then applied to build a set of 10 pharmacophores, called "hypotheses", using the training set of compounds. The default set of parameters were used to build the hypotheses. Another 2 molecules from each of the 5 clusters were then selected (10 molecules total) to make a test set. All 10 hypotheses were tested with the test set and one 5-point pharmacophore model was found to fit well to all 10 compounds of the test set. This hypothesis consisted of two hydrophobic (Hy), two Hydrogen Bond Acceptor (HBA), and one Positive Ionizable (PI) feature (FIG. 1). Each of the pharmacophoric features was assigned a weight value of 1, providing a fit value of 100% for a molecule that matched all 5 features. This pharmacophore model was selected for screening the annotated GPCR compound database. Database screening produced 26 structures with >85% fit values along with conformational energy less than 5 kcal/mol.

Based on availability and synthetic tractability, 6 compounds were selected to be purchased from this ligand-based hit set. Mapping of the selected pharmacophore with one of the eventual hits (NUCC-390) is shown in FIG. 1.

Example 3

Structure-based Virtual Screen

Analyzing the CXCR4 crystal structures (accession codes 3ODU and 3OEo),(ref.4; herein incorporated by reference in its entirety) the 16-residue cyclic peptide was observed filling a large ligand binding site, whereas the small molecule IT1t only occupies a small part of the pocket. To obtain consensus binding poses with flexible ligand docking tools, two docking engines we selected built upon orthogonal algorithms. The Surflex docking engine implemented in the Sybyl interface of Tripos (ref. 8; herein incorporated by reference in its entirety) and the Glide docking tool of Schrodinger (ref. 9; herein incorporated by reference in its entirety) were both used as they have been found to be superior both in pose prediction and virtual screening of compound databases.(ref. 10; herein incorporated by reference in its entirety) The Surflex docking engine is built upon a fragment-based algorithm whereas the Glide docking tool is built on a grid-based technique. Since a database of GPCR-focused molecules was considered, we carried out the docking using both Surflex and Glide docking engines. To prepare the protein for the docking experiments, the small-molecule bound CXCR4 crystal structure (pdb code 3ODU) was subjected to Prime (Schrodinger) validation (ref. 11; herein incorporated by reference in its entirety) to correct for irrelevant side chains, missing atoms, undesired orientation of Asn, Gln or His residues, to replace the b-values by the OPLS charges, and to fix the protonation states of the residues at physiological pH. Next, the 'Prot-Prep' module was used to prepare and refine the cocrystal structure to generate the receptor (protein) and the bound ligand. A 12 Å grid box was generated using the centroid of the bound ligand to prepare for Glide docking.

For Surflex docking, the ligand (IT1t) was extracted from the co-crystal structure and the protein was subjected to the protein preparation panel in the Sybyl interface. In this panel, hydrogens were added in hydrogen bonding orientation, b-values were replaced by the Gasteiger charges, irrelevant torsions were eliminated, and the protonation states of the residues were fixed at pH 7.4. A ligand-based protomol was generated in the active site which represented the template for an ideal active-site ligand.

Example 4

Docking Engines

First, the 20 reported antagonists (Training and Test sets, see above) were docked using the Glide-XP module with the standard sampling mode of maxkeep=5000 and maxref=400. The van der Waals radii for nonpolar ligand atoms were scaled to 0.8. After docking, the docked poses of the 20 compounds were analyzed and the interactions of the antagonists with the different residues were noted. As these compounds were of different chemotypes, they showed different binding poses interacting with different residues. The Lig-Prep module of the Schrodinger suite was utilized to prepare the GPCR—focused library for docking. Using the same docking protocols as described above, the library compounds were docked into the ligand-binding site of CXCR4. Compounds showing a Glide score of <−6.0 were considered for further analysis.(ref.9; herein incorporated by reference in its entirety) The interacting residues identified from the known antagonist set guided our analysis of the docked poses of the unknown compounds from library. Based on the docked scores and the interactions with critical residues, 52 compounds from this set were selected as in silico hits.

A similar approach for this docking experiment was carried out using the Surflex docking tool implemented in Sybly interface. At first the 20 antagonists set were docked in the earlier-defined ligand-binding site of CXCR4. The default set of run time parameters had been used along with the GeomX docking mode, which generated the best docking pose of the ligands. After docking the known antagonists, the docked poses we analyzed and the critical interacting residues of the CXCR4 active site were identified. The GPCR ligand set was prepared using the ligand preparation panel implemented in the Sybyl interface. Using similar docking protocols, the library was docked and 48 compounds showed good interactions with active site residues and had a total score >6.0. Total score is a function of −logKd.

Figure 2:
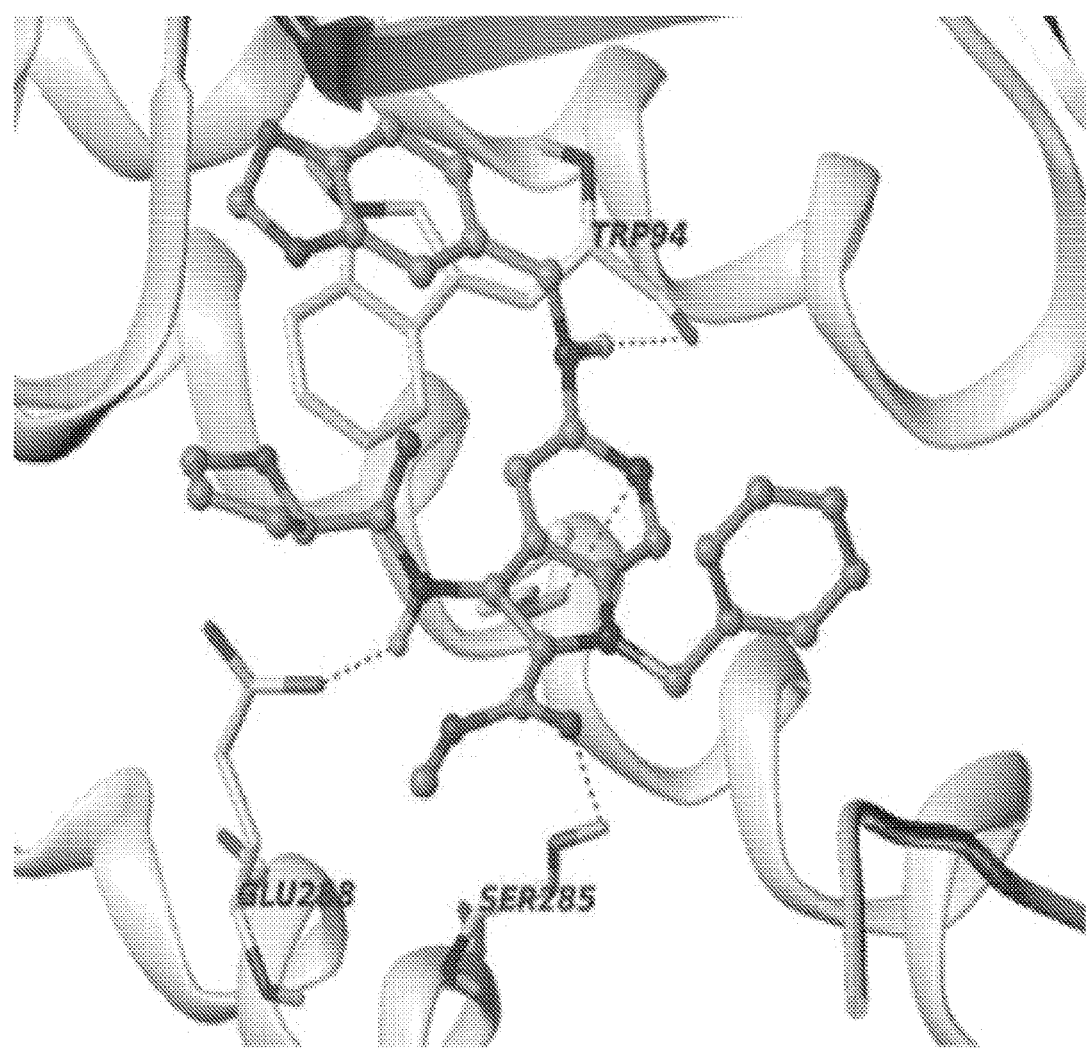
FIG. 2. Docked pose of NUCC-397 in the CXCR4 crystal structure. Dotted lines show putative hydrogen bonds.

22 compounds were identified showing similar binding poses and favorable interactions with the active site residues from the Glide and Surflex docking experiments. These in silico hits underwent further evaluation for their presence of potentially toxic or metabolically unstable groups, reactive functional groups, non-drug like features, synthetic feasibility, structural diversity, and commercial availability. Based on these criteria, 9 of these structure-based virtual hits were obtained. The docked pose of NUCC-388 along with the interacting residues is shown in FIG. 2.

Example 5

Calcium Imaging Assay

Figure 3:
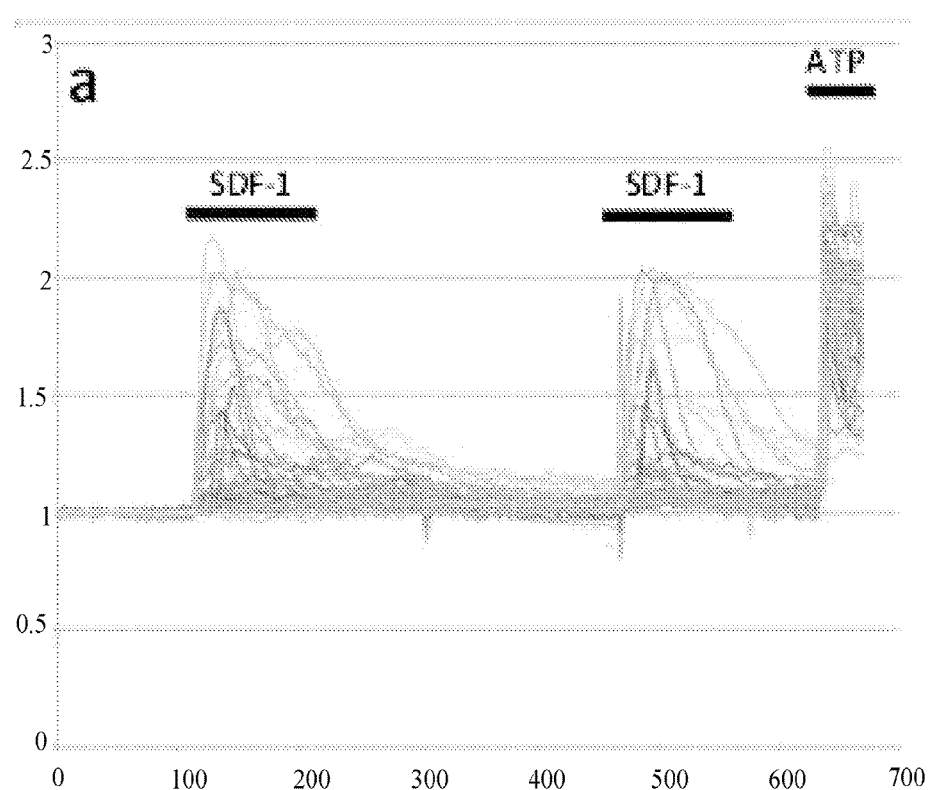
FIG. 3. (Ca)i mobilization assay using CXCR4 expressing C8161 melanoma cells. Each colored line represents the response of a different single cell (A) Control using endogenous CXCR4 agonist SDF-1 (100 nM) shows two strong (Ca)i responses. Addition of ATP (10 μM) to activate purinergic receptors was performed as a positive control for cell viability (B) Antagonist NUCC-388 (10 μM) blocks the effect of SDF-1. (C) Agonist NUCC-390 (10 μM) produces strong (Ca)i response which is blocked by the known potent and selective CXCR4 antagonist AMD3100 (1 μM). (D) Agonist effects of NUCC-398 (10 μM). (E) Comparison of the effects of SDF-1 and NUCC-390 averaged over 74 cells.
Figure 3:
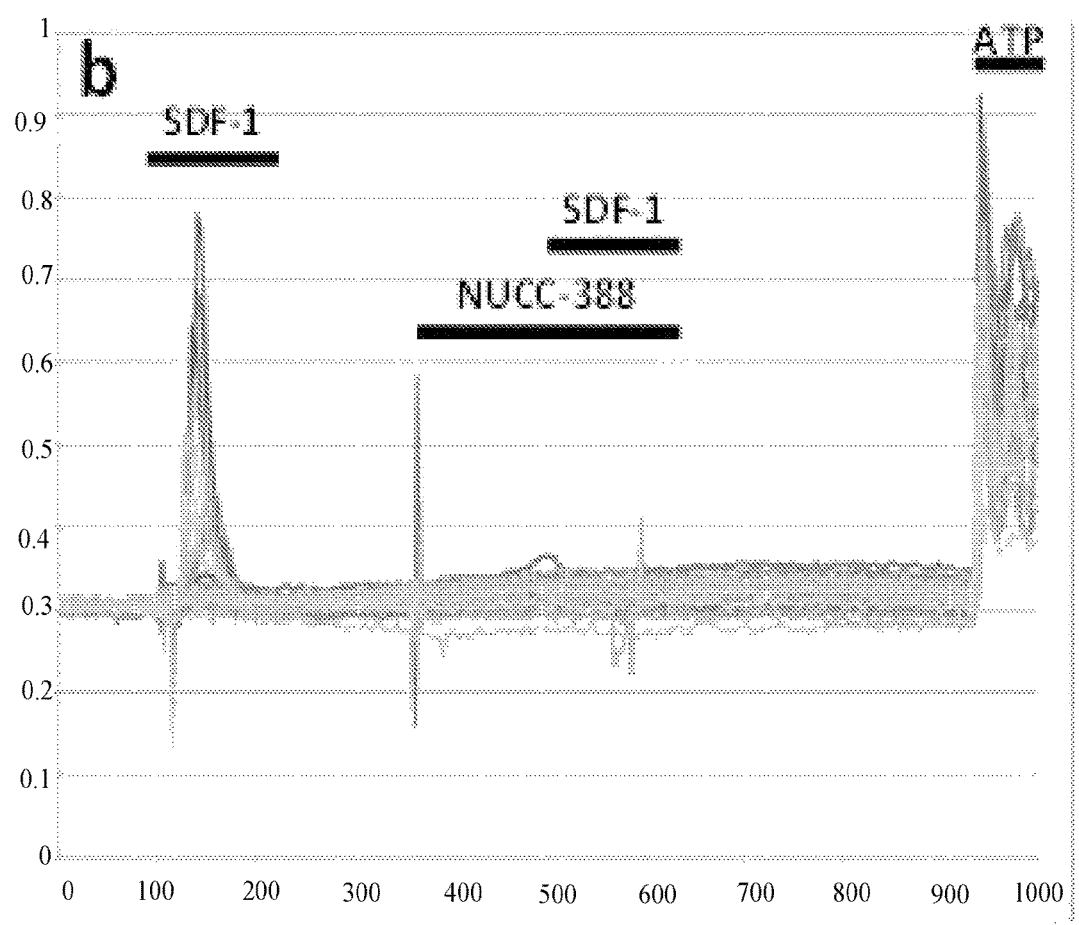
Figure 3:
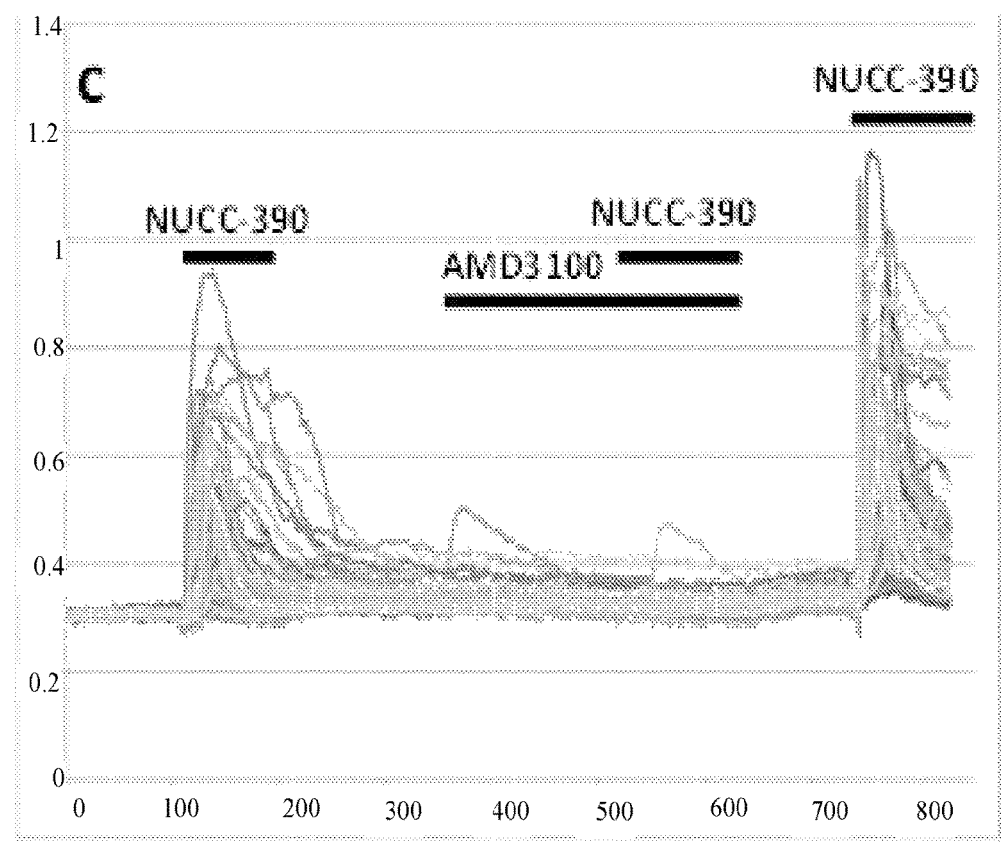
Figure 3:
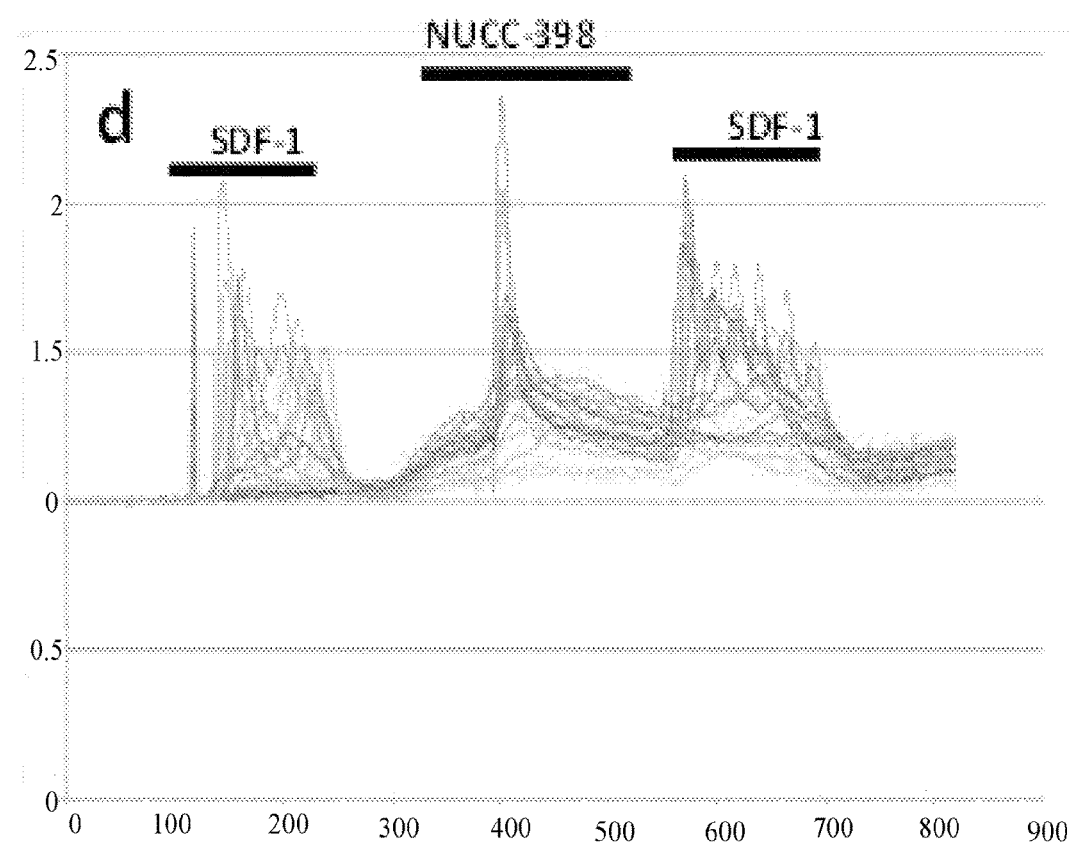
Figure 3:
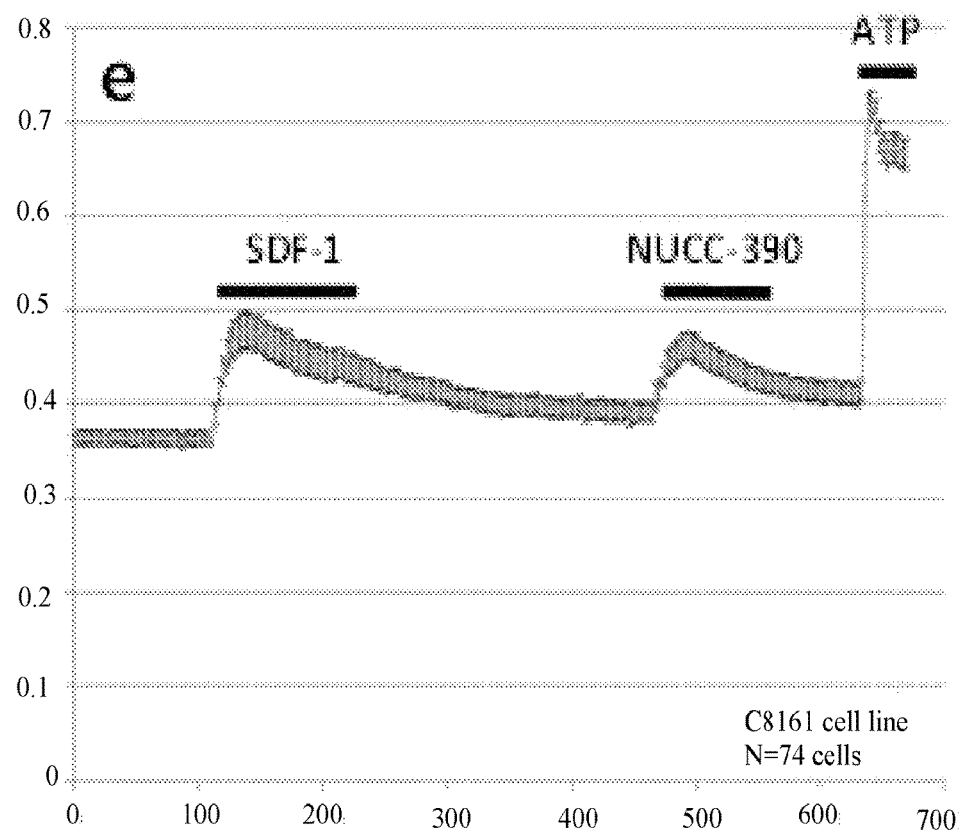

The initial assay for examining the activity of different molecules was based on the fact that activation of CXCR4 receptors produces an increase in the intracellular free $Ca^{2+}$ concentration (Ca)i. This signal can easily be observed using a fluorescent $Ca^{2+}$ sensing dye such as fura-2. The quantitative nature of this assay makes it ideal for screening purposes. Moreover, the assay can also distinguish potential antagonists from potential agonists. The aggressive human melanoma cell line C8161 was initially used, which expresses numerous human CXCR4 receptors and produces strong (Ca)I signals when stimulated with SDF-1 (FIG. 3). In the assay, cells were usually stimulated twice with SDF-1. As can be observed in FIG. 3A (control), this resulted in two (Ca)i responses of similar magnitude indicating that when applied acutely in this manner little desensitization was noted. To test a drug, the compound in question was usually added prior to the second stimulation with SDF-1. At this point it was possible to observe whether the compound itself acted as an agonist by giving its own response or if it reduced the magnitude of the second response to SDF-1. The 15 vHTS hits were assayed at an initial single screening concentration of 10 μM and several compounds showed significant biological activity. Some of the compounds such NUCC-388 (FIG. 3B), 392, 397, and 54120 antagonized the effects of SDF-1. Each of the four antagonists were then assayed at multiple concentrations to obtain a dose-response relationship and an estimated IC50. Antagonists NUCC-388, 397, 392, and 51420 had IC50 values of 0.3 μM, 3 μM, 1 μM, and 1 μM respectively.

TABLE 1

Structures and calcium imaging behavior of CXCR$_4$ modulators. Compounds 54118, 54120, 54121, and 54127 were close analogs of NUCC-390 that were purchased for follow-up testing after our initial vHTS Ca assay identified the initial hits. ACS Paraαc

| ID | Structure | Ca$^{2+}$ Assay |
|---|---|---|
| NUCC-388 | 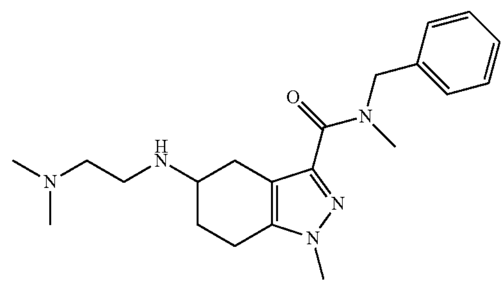 [SMILES: CN(C)CCNC1CCc2c(c(C(=O)N(C)Cc3ccccc3)nn2C)C1] | Antagonist |
| NUCC-390 | 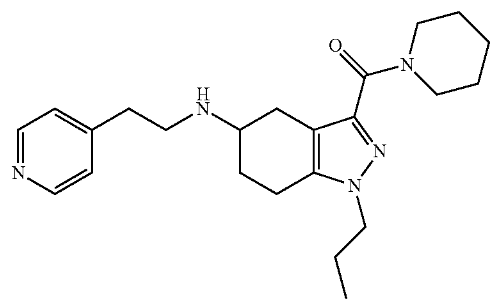 [SMILES: CCCn1nc(C(=O)N2CCCCC2)c2c1CCC(NCCc1ccncc1)C2] | Agonist |
| NUCC-392 | 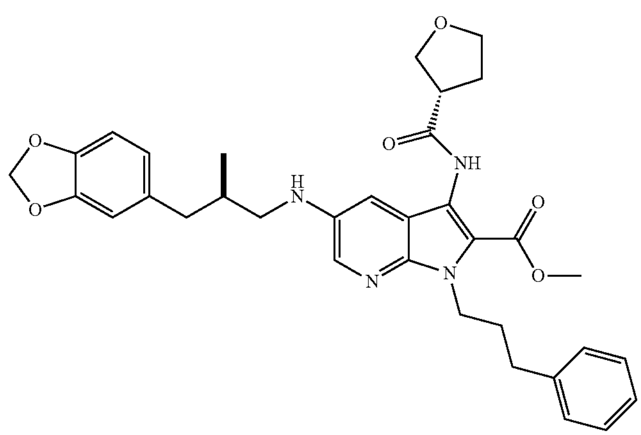 [SMILES: COC(=O)c1c(NC(=O)[C@H]2CCOC2)c2cc(NC[C@H](C)Cc3ccc4c(c3)OCO4)cnc2n1CCCc1ccccc1] | Antagonist |

TABLE 1-continued

Structures and calcium imaging behavior of
CXCR$_4$ modulators. Compounds 54118, 54120, 54121, and
54127 were close analogs of NUCC-390 that were
purchased for follow-up testing after our initial vHTS Ca
assay identified the initial hits. ACS Paraαc

| ID | Structure | Ca$^{2+}$ Assay |
|---|---|---|
| NUCC-397 | 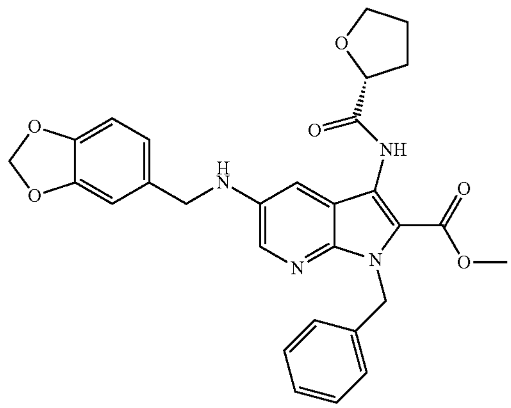 [SMILES: COC(=O)c1c(NC(=O)[C@H]2CCCO2)c2cc(NCc3ccc4c(c3)OCO4)cnc2n1Cc1ccccc1] | Antagonist |
| NUCC-398 | 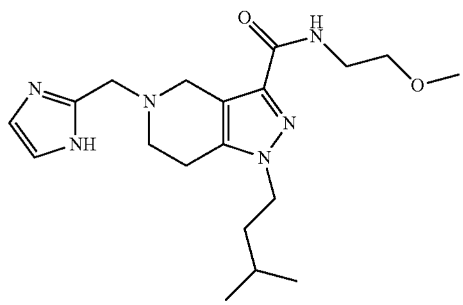 [SMILES: COCCNC(=O)c1nn(CCC(C)C)c2c1CN(Cc1ncc[nH]1)CC2] | Agonist |
| NUCC-54118 | 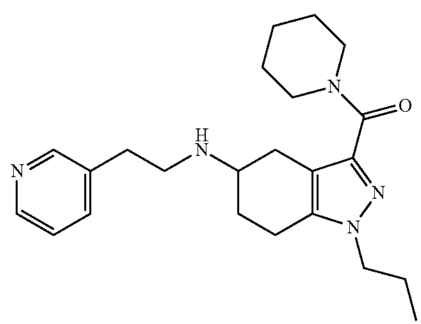 [SMILES: CCCn1nc(C(=O)N2CCCCC2)c2c1CCC(NCCc1cccnc1)C2] | Antagonist |
| NUCC-54120 | 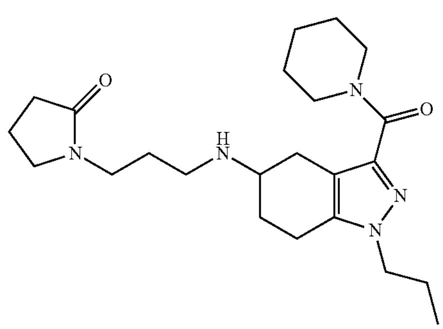 [SMILES: CCCn1nc(C(=O)N2CCCCC2)c2c1CCC(NCCCN1CCCC1=O)C2] | Agonist |

TABLE 1-continued

Structures and calcium imaging behavior of
CXCR4 modulators. Compounds 54118, 54120, 54121, and
54127 were close analogs of NUCC-390 that were
purchased for follow-up testing after our initial vHTS Ca
assay identified the initial hits. ACS Paraαc

| ID | Structure | Ca$^{2+}$ Assay |
|---|---|---|
| NUCC-54121 | 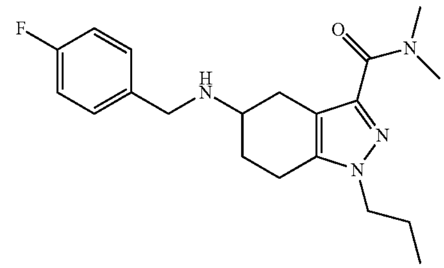 [SMILES: CCCn1nc(C(=O)N(C)C)c2c1CCC(NCc1ccc(F)cc1)C2] | Agonist |
| NUCC-54127 | 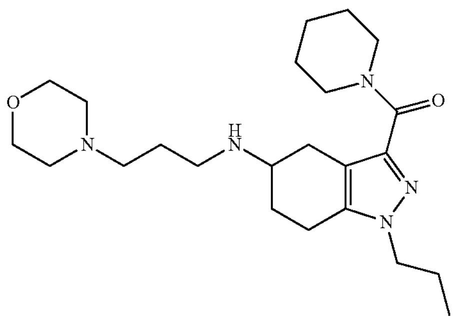 [SMILES: CCCn1nc(C(=O)N2CCCCC2)c2c1CCC(NCCCN1CCOCC1)C2] | Agonist |

Several other molecules displayed clear agonist activity. For example, compound NUCC-390 (FIG. 3C) exhibited effects were similar to those produced by SDF-1. The effects of NUCC-390 were clearly mediated by activation of CXCR4 receptors as they were inhibited by both AMD3100 (a highly-selective CXCR4 antagonist, FIG. 3C) and NUCC-388 which both also blocked the effects of SDF-1. Several other molecules in this series including NUCC-398 (FIG. 3D), 54118, 54121, and 54127 all displayed robust agonist activity when tested on C8161 cells. In each case this stimulation was demonstrated to be inhibited by AMD3100. Averaging data collected over a large number of cells demonstrated that the kinetics of the responses to SDF-1 and NUCC-390 were similar (FIG. 3E).

Example 6

ERK Activation by Agonist NUCC-390

Figure 4:
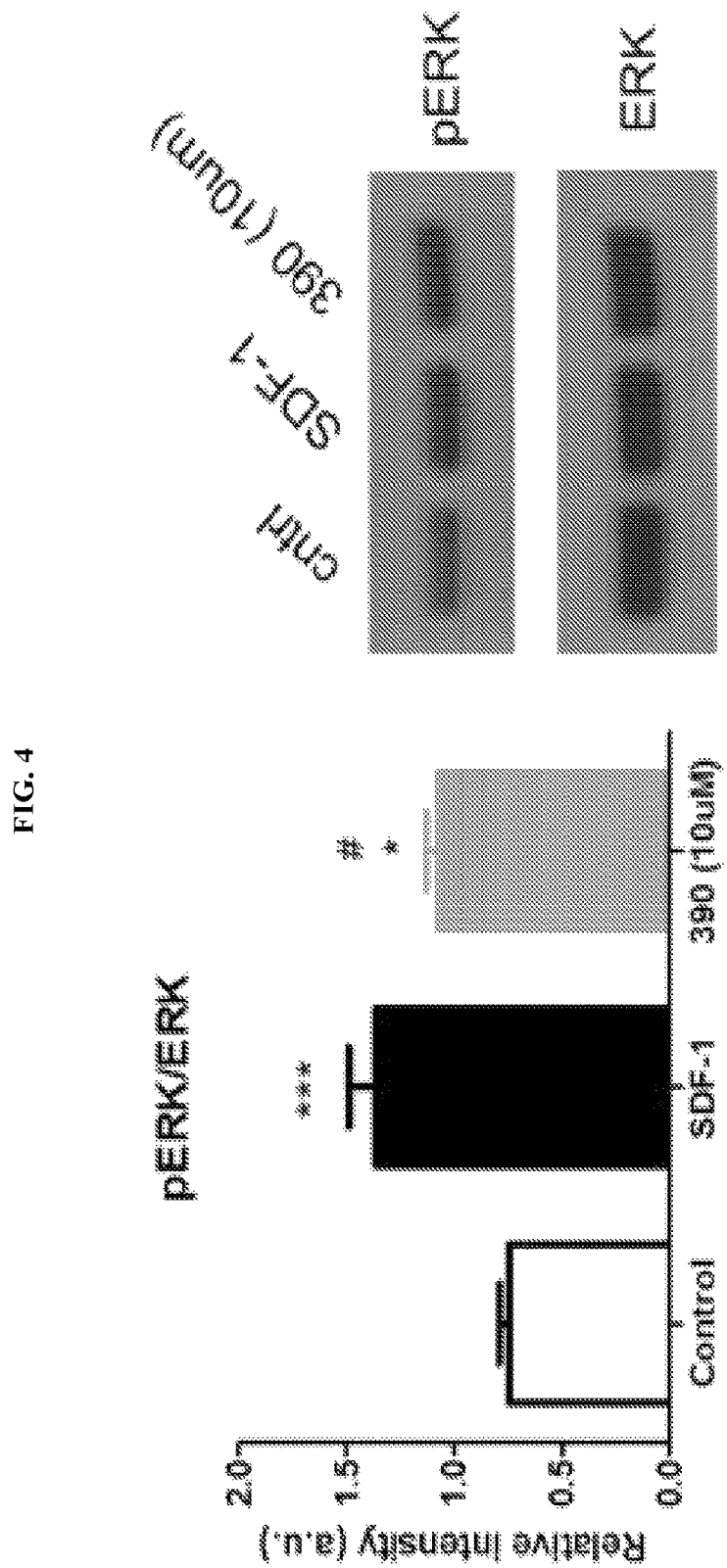
FIG. 4. Increase in pERK produced by SDF-1 (100 nM) and NUCC-390 (10 μM) in CXCR4 expressing C8161 cells. *** $p<0.001$, * $p<0.05$. # Different from the effect of SDF-1, $p<0.05$, n=6.

To further explore the agonist potential of compound NUCC-390, changes in signaling downstream of CXCR4 were examined. For these experiments, lysates were collected from treated C8161 cells and analyzed them using Western blot. Activation of the CXCR4 receptor has been shown to indirectly mediate phosphorylation of ERK,(ref. 12; herein incorporated by reference in its entirety) a key signaling molecule in the MAP kinase pathway. As expected, it was observed that cells treated with SDF-1 for 30 min. displayed increased levels of phosphorylated ERK (pERK). Ttreatment with drug NUCC-390 also led to increased levels of pERK (FIG. 4). That drug NUCC-390 has the capability of stimulating signaling activity downstream of CXCR4 receptors further supports the observation that NUCC-390 acts as a CXCR4 agonist.

Example 7

NUCC-390 Induces Internalization of CXCR4 Receptors.

Figure 5:
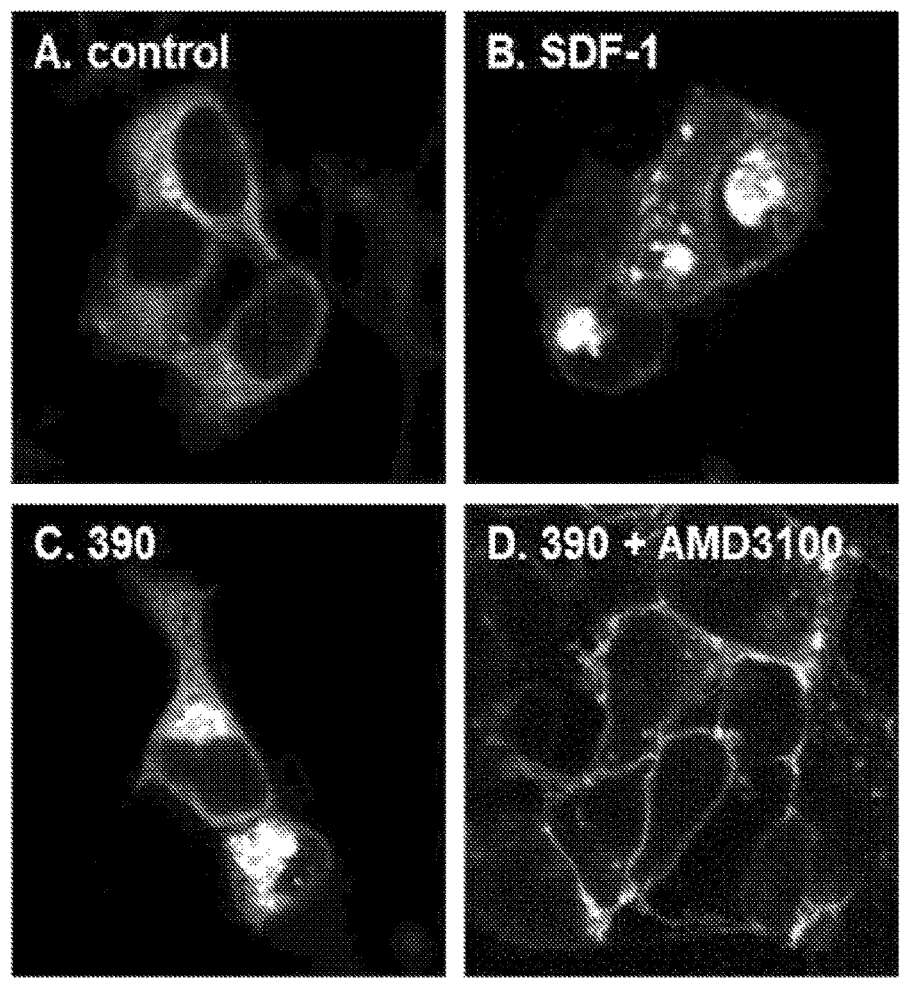
FIG. 5. CXCR4-YFP transfected HEK293 cells treated with agonist 390. (A) CXCR4-YFP transfected cells show normal CXCR4 expression in the cell membrane. Pretreatment with agonist SDF-1 (100 nM) (B) or NUCC-390 (10 μM) (C) for 2 hours causes most of the CXCR4 receptor to become internalized inside cell vesicles. (D) Selective CXCR4 antagonist AMD3100 (1 μM) blocks internalization of agonist NUCC-390.
Figure 5:
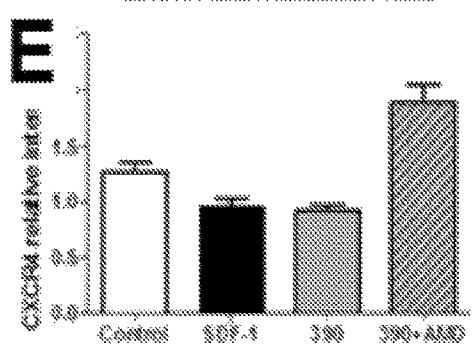
Figure 5:
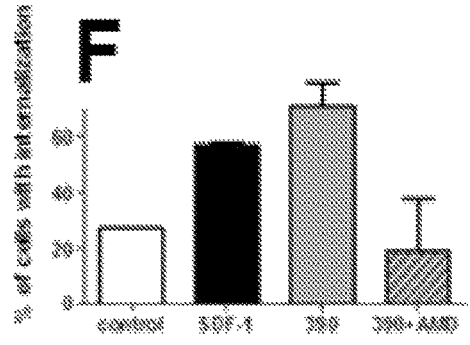

Another characteristic feature of CXCR4 receptors and many other GPCRs is receptor internalization following agonist stimulation.(ref. 13; herein incorporated by reference in its entirety) In order to determine if NUCC-390 exhibited the ability to induce CXCR4 receptor internalization, the cellular localization of YFP-tagged CXCR4 receptors expressed in HEK293 cells was assessed following treatment with SDF-1 or NUCC-390. Non-treated cells showed some diffuse expression of CXCR4-YFP throughout the cytosol and clear expression in the cell membrane (FIG. 5). Treatment with SDF-1 for a period of 2 hours led to pronounced internalization of CXCR4-YFP, producing noticeable aggregates of the receptors in the cytosol but excluded from the nucleus. Similar effects were produced by NUCC-390. The effects of NUCC-390 were completely inhibited by AMD-3100 (FIG. 5D) or NUCC-380. Interestingly, following antagonist treatment virtually all of the CXCR4-YFP was localized in the cell membrane. This indicates some constitutive activity of the receptor and inverse agonist activity for both AMD-3100 and NUCC-390.(ref. 14; herein incorporated by reference in its entirety)

Example 8

SDF-1 and NUCC-390 Mediate Chemotaxis

Figure 6:
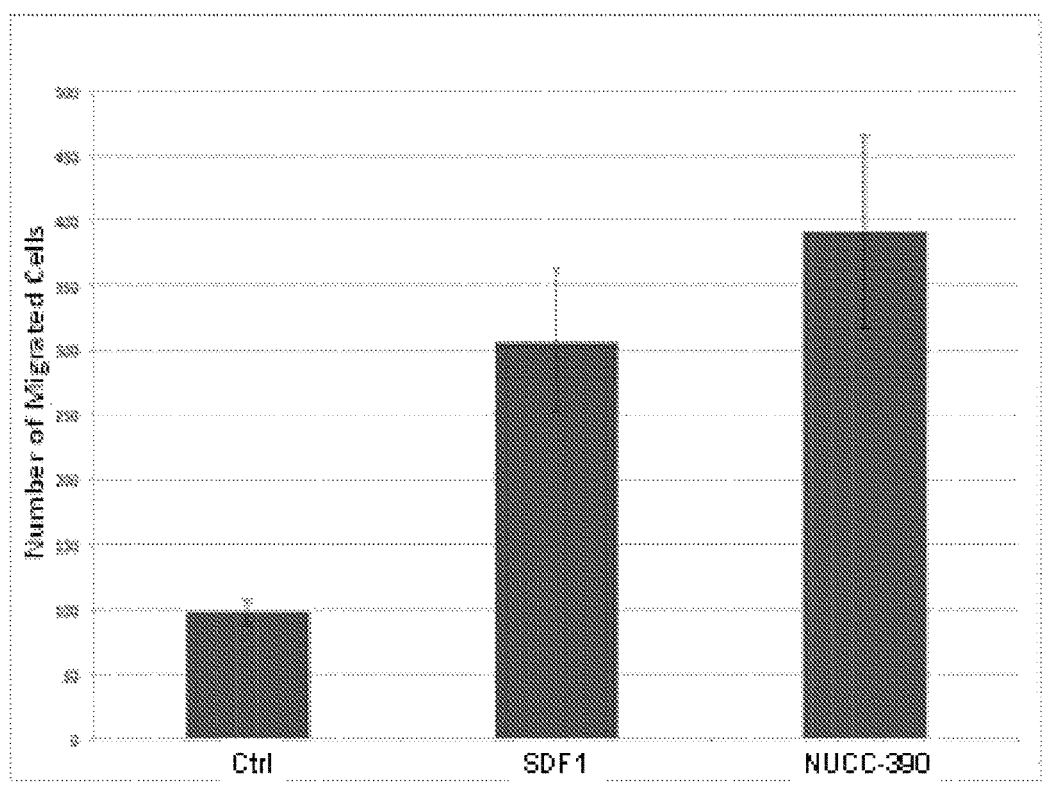
FIG. 6. Chemotaxis produced by SDF-1 (100 nM) or NUCC-390 (10 μM) using C8161 cells in a Boyden chamber. Both SDF-1 and NUCC-390 produced significant effects (p<0.01, n=6).
Figure 7:
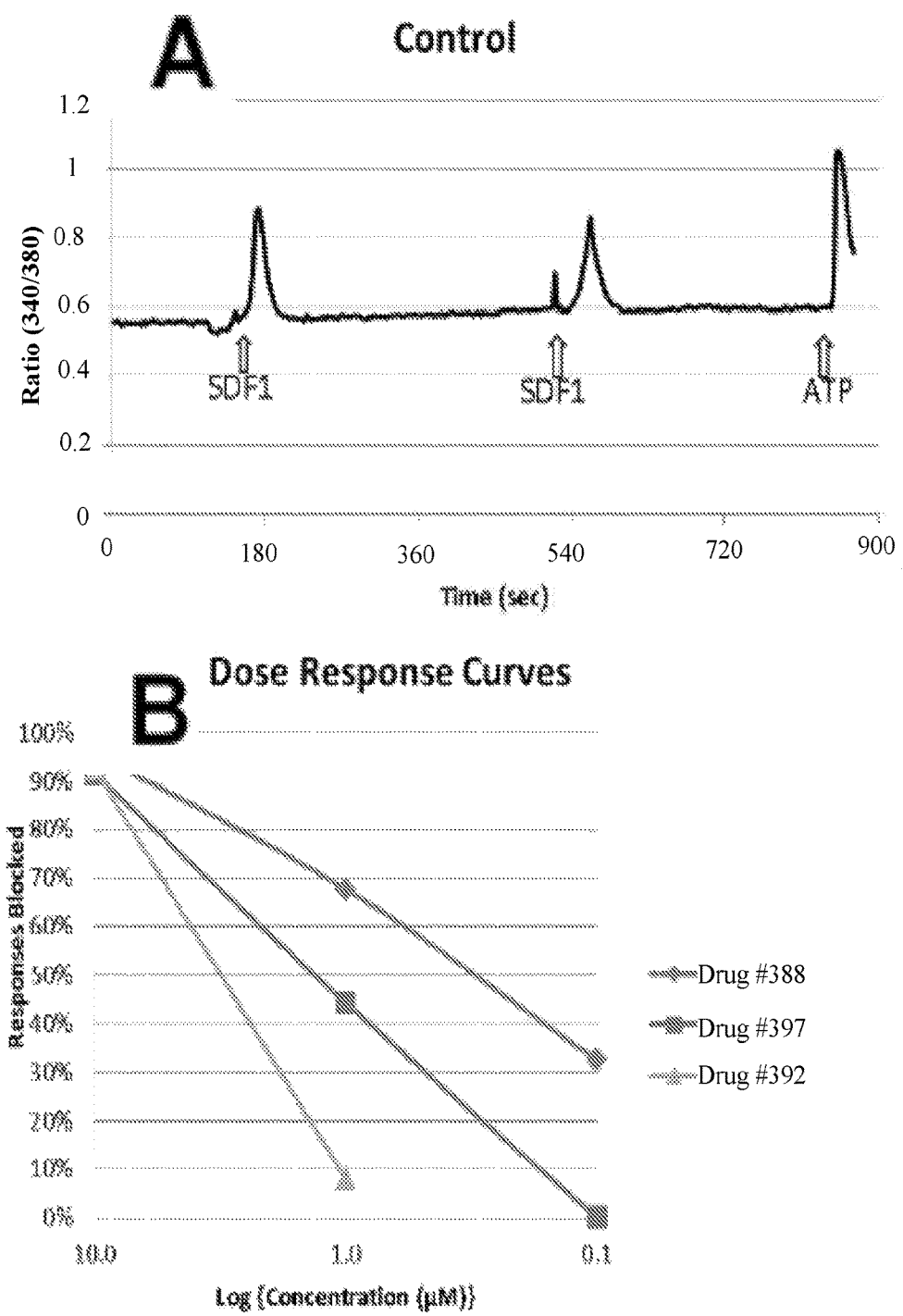
FIG. 7. Effects of exemplary compounds in the (ca)I assay using C8161 melanoma cells. (A) The effect of two additions of SDF-1 producing responses of similar magnitude. (C) NUCC-388 addition (10 μM) completely inhibited the second addition of SDF-1, demonstrating its CXCR4 antagonist effects. (B) Dose response relationships for three exemplary compounds with antagonist activity. (D) NUCC-390 (10 μM) produced agonist effects that were completely blocked by AMD3100, demonstrating that NUCC-390 is a CXCR4 agonist.
Figure 7:
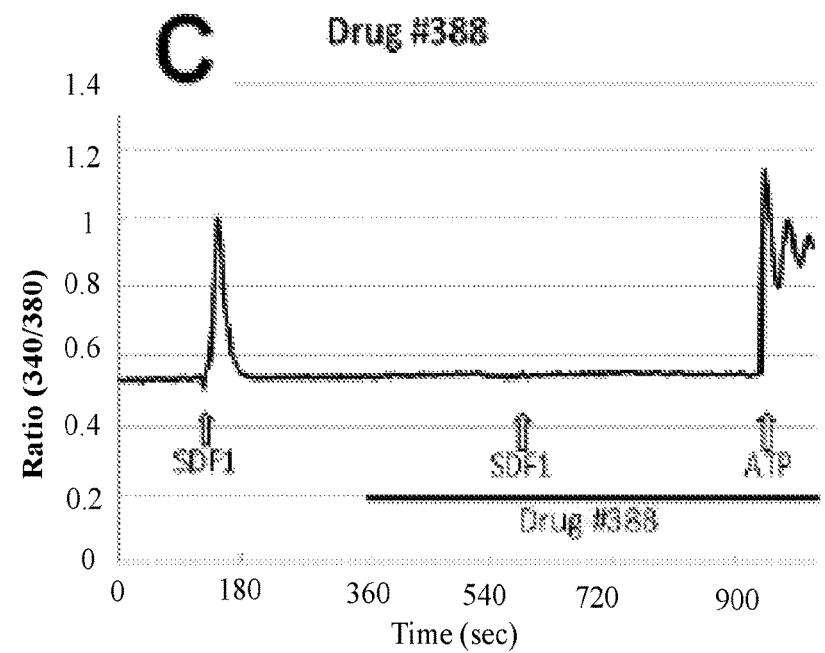
Figure 7:
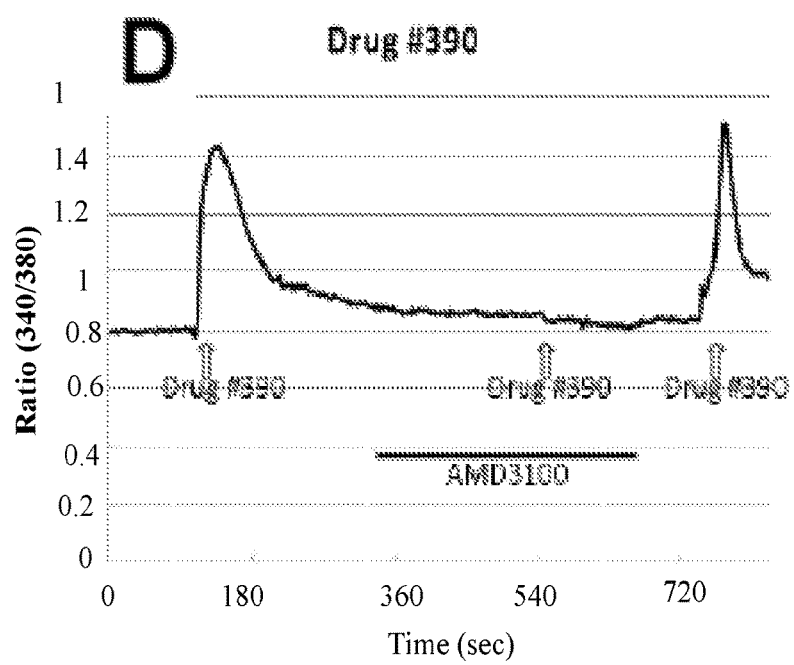
Figure 8:
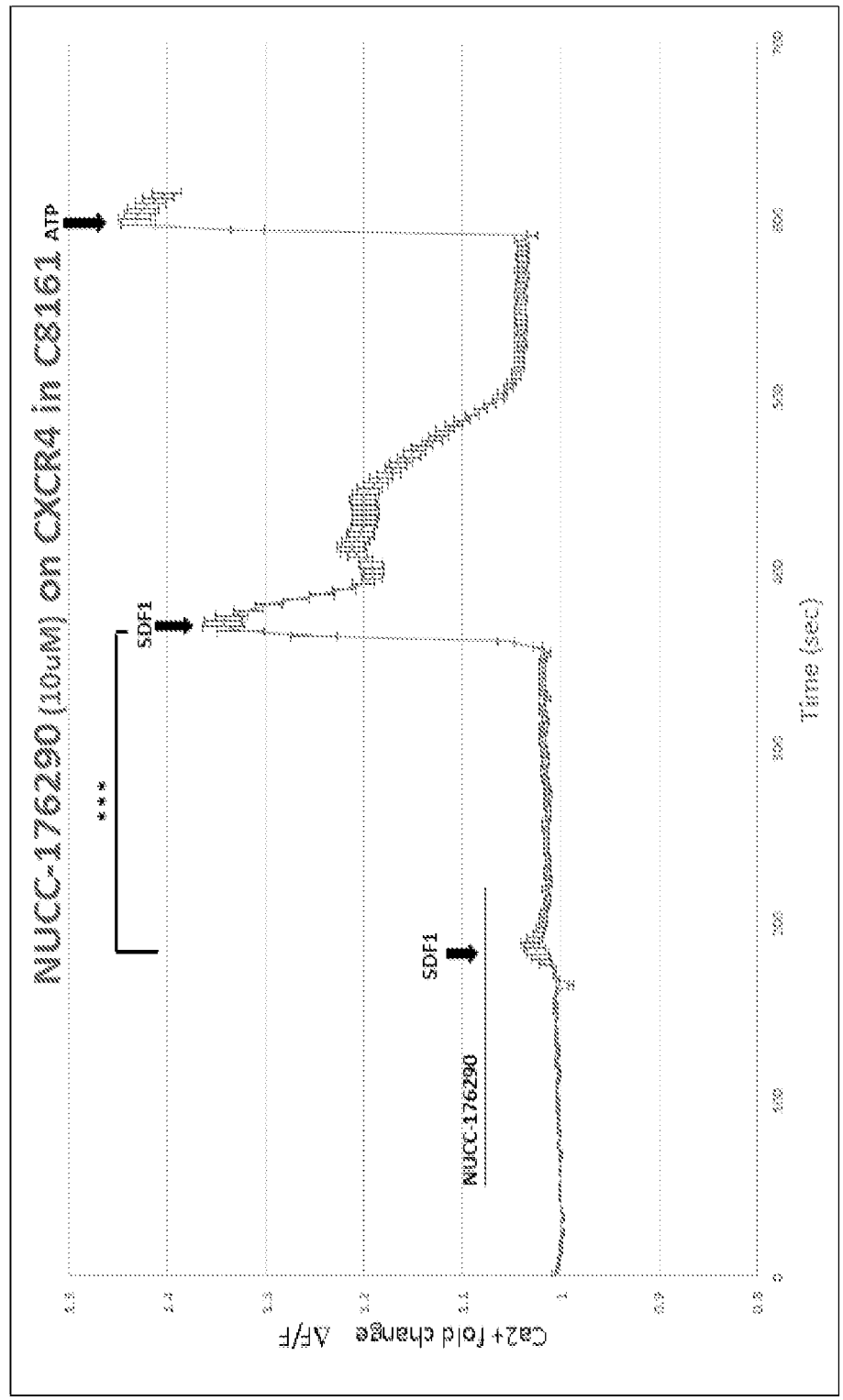
FIG. 8. (Ca)i mobilization assay using CXCR4 expressing C8161 melanoma cells. NUCC-176290 (10 μM) was added for the indicated time and blocks the effect of SDF-1. After removal of NUCC-176290, SDF-1 produces the expected calcium flux. Addition of ATP (10 μM) near the end to activate purinergic receptors was performed as a positive control for cell viability.
Figure 9:
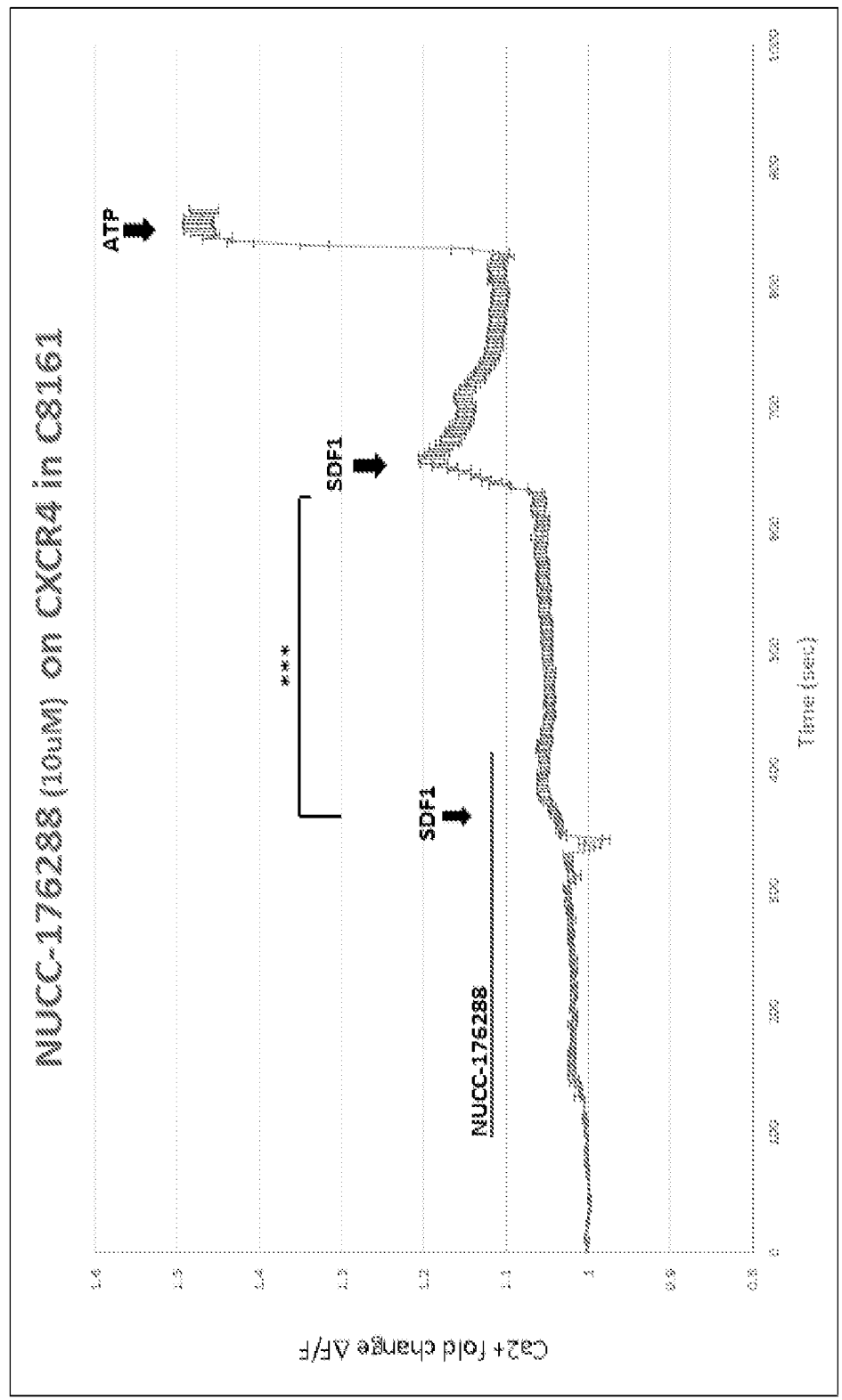
FIG. 9. (Ca)i mobilization assay using CXCR4 expressing C8161 melanoma cells. Antagonist NUCC-176288 (10 μM) was added for the indicated time and blocks the effect of SDF-1. After removal of NUCC-176288, SDF-1 produces the expected calcium flux. Addition of ATP (10 μM) near the end to activate purinergic receptors was performed as a positive control for cell viability.
Figure 10:
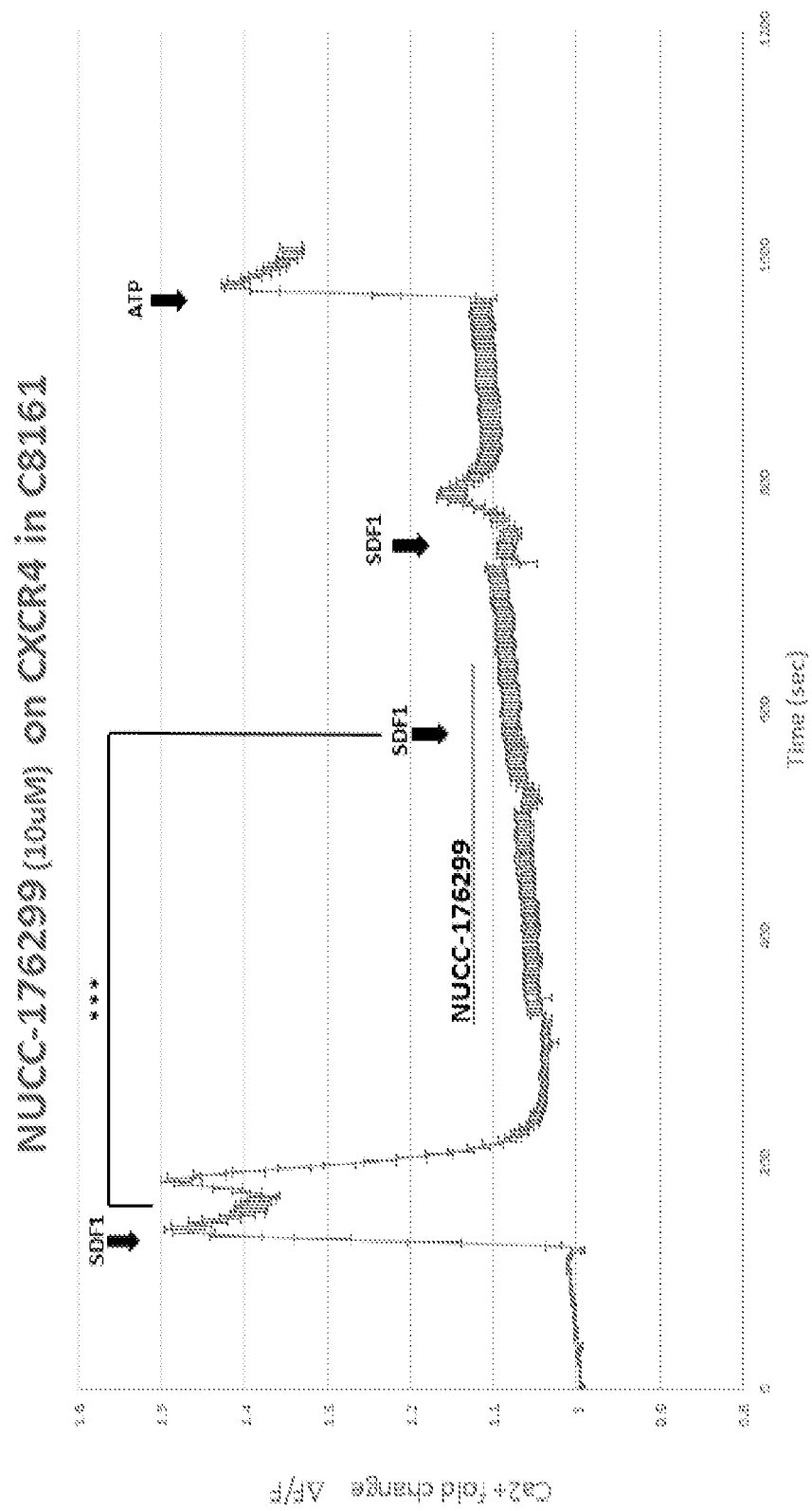
FIG. 10. (Ca)i mobilization assay using CXCR4 expressing C8161 melanoma cells. Addition of SDF-1 produces the expected calcium flux. Exposure of the cells to antagonist NUCC-176299 (10 μM) for the indicated time and blocks the effect of SDF-1. Addition of ATP (10 μM) near the end to activate purinergic receptors was performed as a positive control for cell viability.
Figure 11:
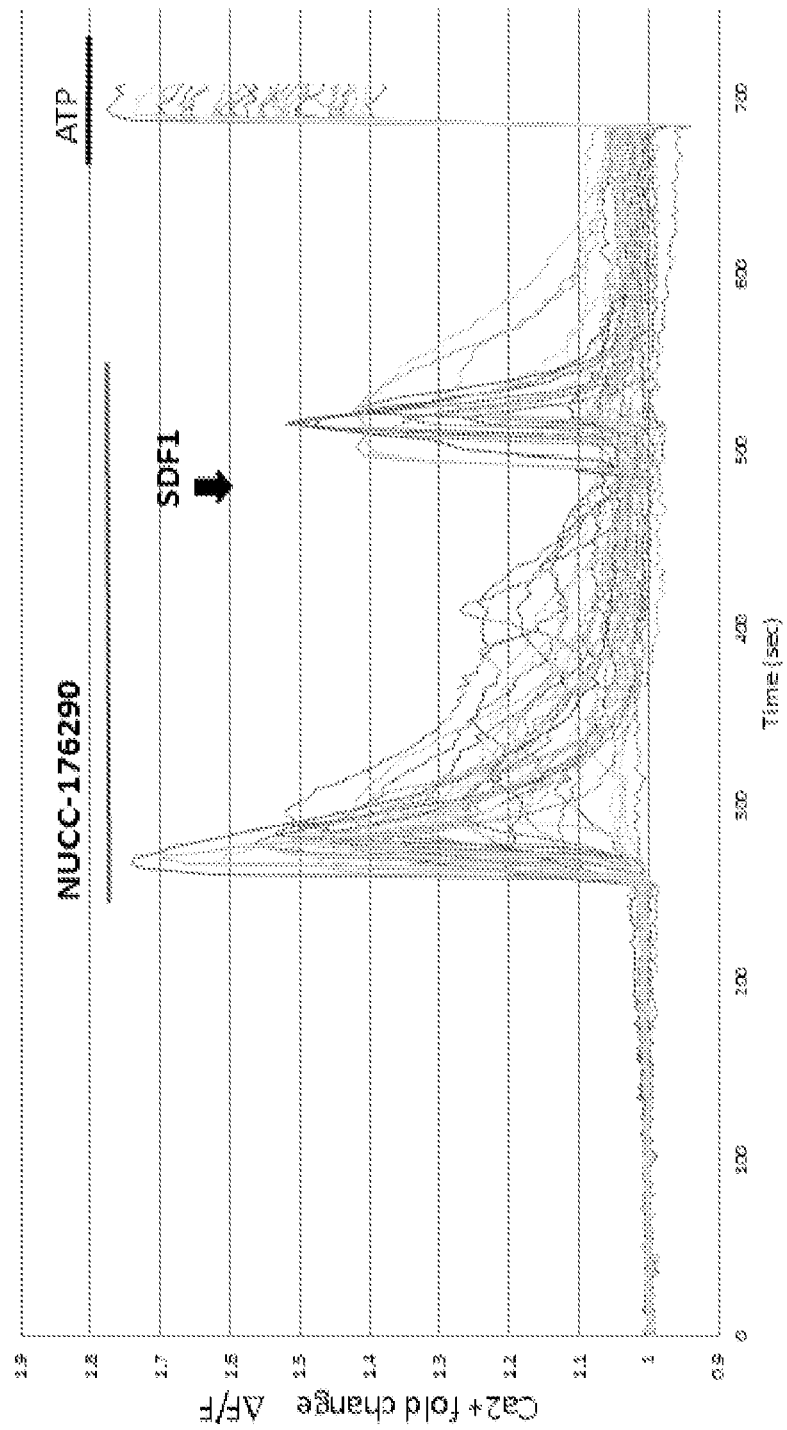
FIG. 11. (Ca)i mobilization assay using CXCR4 expressing C8161 melanoma cells. Each colored line represents the response of a different single cell. Addition of NUCC-176290 produces a robust calcium response. Subsequent additions of SDF-1 and ATP also produced strong calcium signals.
Figure 12:
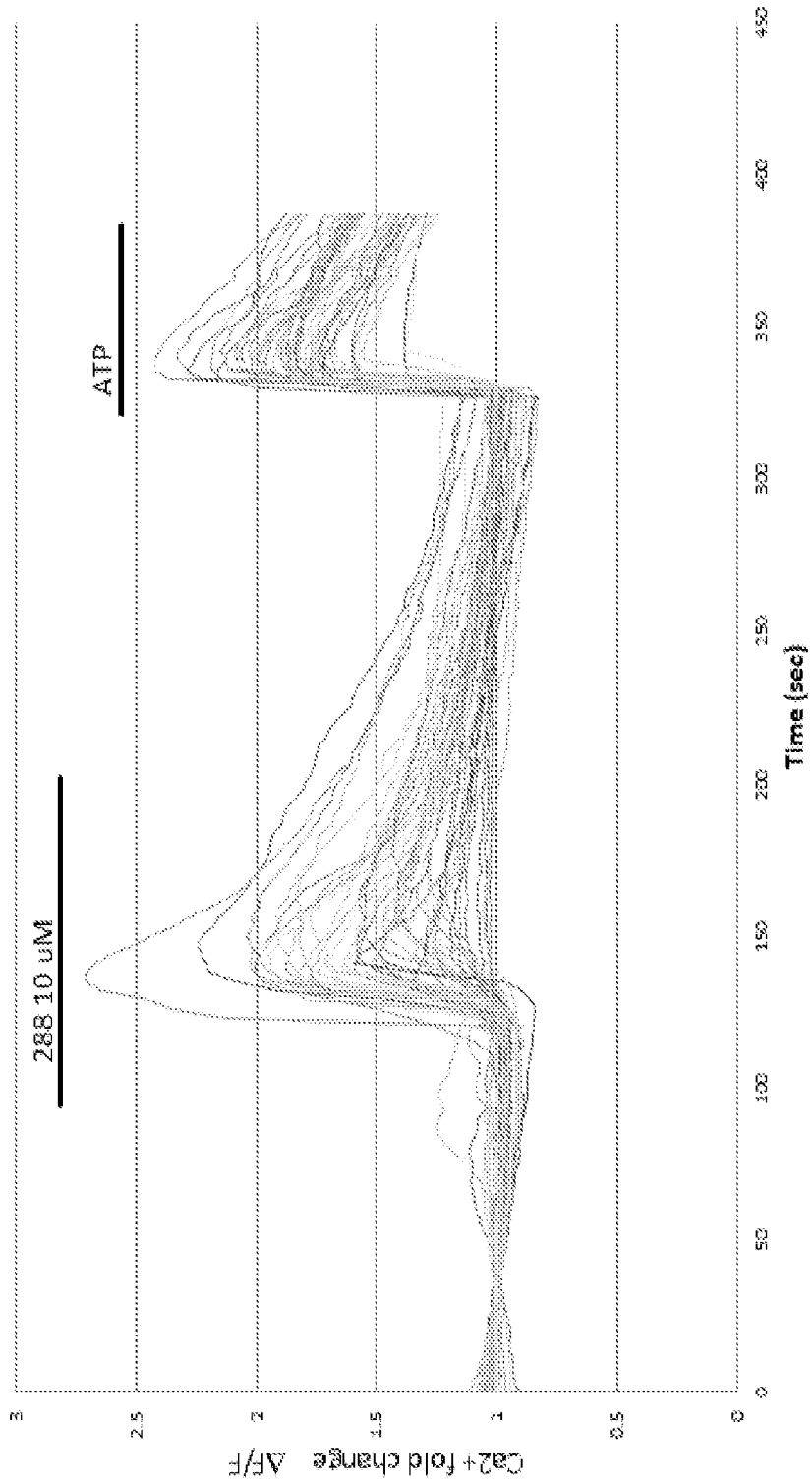
FIG. 12. (Ca)i mobilization assay using CXCR4 expressing U87 cells. Each colored line represents the response of a different single cell. Addition of NUCC-176288 (10 uM) produces a robust calcium response. Subsequent addition of ATP also produced strong calcium signals.
Figure 13:
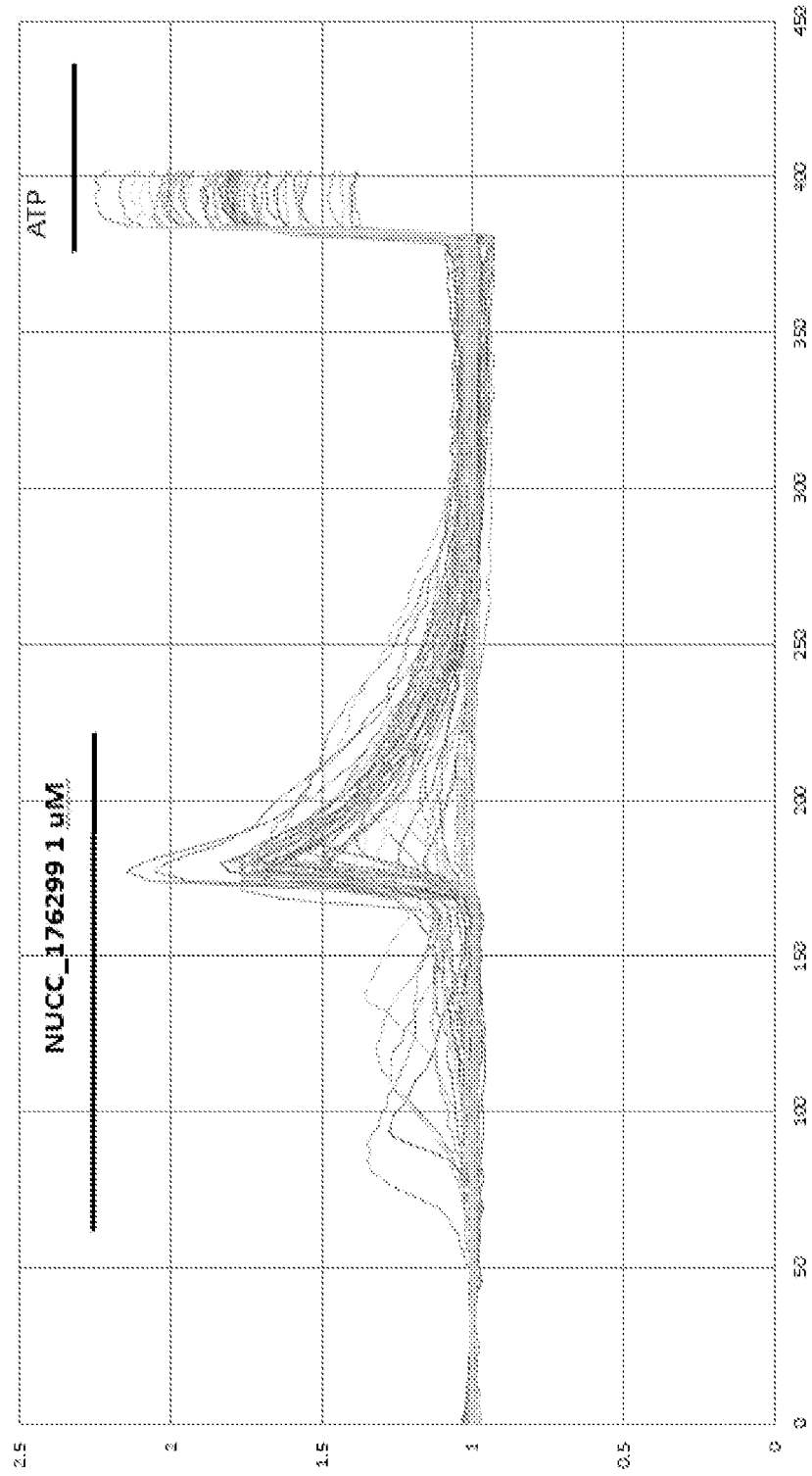
FIG. 13. (Ca)i mobilization assay using CXCR4 expressing U87 cells. Each colored line represents the response of a different single cell. Addition of NUCC-176299 produces a robust calcium response. Subsequent additions of ATP also produced strong calcium signals.
Figure 14:
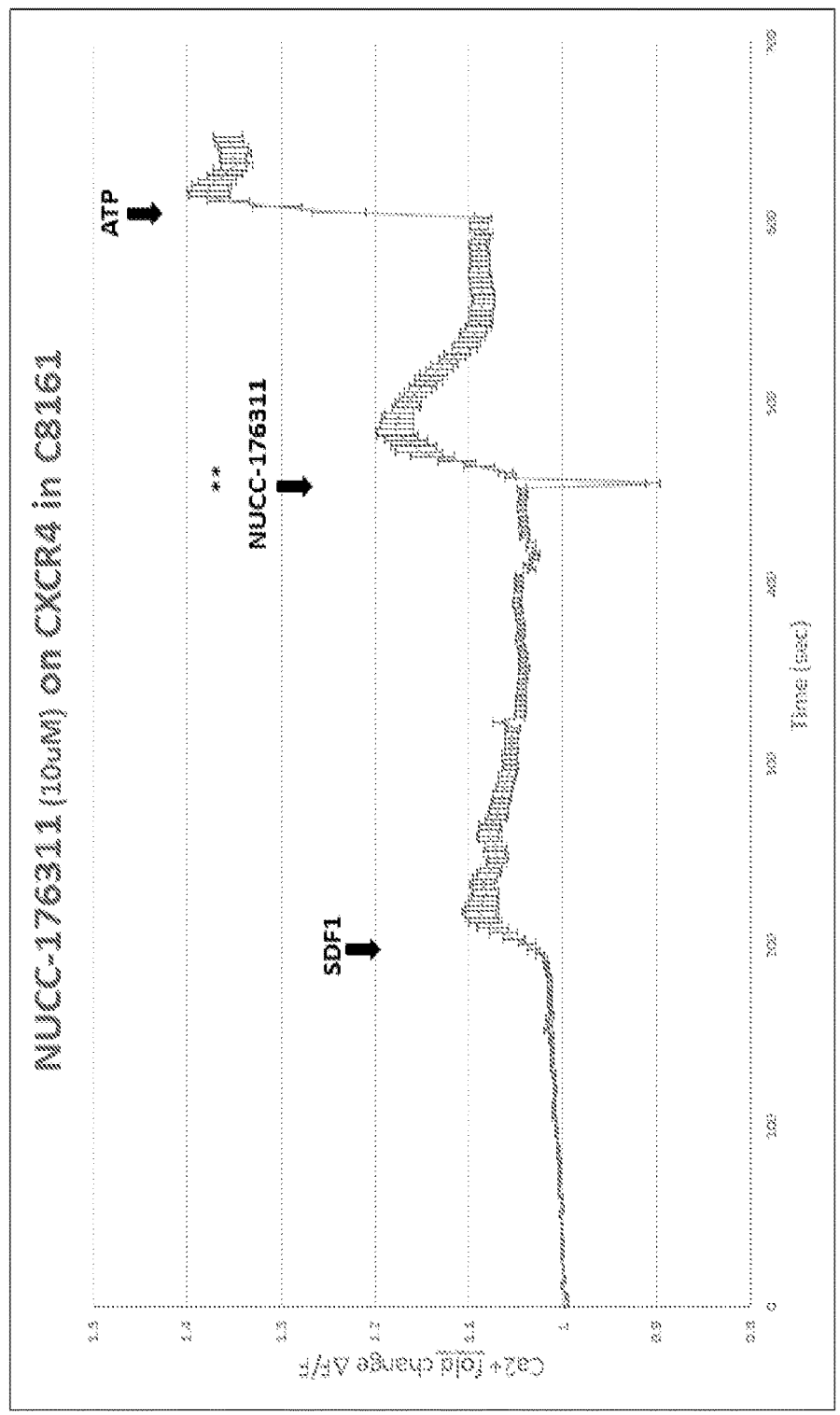
FIG. 14. (Ca)i mobilization assay using CXCR4 expressing C8161 melanoma cells. Addition of SDF-1 produces the expected calcium response. Subsequent addition of NUCC-176311 (10 μM) also produced a robust calcium response. Addition of ATP near the end to activate purinergic receptors was performed as a positive control for cell viability.
Figure 15:
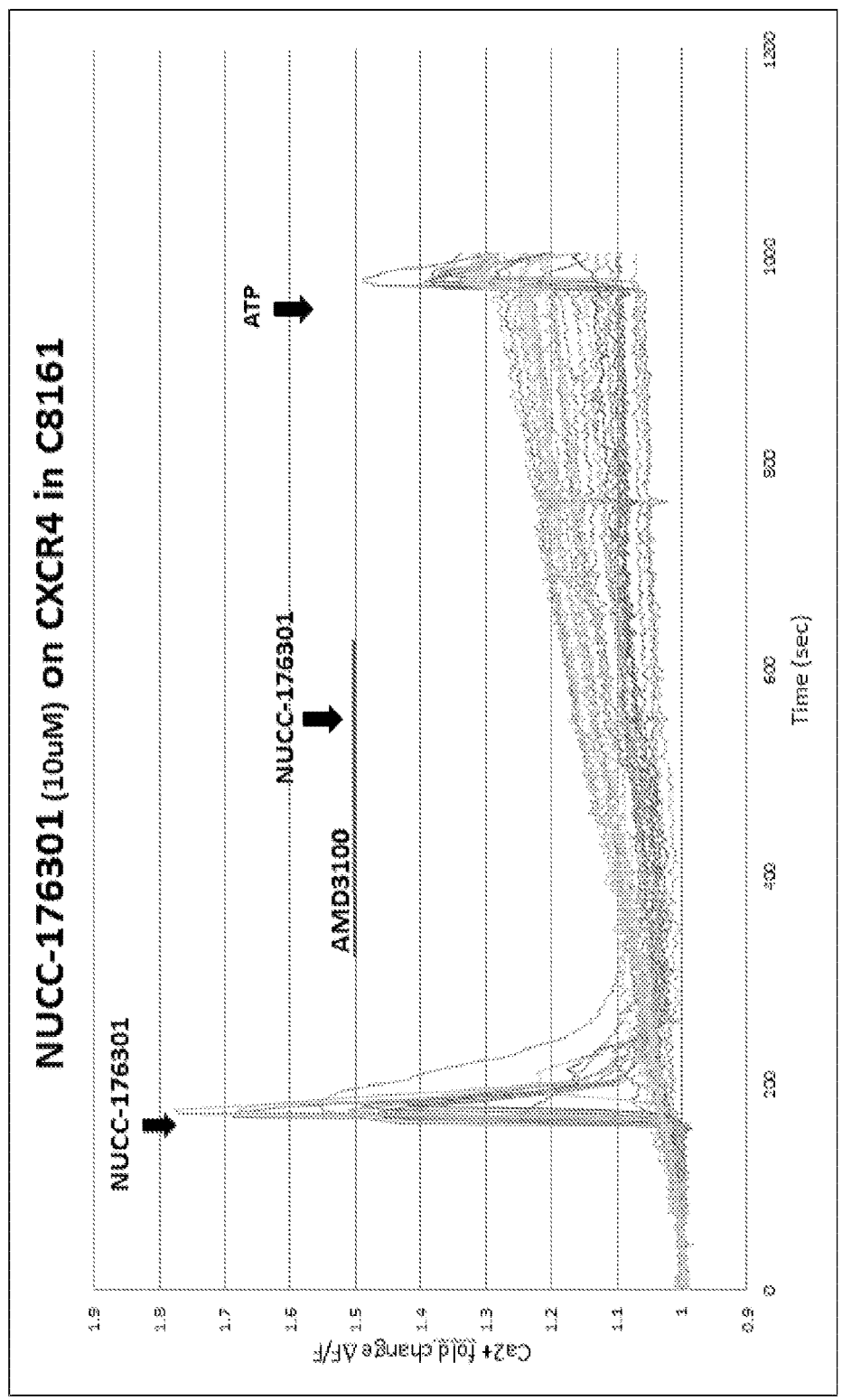
FIG. 15. (Ca)i mobilization assay using CXCR4 expressing C8161 melanoma cells. Each colored line represents the response of a different single cell. Addition of NUCC-176301 produces a robust calcium response. Treatment with selective CXCR4 antagonist AMD3100 for the indicated time prevented calcium signaling by NUCC-176301, suggesting the calcium response by NUCC-176301 is produced primarily through CXCR4 activation.
Figure 16:
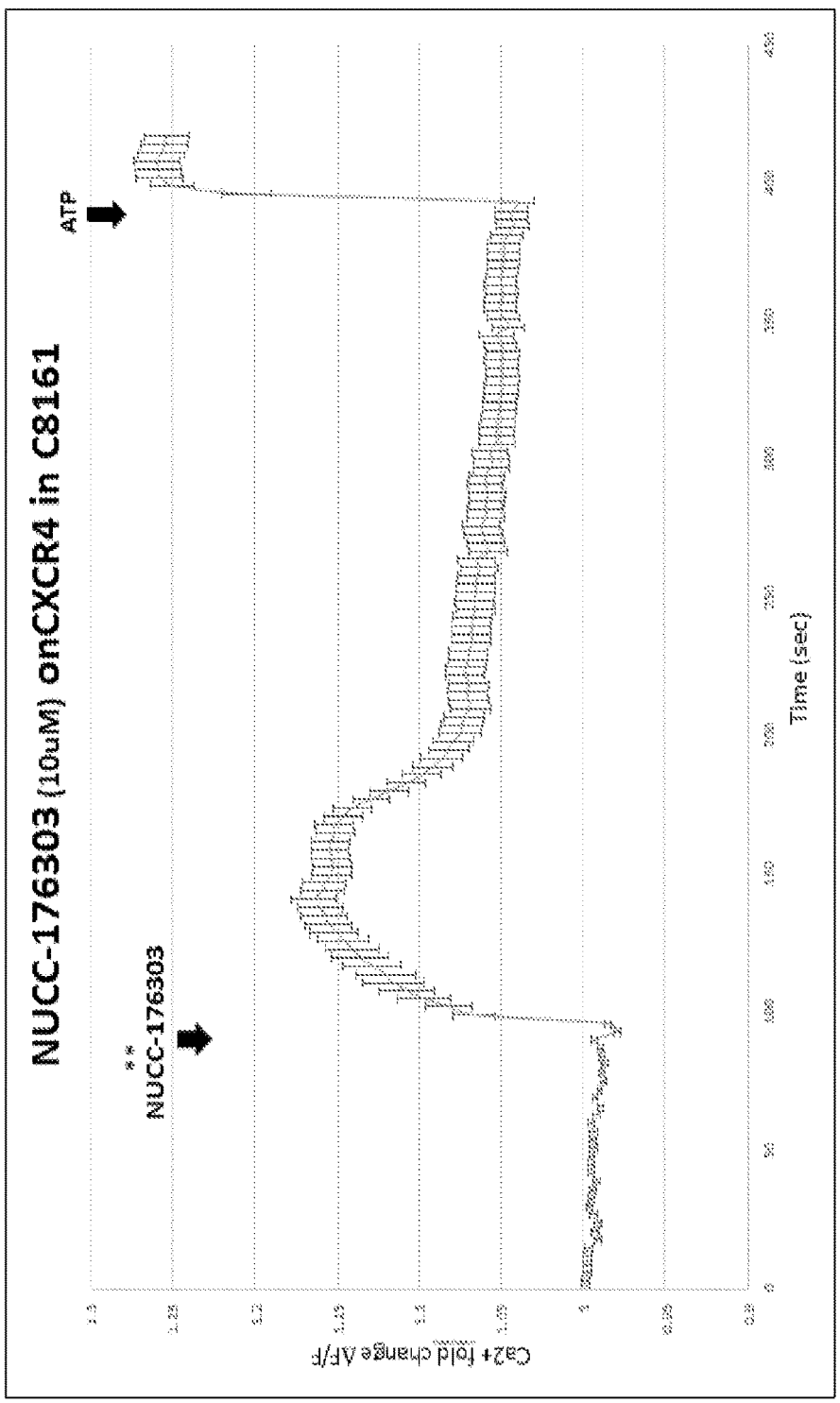
FIG. 16. (Ca)i mobilization assay using CXCR4 expressing C8161 melanoma cells. Addition of NUCC-176303 (10 μM) produced a robust calcium response. Addition of ATP near the end to activate purinergic receptors was performed as a positive control for cell viability.
Figure 17:
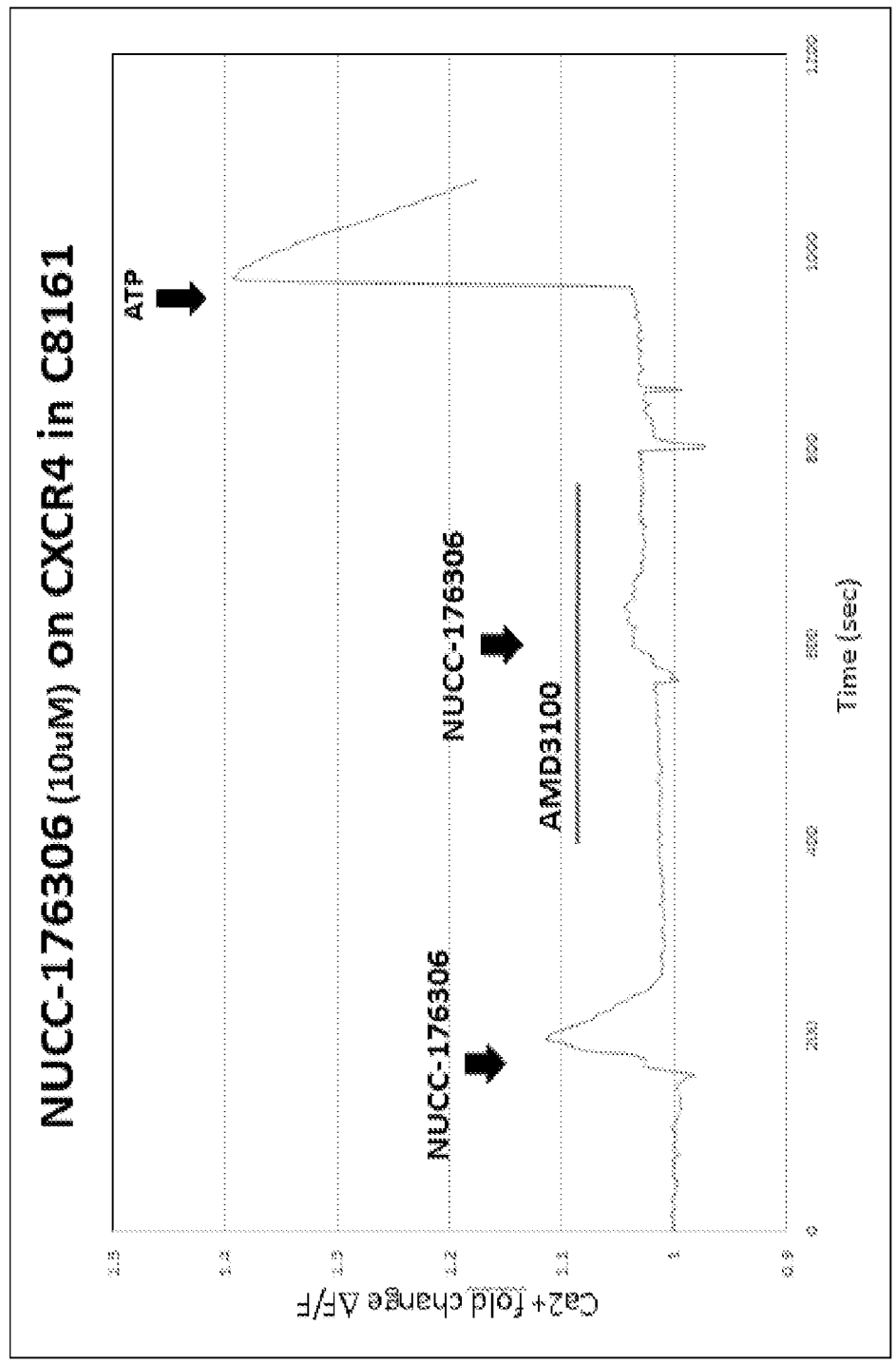
FIG. 17. (Ca)i mobilization assay using CXCR4 expressing C8161 melanoma cells. Addition of NUCC-176306 produces a robust calcium response. Treatment with selective CXCR4 antagonist AMD3100 for the indicated time prevented calcium signaling by NUCC-176306, suggesting the calcium response by NUCC-176306 is produced primarily through CXCR4 activation.
Figure 18:
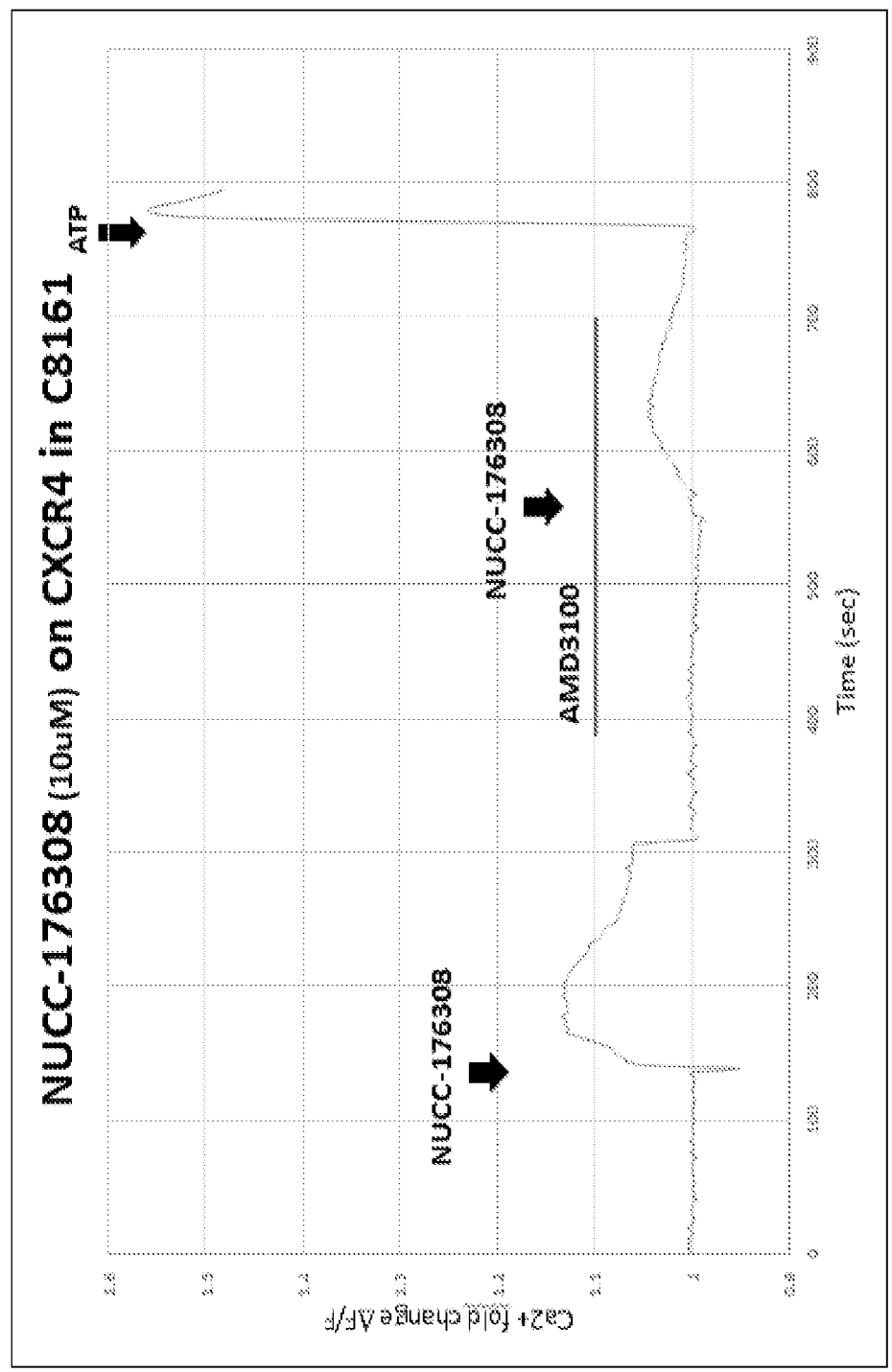
FIG. 18. (Ca)i mobilization assay using CXCR4 expressing C8161 melanoma cells. Addition of NUCC-176308 produces a robust calcium response. Treatment with selective CXCR4 antagonist AMD3100 for the indicated time prevented calcium signaling by NUCC-176308, suggesting the calcium response by NUCC-176308 is produced primarily through CXCR4 activation.
Figure 19:
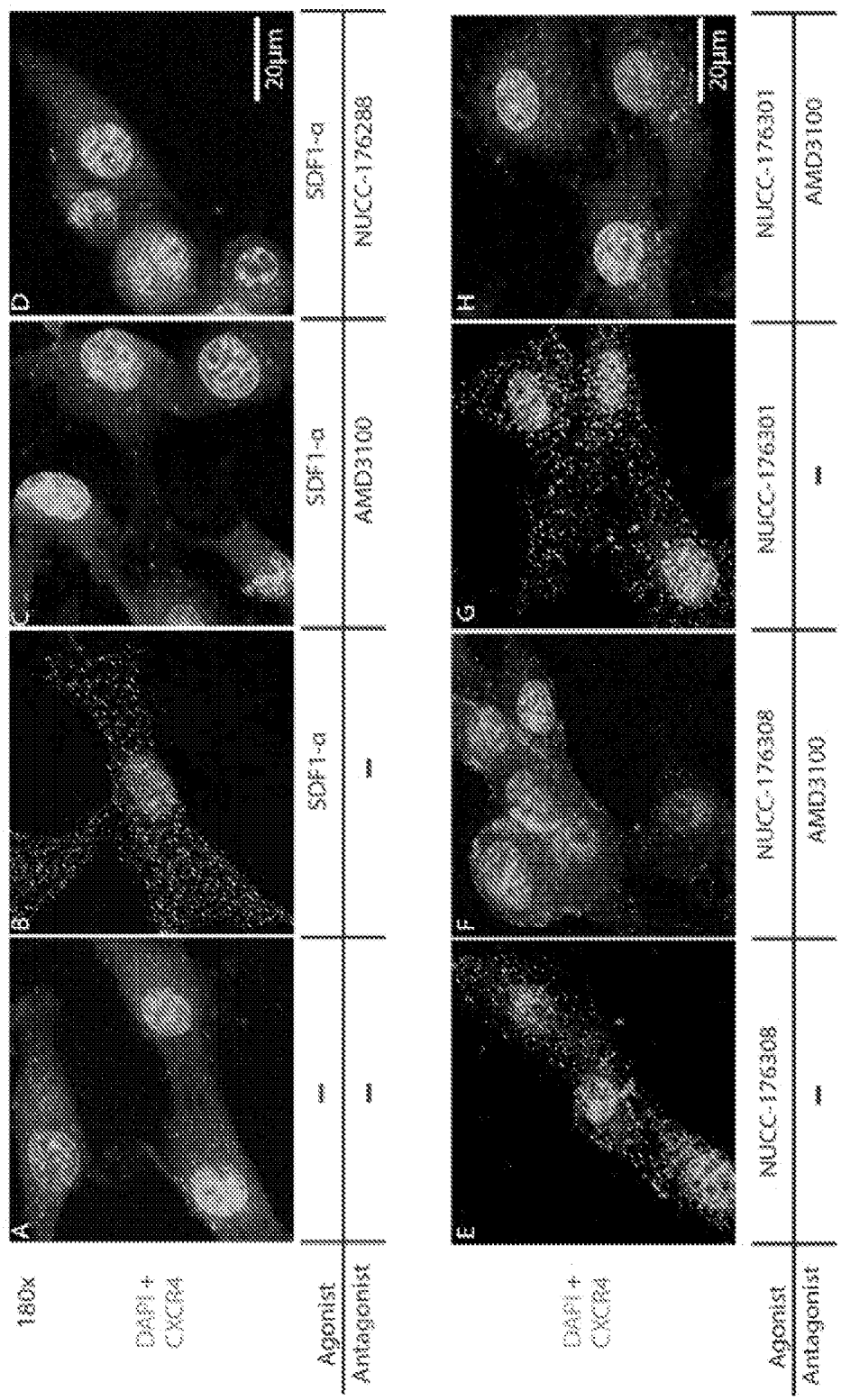
FIG. 19. CXCR4 internalization assay: U87 glioblastoma cells expressing the CXCR4 receptor are treated with experimental agonists and antagonists. As a verification to positive hits found in the $Ca^{2+}$ imaging screen, direct stimulation of the CXCR4 causes (β-arrestin mediated internalization of the receptor that is comparable to that caused by SDF-1, its natural ligand. Pharmacological blockade of CXCR4 with AMD3100, an established antagonist, prevents this internalization phenotype, thus further demonstrating the specificity of the agonists. Conversely, antagonists were evaluated in their ability to prevent SDF-1 mediated internalization. Immunofluorescence of the CXCR4 and confocal microscopy were used to visualize the localization of the CXCR4 receptor (membrane vs. internalized). All images were processed blinded to treatment conditions.
Figure 20:
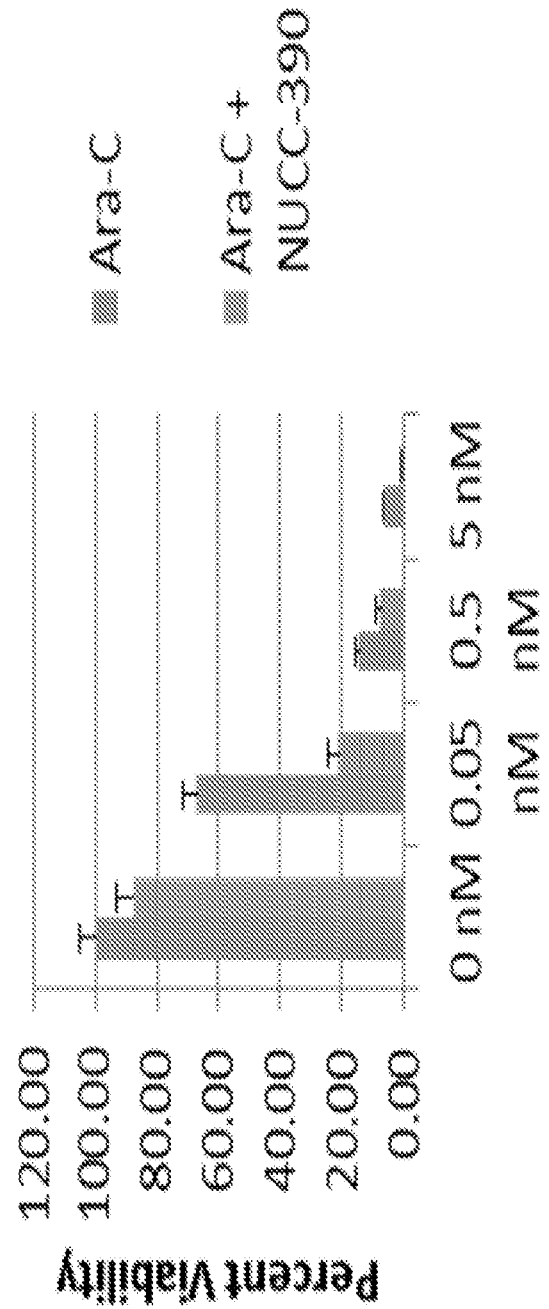
FIG. 20. Cell viability assay with agonist NUCC-390 and known chemotherapeutics. The first bar is viability no NUCC-390 or Ara-C. Otherwise, the concentration of NUCC-390 was maintained at 50 μM in all experiments. U937 cells were treated with NUCC-390 and the indicated concentration of Ara-C. NUCC-390 had only a modest effect by itself, but significantly increased the cytotoxicity of Ara-C when used in combination.
Figure 21:
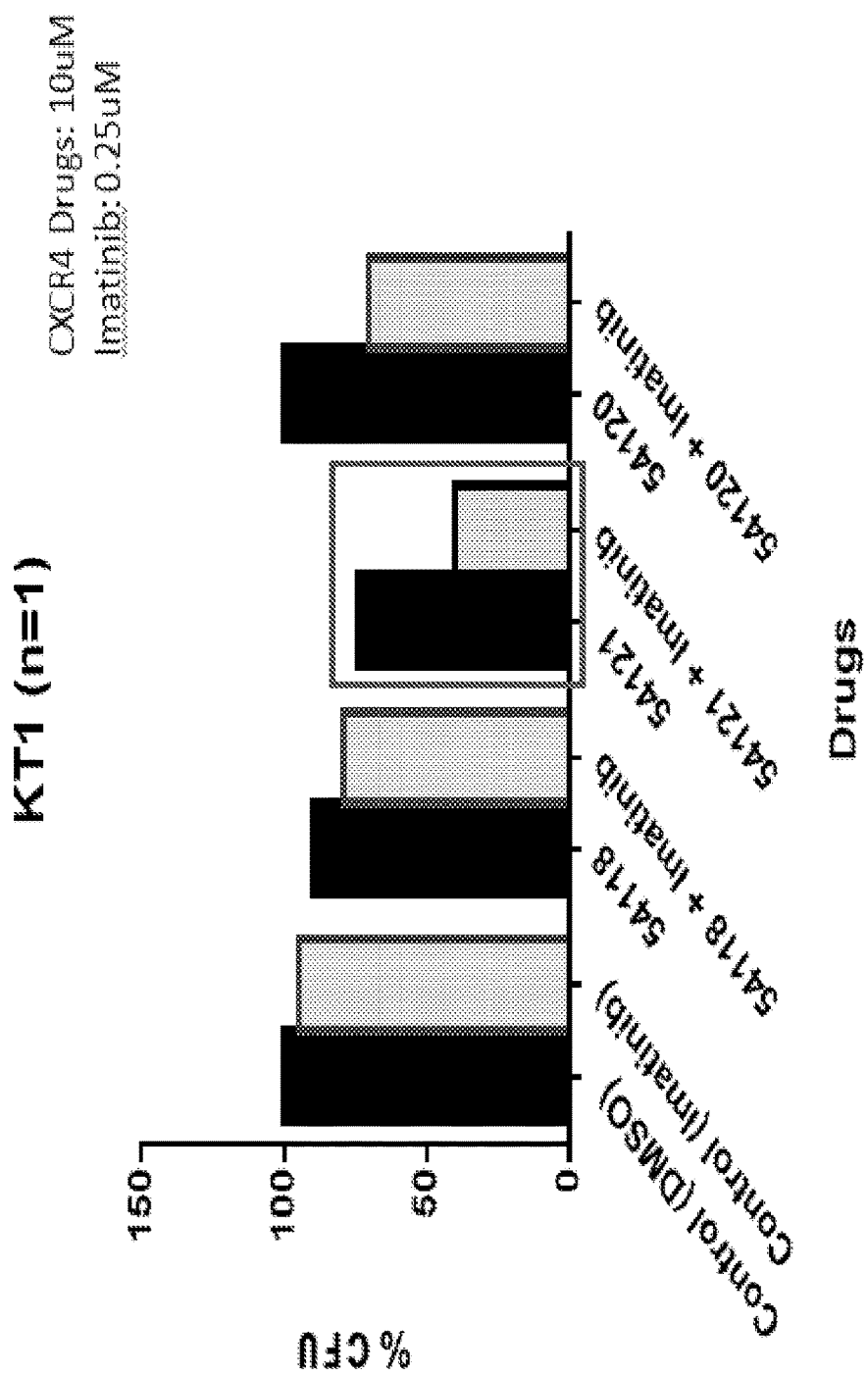
FIG. 21. Cell viability assay measuring colony forming units of KT1 cells. Cells were treated with kinase inhibitor imatinib, the indicated CXCR4 agent, or a combination, at the indicated concentrations. Compound NUCC-54121 enhanced the cell killing ability of imatinib.
Figure 22:
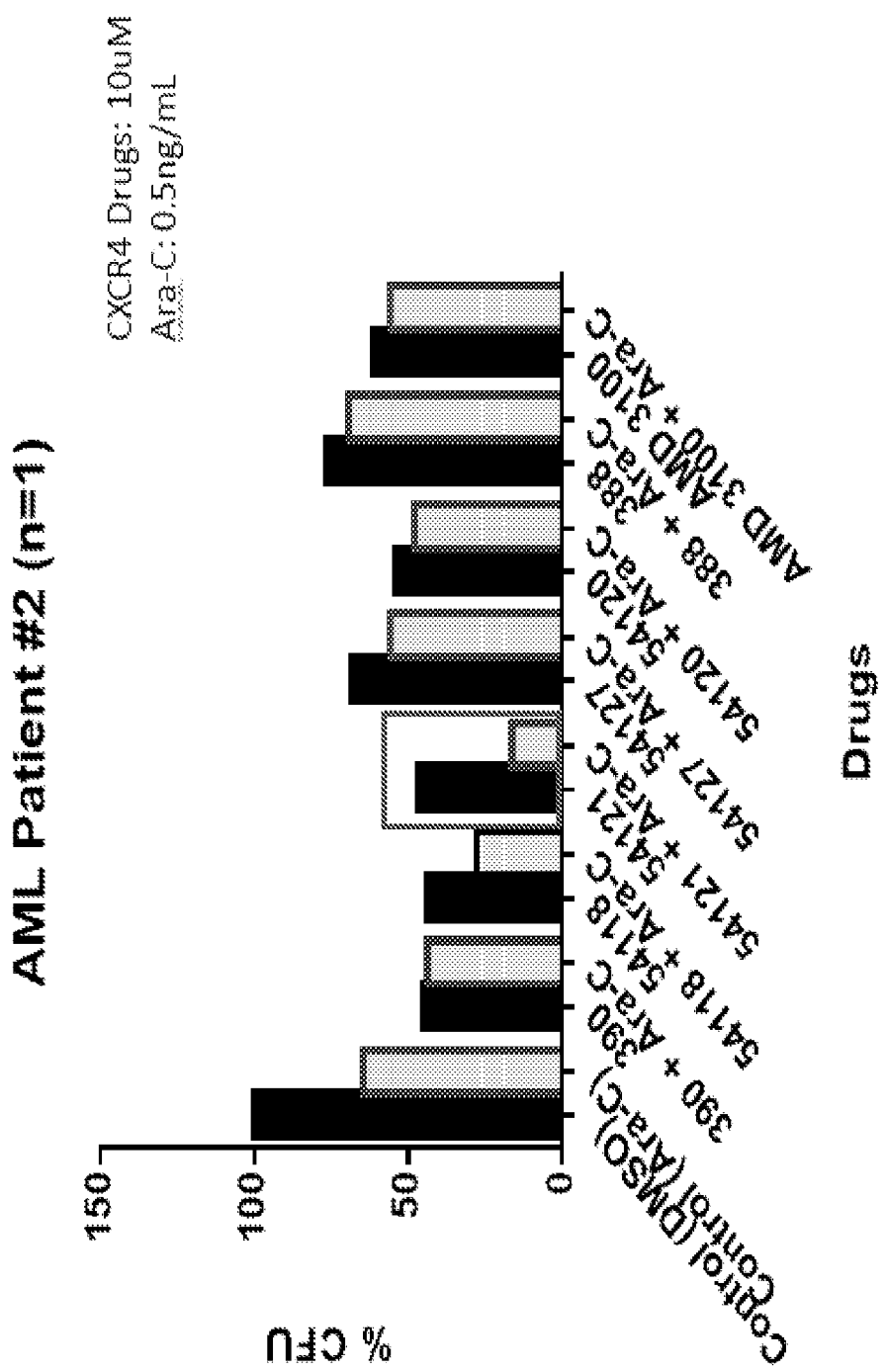
FIG. 22. Cell viability assay measuring colony forming units of from AML patient #2. Cells were treated with cytotoxic agent Ara-C, the indicated CXCR4 agent, or a combination. Compound NUCC-54121 enhanced the cell killing ability of Ara-C.

Chemokines are well known for their ability to stimulate chemotaxis of leukocytes and stem cells. In order to further establish the biological activity of the CXCR4 agonists, the ability of SDF-1 and NUCC-390 to produce chemotaxis of C8161 cells was compared using a Boyden chamber assay. SDF-1 produced robust chemotactic activity which was matched by the effects of NUCC-390 demonstrating that this novel agonist can produce one of the major biological effects of chemokines (FIG. 6).

Example 9

Compound Synthesis

The following exemplary compounds have been obtained, screened, designed, synthesized, and/or tested for biological activity (effect on calcium response and pharmacologic effect).

TABLE 2

| Exemplary compounds | | | | |
|---|---|---|---|---|
| Structure | Molecule Name | Synthetic Route | Effect on Calcium Response | Pharmacology |
| 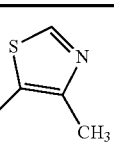 | NUCC-0000387 | | + | Agonist |
| 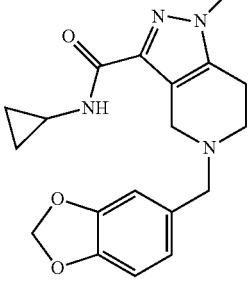 | NUCC-0000388 | A | | Antagonist |
| 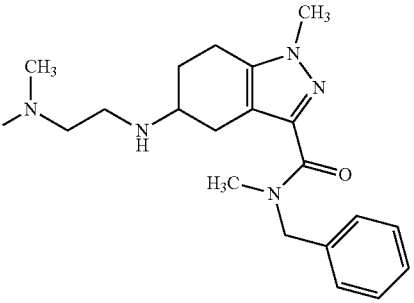 | NUCC-0000390 | A | +++ | Agonist |

TABLE 2-continued
Exemplary compounds
| Structure | Molecule Name | Synthetic Route | Effect on Calcium Response | Pharmacology |
|---|---|---|---|---|
| 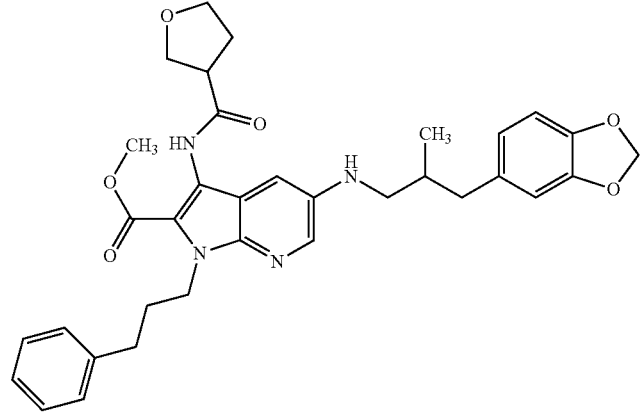 [SMILES: COC(=O)c1c(NC(=O)C2CCOC2)c2cc(NCC(C)Cc3ccc4c(c3)OCO4)cnc2n1CCCc1ccccc1] | NUCC-0000392 | | | Antagonist |
| 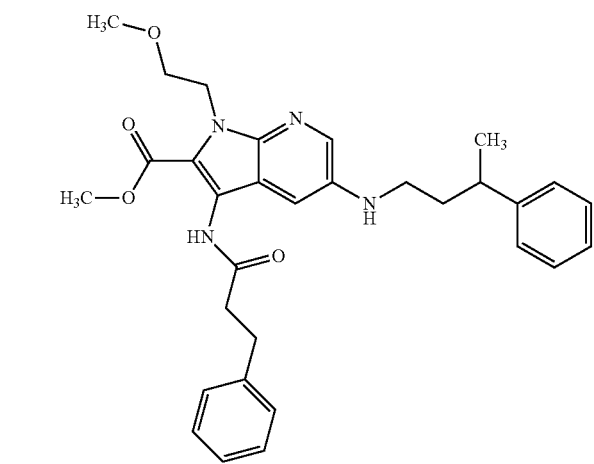 [SMILES: COCCn1c(C(=O)OC)c(NC(=O)CCc2ccccc2)c2cc(NCCC(C)c3ccccc3)cnc21] | NUCC-0000393 | | + | Agonist |
| 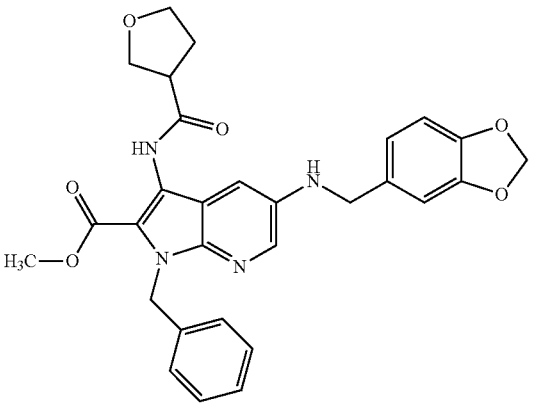 [SMILES: COC(=O)c1c(NC(=O)C2CCOC2)c2cc(NCc3ccc4c(c3)OCO4)cnc2n1Cc1ccccc1] | NUCC-0000397 | | | Antagonist |

TABLE 2-continued

Exemplary compounds

| Structure | Molecule Name | Synthetic Route | Effect on Calcium Response | Pharmacology |
|---|---|---|---|---|
| 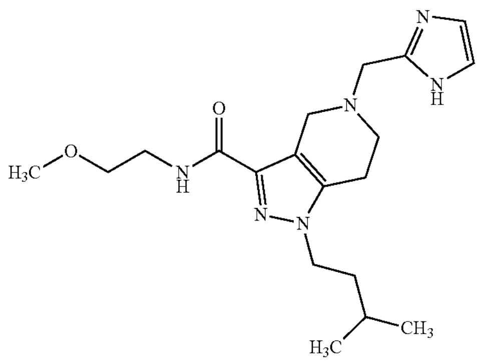 [SMILES: COCCNC(=O)c1nn(CCC(C)C)c2c1CN(Cc1ncc[nH]1)CC2] | NUCC-0000398 | B | +++ | Agonist |
| 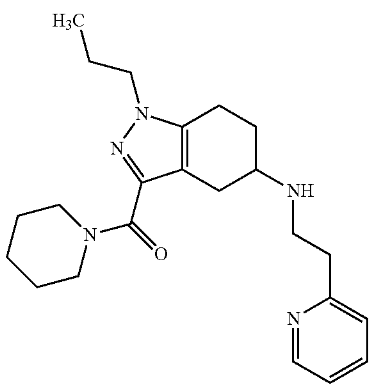 [SMILES: CCCn1nc(C(=O)N2CCCCC2)c2c1CCC(NCCc1ccccn1)C2] | NUCC-0000400 | | − | |
| 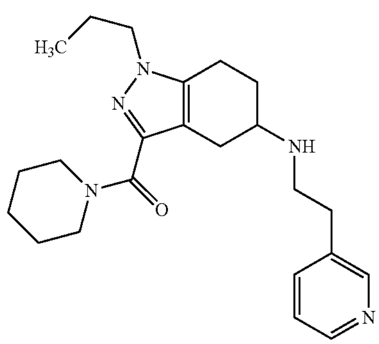 [SMILES: CCCn1nc(C(=O)N2CCCCC2)c2c1CCC(NCCc1cccnc1)C2] | NUCC-0054118 | A | +++ | Agonist |
| 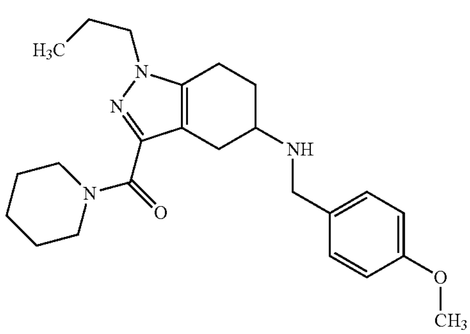 [SMILES: CCCn1nc(C(=O)N2CCCCC2)c2c1CCC(NCc1ccc(OC)cc1)C2] | NUCC-0054119 | | − | |

TABLE 2-continued
Exemplary compounds
| Structure | Molecule Name | Synthetic Route | Effect on Calcium Response | Pharmacology |
|---|---|---|---|---|
| 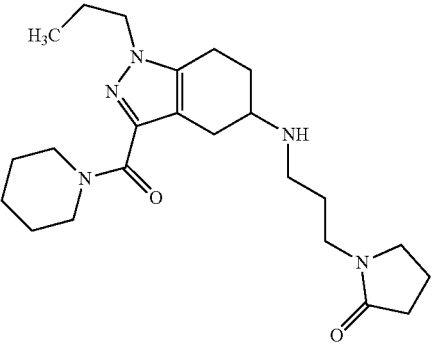 [SMILES: CCCn1nc(C(=O)N2CCCCC2)c2c1CCC(NCCCN1CCCC1=O)C2] | NUCC-0054120 | A | | Antagonist |
| 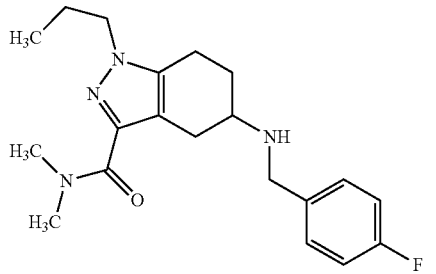 [SMILES: CCCn1nc(C(=O)N(C)C)c2c1CCC(NCc1ccc(F)cc1)C2] | NUCC-0054121 | A | +++ | Agonist |
| 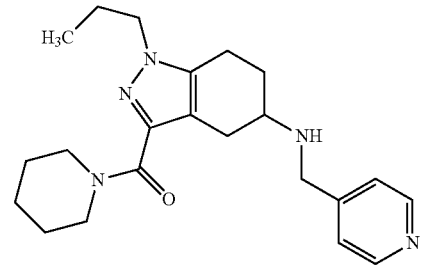 [SMILES: CCCn1nc(C(=O)N2CCCCC2)c2c1CCC(NCc1ccncc1)C2] | NUCC-0054122 | | − | |
| 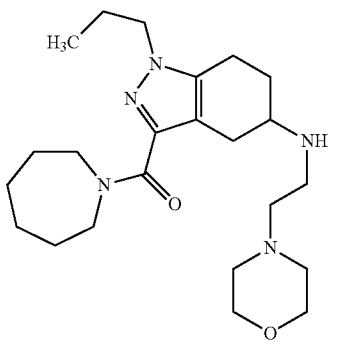 [SMILES: CCCn1nc(C(=O)N2CCCCCC2)c2c1CCC(NCCN1CCOCC1)C2] | NUCC-0054123 | | − | |
| 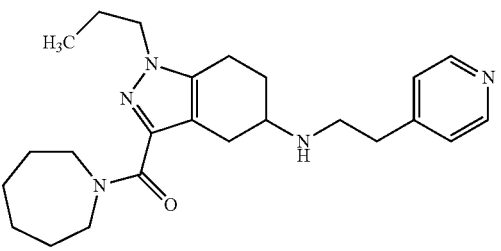 [SMILES: CCCn1nc(C(=O)N2CCCCCC2)c2c1CCC(NCCc1ccncc1)C2] | NUCC-0054124 | | − | |

TABLE 2-continued

Exemplary compounds

| Structure | Molecule Name | Synthetic Route | Effect on Calcium Response | Pharmacology |
|---|---|---|---|---|
| *(structure)* | NUCC-0054125 | | − | |
| *(structure)* | NUCC-0054126 | | − | |
| *(structure)* | NUCC-0054127 | A | ++ | Agonist |
| *(structure)* | NUCC-0054128 | | − | |

TABLE 2-continued

Exemplary compounds

| Structure | Molecule Name | Synthetic Route | Effect on Calcium Response | Pharmacology |
|---|---|---|---|---|
| 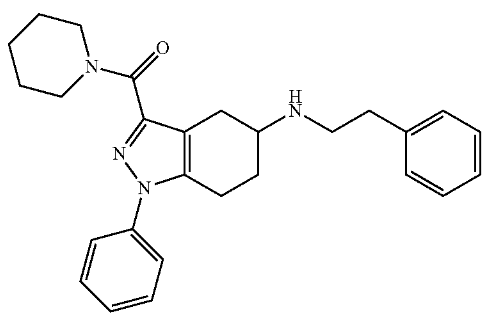 [SMILES: O=C(c1nn(-c2ccccc2)c2c1CC(NCCc1ccccc1)CC2)N1CCCCC1] | NUCC-0054129 | | − | |
| 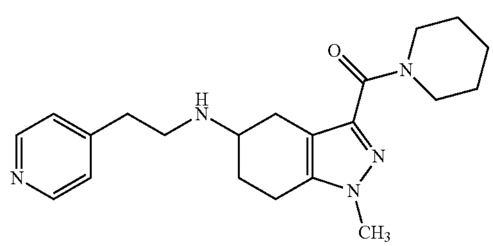 [SMILES: Cn1nc(C(=O)N2CCCCC2)c2c1CCC(NCCc1ccncc1)C2] | NUCC-0176286 | A | + | |
| 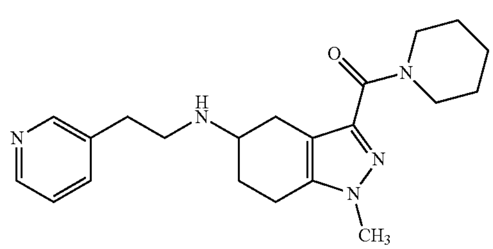 [SMILES: Cn1nc(C(=O)N2CCCCC2)c2c1CCC(NCCc1cccnc1)C2] | NUCC-0176287 | A | ++ | |
| 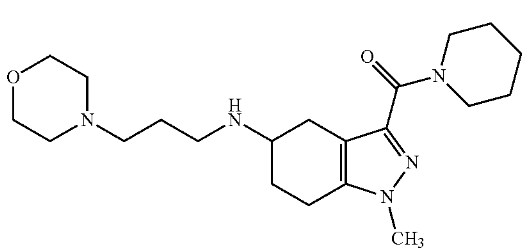 [SMILES: Cn1nc(C(=O)N2CCCCC2)c2c1CCC(NCCCN1CCOCC1)C2] | NUCC-0176288 | A | + | Antagonist |
| 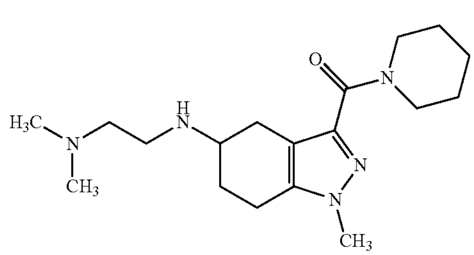 [SMILES: CN(C)CCNC1CCc2c(c(C(=O)N3CCCCC3)nn2C)C1] | NUCC-0176289 | A | ++ | |

TABLE 2-continued
Exemplary compounds
| Structure | Molecule Name | Synthetic Route | Effect on Calcium Response | Pharmacology |
|---|---|---|---|---|
| 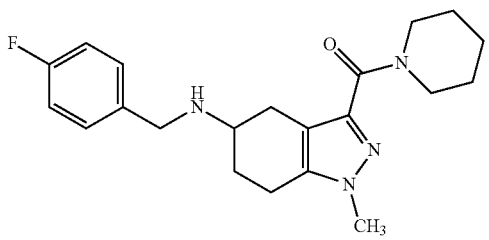 [SMILES: Cn1nc(C(=O)N2CCCCC2)c2c1CCC(NCc1ccc(F)cc1)C2] | NUCC-0176290 | A | + | Antagonist |
| 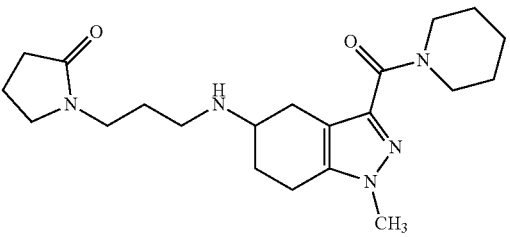 [SMILES: Cn1nc(C(=O)N2CCCCC2)c2c1CCC(NCCCN1CCCC1=O)C2] | NUCC-0176291 | A | +++ | |
| 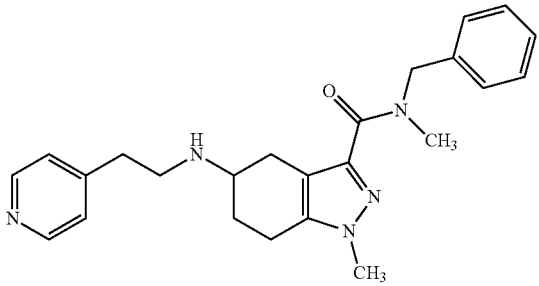 [SMILES: CN(Cc1ccccc1)C(=O)c1nn(C)c2c1CC(NCCc1ccncc1)CC2] | NUCC-0176292 | A | +++ | |
| 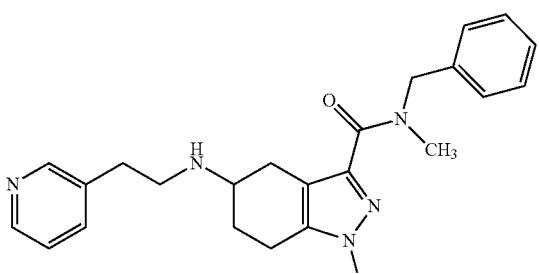 | NUCC-0176293 | A | + | |
| 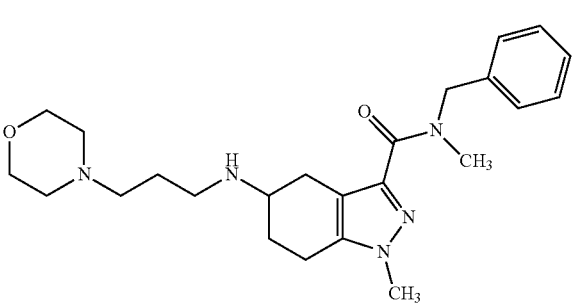 [SMILES: CN(Cc1ccccc1)C(=O)c1nn(C)c2c1CC(NCCCN1CCOCC1)CC2] | NUCC-0176294 | A | ++ | |

TABLE 2-continued

Exemplary compounds

| Structure | Molecule Name | Synthetic Route | Effect on Calcium Response | Pharmacology |
|---|---|---|---|---|
| 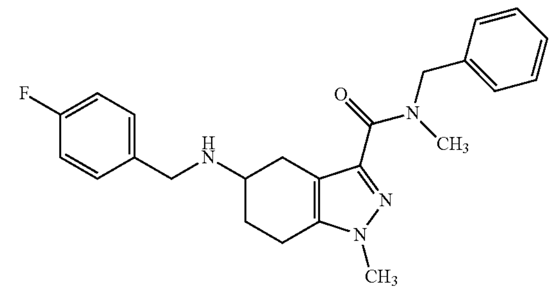 [SMILES: CN(Cc1ccccc1)C(=O)c1nn(C)c2c1CC(NCc1ccc(F)cc1)CC2] | NUCC-0176295 | A | ++ | |
| 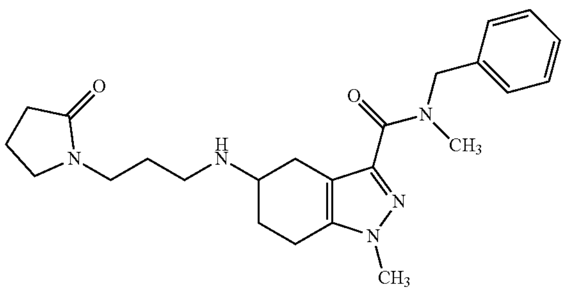 [SMILES: CN(Cc1ccccc1)C(=O)c1nn(C)c2c1CC(NCCCN1CCCC1=O)CC2] | NUCC-0176296 | A | ++ | |
| 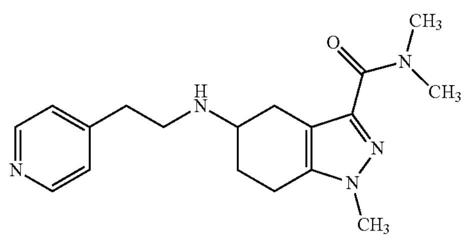 [SMILES: CN(C)C(=O)c1nn(C)c2c1CC(NCCc1ccncc1)CC2] | NUCC-0176297 | A | ++ | |
| 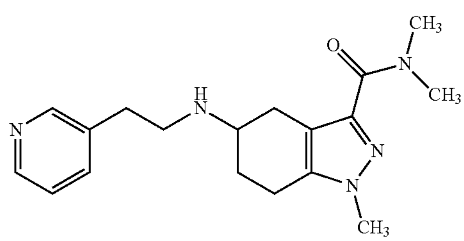 [SMILES: CN(C)C(=O)c1nn(C)c2c1CC(NCCc1cccnc1)CC2] | NUCC-0176298 | A | ++ | |
| 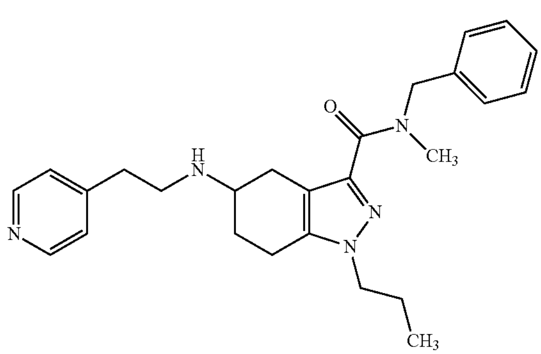 [SMILES: CCCn1nc(C(=O)N(C)Cc2ccccc2)c2c1CCC(NCCc1ccncc1)C2] | NUCC-0176299 | A | ++ | Antagonist |

TABLE 2-continued

Exemplary compounds

| Structure | Molecule Name | Synthetic Route | Effect on Calcium Response | Pharmacology |
|---|---|---|---|---|
| 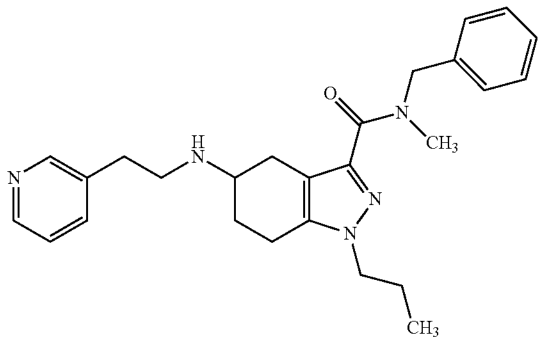 [SMILES: CCCn1nc(C(=O)N(C)Cc2ccccc2)c2c1CCC(NCCc1cccnc1)C2] | NUCC-0176300 | A | ++ | |
| 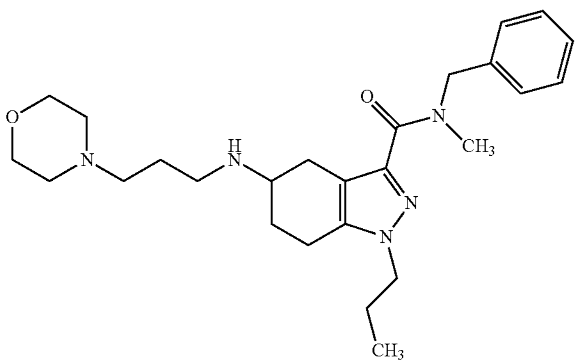 [SMILES: CCCn1nc(C(=O)N(C)Cc2ccccc2)c2c1CCC(NCCCN1CCOCC1)C2] | NUCC-0176301 | A | ++ | Agonist |
| 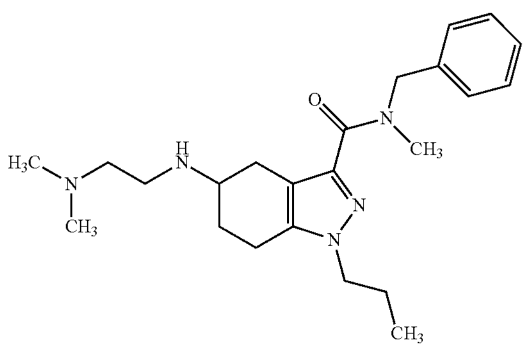 [SMILES: CCCn1nc(C(=O)N(C)Cc2ccccc2)c2c1CCC(NCCN(C)C)C2] | NUCC-0176302 | A | + | |
| 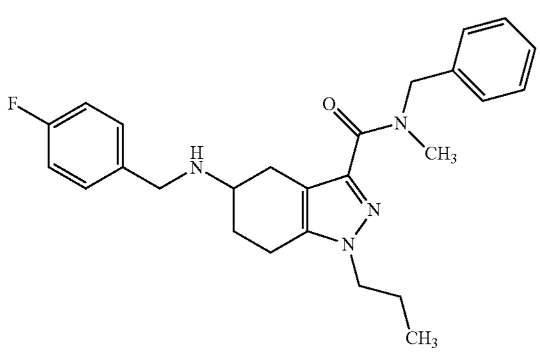 [SMILES: CCCn1nc(C(=O)N(C)Cc2ccccc2)c2c1CCC(NCc1ccc(F)cc1)C2] | NUCC-0176303 | A | +++ | Agonist |

TABLE 2-continued
Exemplary compounds
| Structure | Molecule Name | Synthetic Route | Effect on Calcium Response | Pharmacology |
|---|---|---|---|---|
| 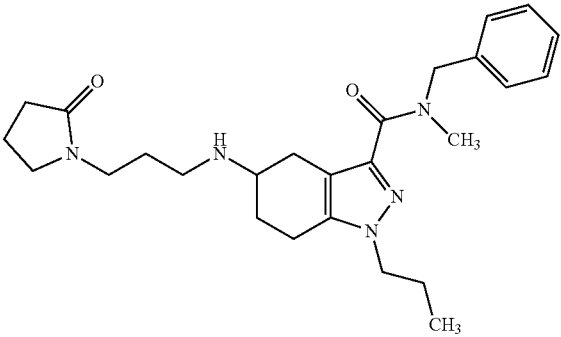 [SMILES: CCCn1nc(C(=O)N(C)Cc2ccccc2)c2c1CCC(NCCCN1CCCC1=O)C2] | NUCC-0176304 | A | +++ | |
| 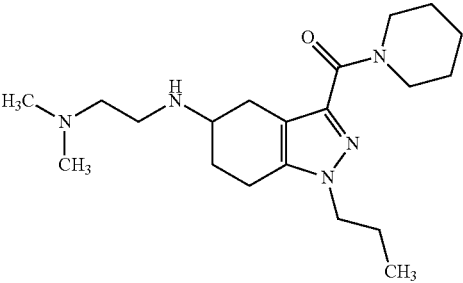 [SMILES: CCCn1nc(C(=O)N2CCCCC2)c2c1CCC(NCCN(C)C)C2] | NUCC-0176305 | A | ++ | |
| 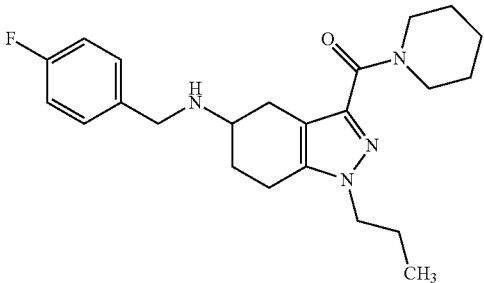 [SMILES: CCCn1nc(C(=O)N2CCCCC2)c2c1CCC(NCc1ccc(F)cc1)C2] | NUCC-0176306 | A | +++ | Agonist |
| 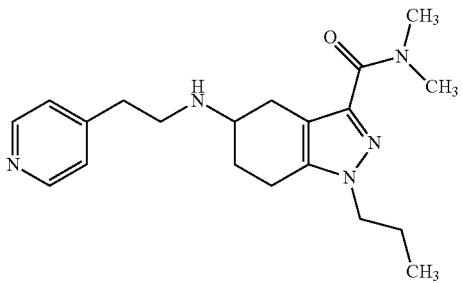 [SMILES: CCCn1nc(C(=O)N(C)C)c2c1CCC(NCCc1ccncc1)C2] | NUCC-0176307 | A | ++ | |
| 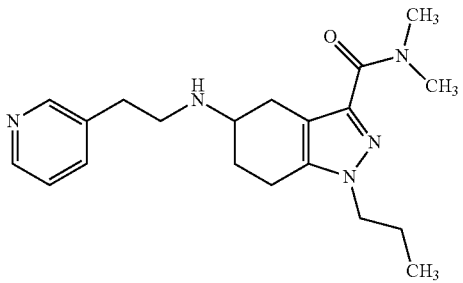 [SMILES: CCCn1nc(C(=O)N(C)C)c2c1CCC(NCCc1cccnc1)C2] | NUCC-0176308 | A | ++ | Agonist |

TABLE 2-continued
Exemplary compounds
| Structure | Molecule Name | Synthetic Route | Effect on Calcium Response | Pharmacology |
|---|---|---|---|---|
| 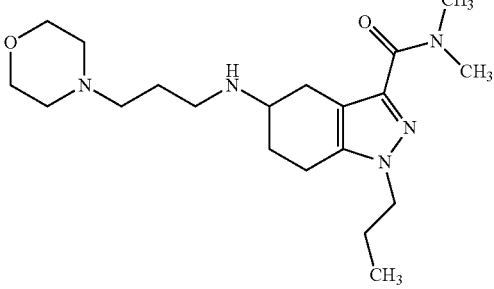 | NUCC-0176309 | A | +++ | |
| 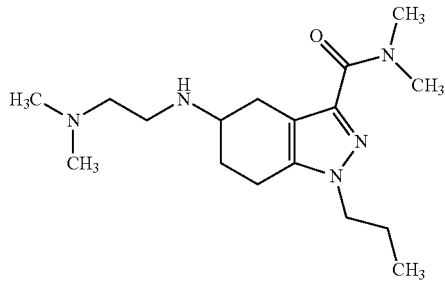 | NUCC-0176310 | A | +++ | |
| 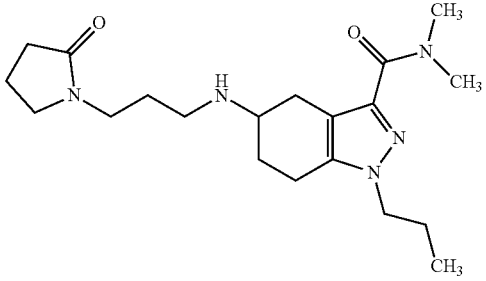 [SMILES: CCCn1nc(C(=O)N(C)C)c2c1CCC(NCCCN1CCCC1=O)C2] | NUCC-0176311 | A | ++ | Agonist |
| 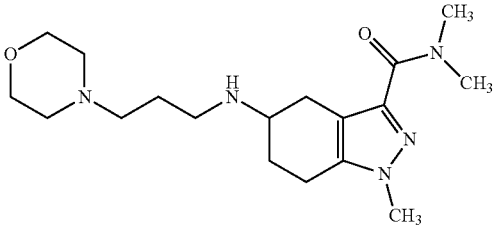 [SMILES: CN(C)C(=O)c1nn(C)c2c1CC(NCCCN1CCOCC1)CC2] | NUCC-0176312 | A | + | |
| 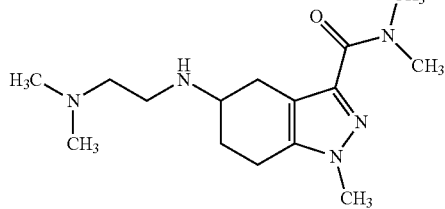 | NUCC-0176313 | A | + | |

TABLE 2-continued
Exemplary compounds
| Structure | Molecule Name | Synthetic Route | Effect on Calcium Response | Pharmacology |
|---|---|---|---|---|
| 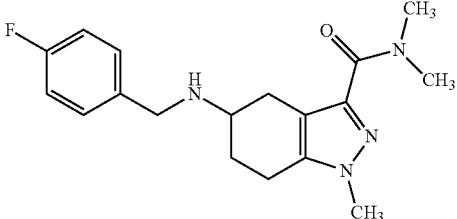 | NUCC-0176314 | A | + | |
| 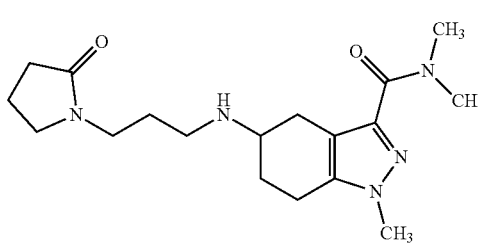 | NUCC-0176315 | A | ++ | |
| 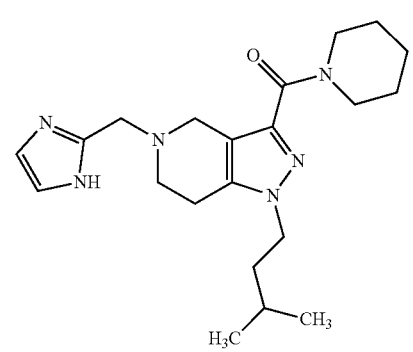 [SMILES: CC(C)CCn1nc(C(=O)N2CCCCC2)c2c1CCN(Cc1ncc[nH]1)C2] | NUCC-0176316 | B | + | |
| 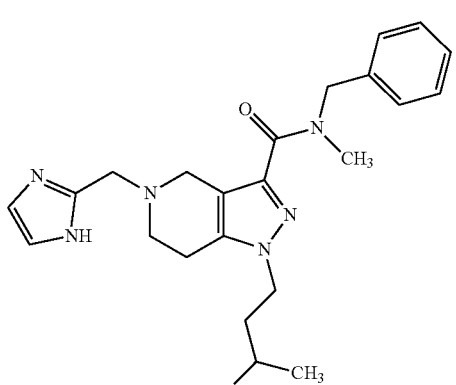 | NUCC-0176317 | B | + | |
| 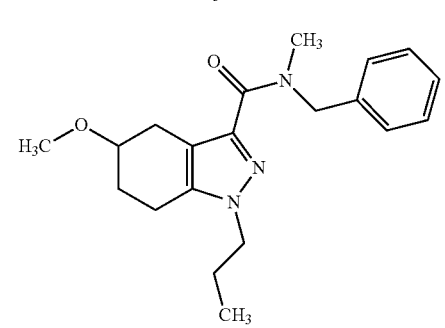 | NUCC-0176318 | C | ++ | |

TABLE 2-continued

Exemplary compounds

| Structure | Molecule Name | Synthetic Route | Effect on Calcium Response | Pharmacology |
|---|---|---|---|---|
| 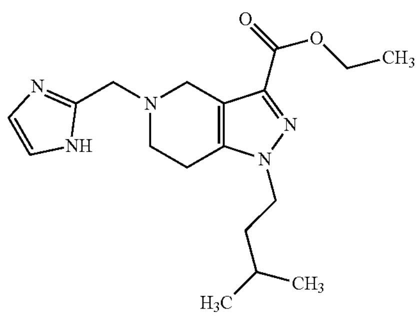 [SMILES: CCOC(=O)c1nn(CCC(C)C)c2c1CN(Cc1ncc[nH]1)CC2] | NUCC-0176319 | B | +++ | |
| 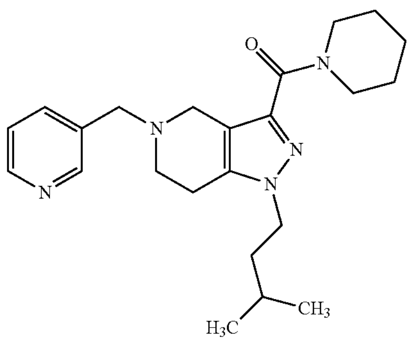 [SMILES: CC(C)CCn1nc(C(=O)N2CCCCC2)c2c1CCN(Cc1cccnc1)C2] | NUCC-0196315 | B | | |
| 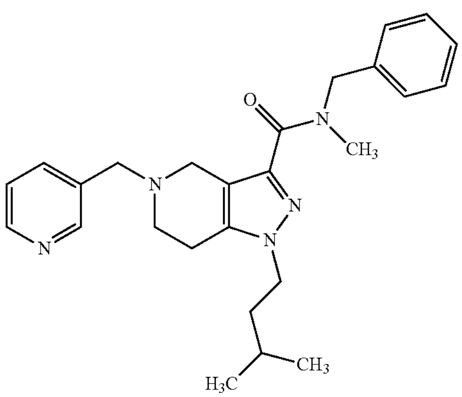 [SMILES: CC(C)CCn1nc(C(=O)N(C)Cc2ccccc2)c2c1CCN(Cc1cccnc1)C2] | NUCC-0196316 | B | | |
| 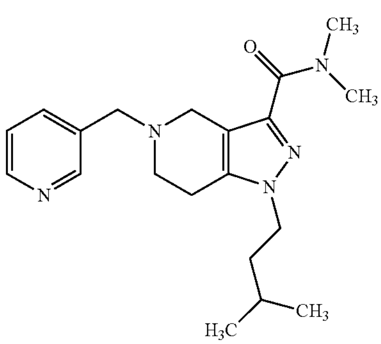 [SMILES: CC(C)CCn1nc(C(=O)N(C)C)c2c1CCN(Cc1cccnc1)C2] | NUCC-0196317 | B | | |

TABLE 2-continued
Exemplary compounds
| Structure | Molecule Name | Synthetic Route | Effect on Calcium Response | Pharmacology |
|---|---|---|---|---|
| 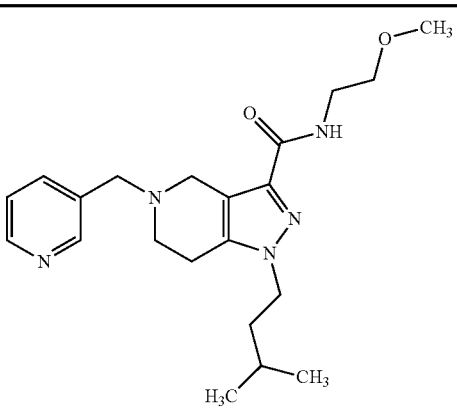 | NUCC-0196318 | B | | |
| 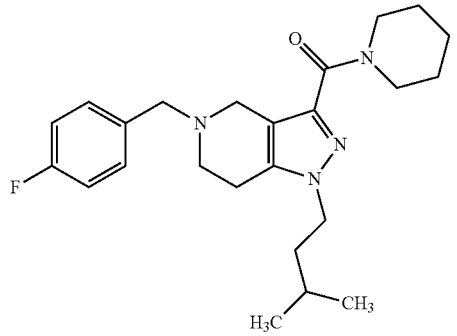 [SMILES: CC(C)CCn1nc(C(=O)N2CCCCC2)c2c1CCN(Cc1ccc(F)cc1)C2] | NUCC-0196319 | B | | |
| 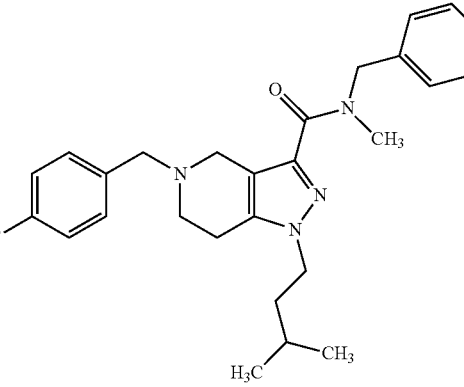 | NUCC-0196320 | B | | |
| 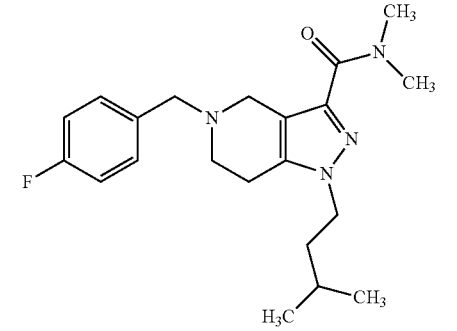 [SMILES: CC(C)CCn1nc(C(=O)N(C)C)c2c1CCN(Cc1ccc(F)cc1)C2] | NUCC-0196321 | B | | |

TABLE 2-continued
Exemplary compounds
| Structure | Molecule Name | Synthetic Route | Effect on Calcium Response | Pharmacology |
|---|---|---|---|---|
| 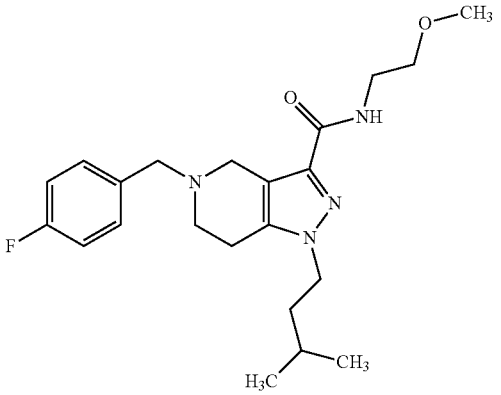 [SMILES: COCCNC(=O)c1nn(CCC(C)C)c2c1CN(Cc1ccc(F)cc1)CC2] | NUCC-0196322 | B | | |
| 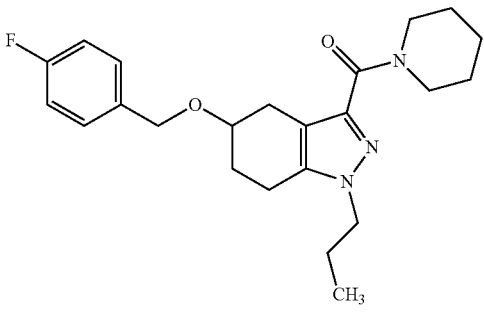 [SMILES: CCCn1nc(C(=O)N2CCCCC2)c2c1CCC(OCc1ccc(F)cc1)C2] | NUCC-0196323 | C | | |
| 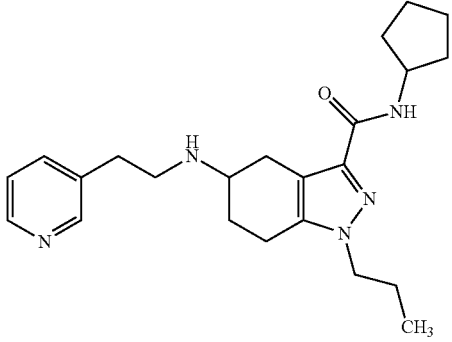 [SMILES: CCCn1nc(C(=O)NC2CCCC2)c2c1CCC(NCCc1cccnc1)C2] | NUCC-0196324 | A | | |
| 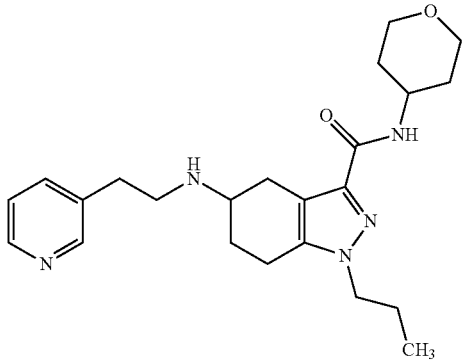 [SMILES: CCCn1nc(C(=O)NC2CCOCC2)c2c1CCC(NCCc1cccnc1)C2] | NUCC-0196325 | A | | |

TABLE 2-continued

Exemplary compounds

| Structure | Molecule Name | Synthetic Route | Effect on Calcium Response | Pharmacology |
| --- | --- | --- | --- | --- |
| 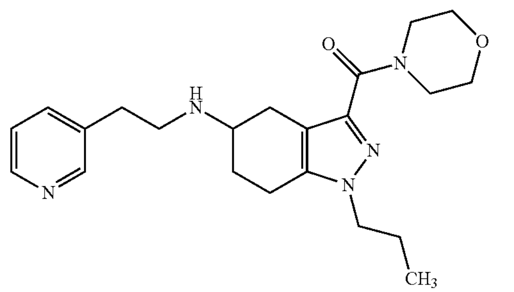 [SMILES: CCCn1nc(C(=O)N2CCOCC2)c2c1CCC(NCCc1cccnc1)C2] | NUCC-0196326 | A | | |
| 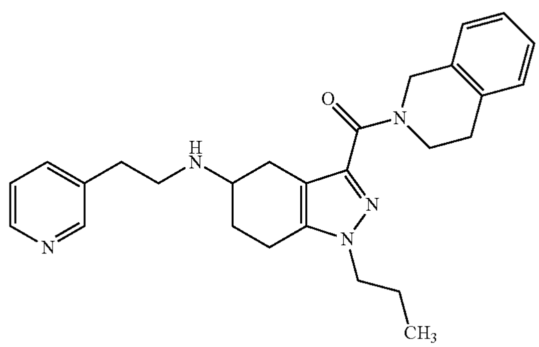 [SMILES: CCCn1nc(C(=O)N2CCc3ccccc3C2)c2c1CCC(NCCc1cccnc1)C2] | NUCC-0196327 | A | | |
| 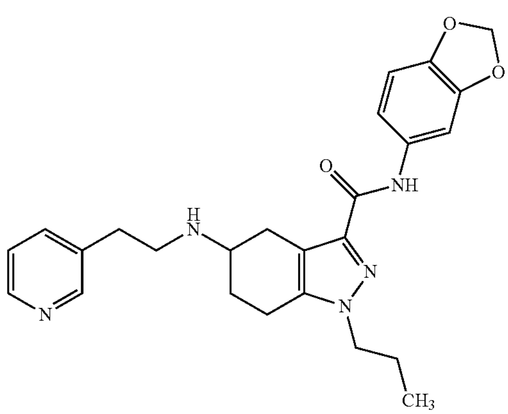 [SMILES: CCCn1nc(C(=O)Nc2ccc3c(c2)OCO3)c2c1CCC(NCCc1cccnc1)C2] | NUCC-0196328 | A | | |
| 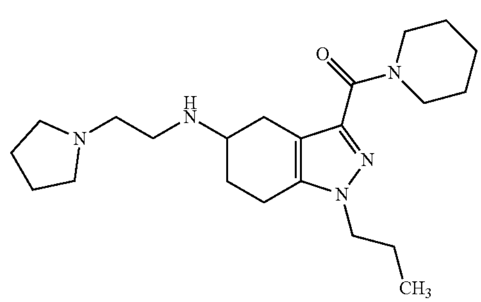 [SMILES: CCCn1nc(C(=O)N2CCCCC2)c2c1CCC(NCCN1CCCC1)C2] | NUCC-0196329 | A | | |

TABLE 2-continued

Exemplary compounds

| Structure | Molecule Name | Synthetic Route | Effect on Calcium Response | Pharmacology |
|---|---|---|---|---|
| 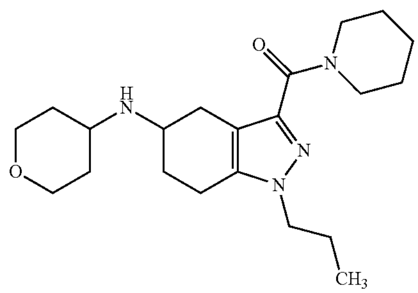 [SMILES: CCCn1nc(C(=O)N2CCCCC2)c2c1CCC(NC1CCOCC1)C2] | NUCC-0196330 | A | | |
| 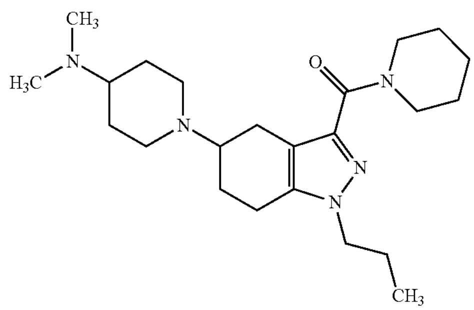 [SMILES: CCCn1nc(C(=O)N2CCCCC2)c2c1CCC(N1CCC(N(C)C)CC1)C2] | NUCC-0196331 | A | | |
| 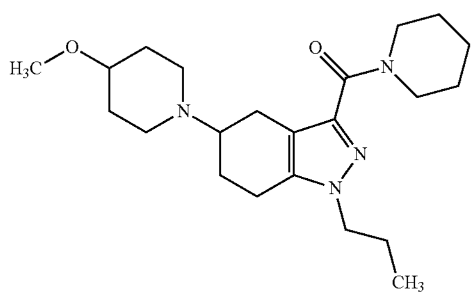 [SMILES: CCCn1nc(C(=O)N2CCCCC2)c2c1CCC(N1CCC(OC)CC1)C2] | NUCC-0196332 | A | | |
| 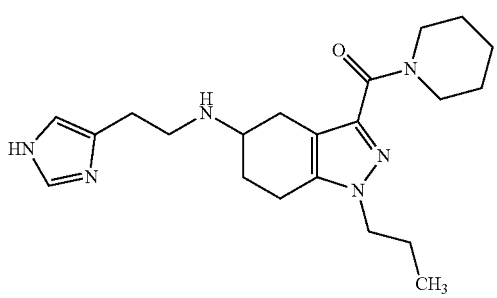 [SMILES: CCCn1nc(C(=O)N2CCCCC2)c2c1CCC(NCCc1c[nH]cn1)C2] | NUCC-0196333 | A | | |
| 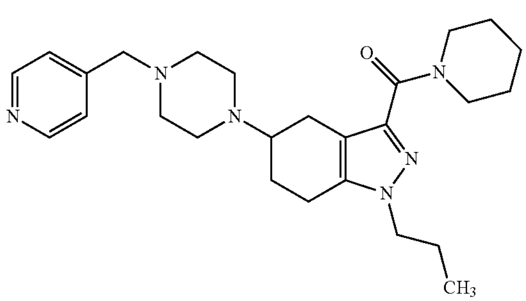 [SMILES: CCCn1nc(C(=O)N2CCCCC2)c2c1CCC(N1CCN(Cc3ccncc3)CC1)C2] | NUCC-0196334 | A | | |

TABLE 2-continued
Exemplary compounds
| Structure | Molecule Name | Synthetic Route | Effect on Calcium Response | Pharmacology |
|---|---|---|---|---|
| 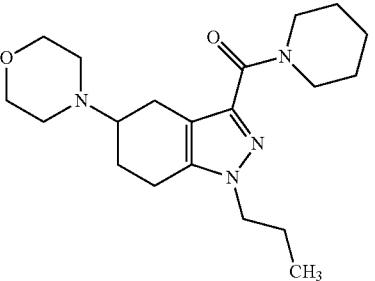 [SMILES: CCCn1nc(C(=O)N2CCCCC2)c2c1CCC(N1CCOCC1)C2] | NUCC-0196335 | A | | |
| 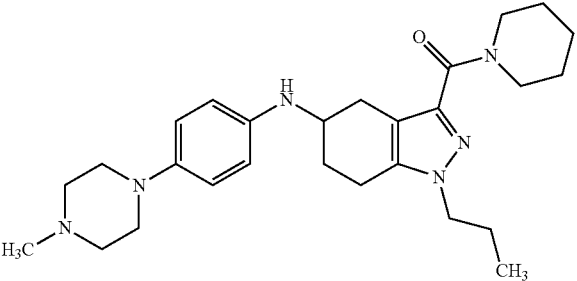 [SMILES: CCCn1nc(C(=O)N2CCCCC2)c2c1CCC(Nc1ccc(N3CCN(C)CC3)cc1)C2] | NUCC-0196336 | A | | |
| 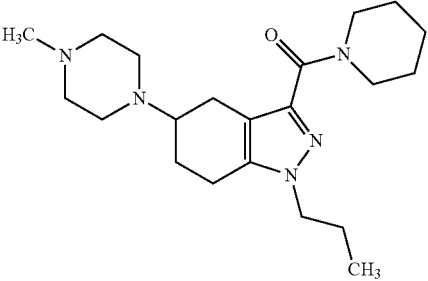 [SMILES: CCCn1nc(C(=O)N2CCCCC2)c2c1CCC(N1CCN(C)CC1)C2] | NUCC-0196337 | A | | |
| 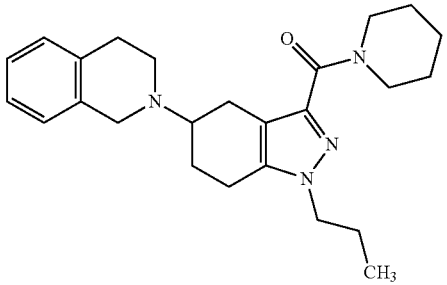 [SMILES: CCCn1nc(C(=O)N2CCCCC2)c2c1CCC(N1CCc3ccccc3C1)C2] | NUCC-0196338 | A | | |
| 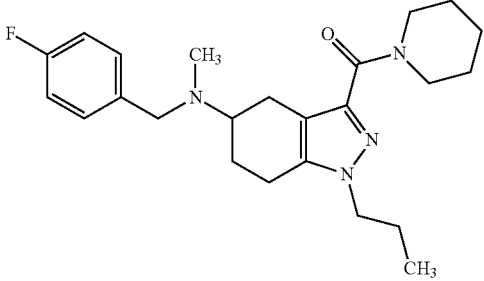 [SMILES: CCCn1nc(C(=O)N2CCCCC2)c2c1CCC(N(C)Cc1ccc(F)cc1)C2] | NUCC-0196339 | A | | |

Example 10

Chemical Synthesis

General

Chemical reagents were obtained from commercial suppliers and used without further purification unless otherwise stated. DCM, THF and DMF were purified by passage through a bed of activated alumina. Polymer supported reagents MP-Triacetoxyborohydride (2.36 mmol/g), MP-Cyanoborohydride (2.22 mmol/g) and PS-Benzaldehyde (1.09 mmol/g) were purchased from Biotage. Normal-phase flash column chromatography was performed using Biotage KP-Sil 50 μm silica gel columns and ACS grade solvents on a Biotage Isolera flash purification system. Analytical thin layer chromatography (TLC) was performed on EM Reagent 0.25 mm silica gel 60 $F_{254}$ plates and visualized by UV light. Liquid chromatography/mass spectrometry (LCMS) was performed on a Waters Acquity-H UPLC system with a 2.1 mm×50 mm, 1.7 μm, reversed phase BEH C18 column and LCMS grade solvents. A gradient elution from 95% water+ 0.1% formic acid/5% acetonitrile+0.1% formic acid to 95% acetonitrile+0.1% formic acid/5% water+0.1% formic acid over 2 min plus a further minute continuing this mixture at a flow rate of 0.85 mL/min was used as the eluent. Total ion current traces were obtained for electrospray positive and negative ionization (ESI+/ESI−). Proton ($^1$H), and carbon ($^{13}$C) NMR spectra were recorded on a Bruker Avance III w/direct cryoprobe spectrometer. Chemical shifts were reported in ppm (δ) and were referenced using residual non-deuterated solvent as an internal standard. The chemical shifts for $^1$H NMR and $^{13}$C NMR are reported to the second decimal place. Proton coupling constants are expressed in hertz (Hz). The following abbreviations were used to denote spin multiplicity for proton NMR: s=singlet, d=doublet, t=triplet, q=quartet, m=multiplet, br. s=broad singlet, dd=doublet of doublets, dt=doublet of triplets, quin=quintet, tt=triplet of triplets. In some cases, overlapping signals occurred in the $^{13}$C NMR spectra.

General Synthetic Scheme A.
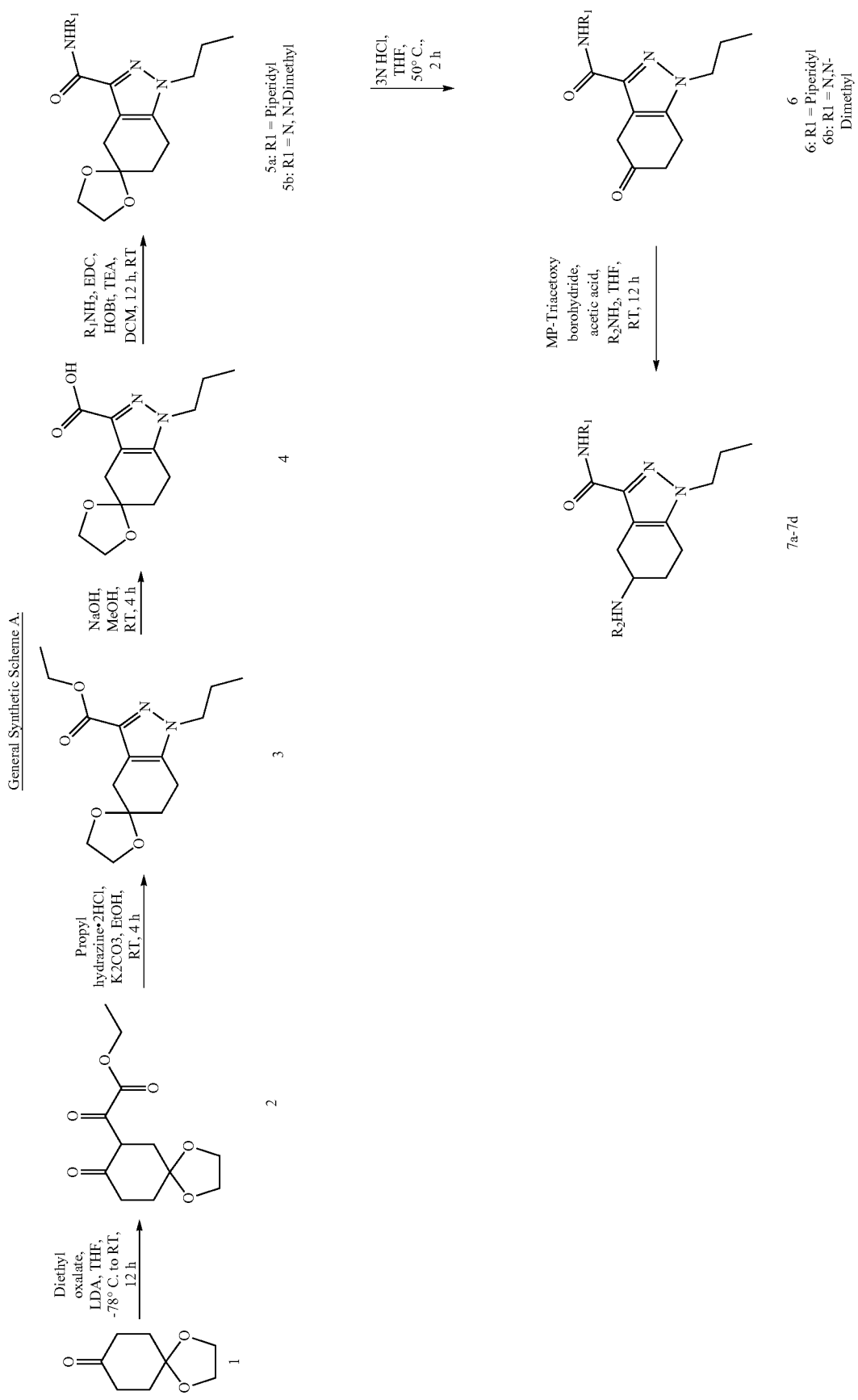

Preparation of Intermediates and Final Compounds Shown in Scheme A:

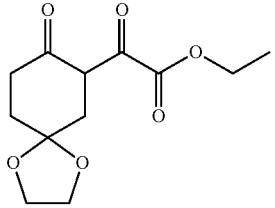 [SMILES: CCOC(=O)C(=O)C1CC2(CCC1=O)OCCO2]

Ethyl 2-(8-hydroxy-1,4-dioxaspiro(4.5)dec-7-en-7-yl)-2-oxoacetate (2): To a solution of 1,4-dioxaspiro(4.5)decan-8-one 1 (7.81 g, 50 mmol) in anhydrous THF (75 mL) cooled to −78° C. under a $N_2$ atmosphere was added LDA (27.5 mL, 55 mmol). After stirring for 15 minutes, diethyl oxalate (7.47 mL, 55 mmol) was added in portions over 10 min. The reaction was gradually warmed to RT and stirred for 16 h. The reaction mixture was quenched with 1N HCl and the resulting mixture was extracted with EtOAc, washed with brine and dried over anhydrous $Na_2SO_4$, filtered and concentrated in vacuo. The residue was purified by silica gel flash chromatography (0-100% EtOAc in Hexanes) to yield the Ethyl 2-(8-hydroxy-1,4-dioxaspiro(4.5)dec-7-en-7-yl)-2-oxoacetate 2 (4.2 g, 33%) as a thick yellow oil. MS (ESI): mass calcd. for $C_{12}H_{16}O_6$, 256.09; m/z found, 257.16 (M+H)+; $^1$H NMR (500 MHz, $CDCl_3$) δ 1.37 (t, J=7.17 Hz, 3 H), 1.91 (t, J=6.87 Hz, 2 H), 2.68 (t, J=6.87 Hz, 2 H), 2.74 (s, 2 H), 3.97 -4.02 (m, 4 H), 4.33 (q, J=7.22 Hz, 2 H), 15.35 (s, 1 H),.

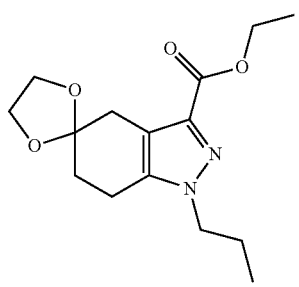 [SMILES: CCCn1nc(C(=O)OCC)c2c1CCC1(C2)OCCO1]

Ethyl 1'-propyl-1',4',6',7'-tetrahydrospiro((1,3)dioxolane-2,5'-indazole)-3'-carboxylate (3): Propylhydrazine.2HCl (2 g, 13.6 mmol) was added to a solution of ethyl 2-oxo-2-(8-oxo-1,4-dioxaspiro(4.5)decan-7-yl)acetate 2 (3.49 g, 13.6 mmol) and $K_2CO_3$ (3.76 g, 27.2 mmol) in EtOH (84 ml). The reaction mixture was stirred at RT for 4 h and then concentrated in vacuo. The residue was re-dissolved in EtOAc and $H_2O$ and the layers separated. The aqueous layer was extracted with EtOAc and the combined organic layer was washed with brine, dried over anhydrous $Na_2SO_4$, filtered and concentrated in vacuo. The residue obtained was purified by silica gel chromatography (0-60% EtOAc in Hexanes) to give ethyl 1'-propyl-1',4',6',7'-tetrahydrospiro((1,3)dioxolane-2,5'-indazole)-3'-carboxylate 3 (3.3 g, 82%) as a thick oil. MS (ESI): mass calcd. for $C_{15}H_{22}N_2O_4$, 294.16; m/z found, 295.41 (M+H)+; $^1$H NMR (500 MHz, $CDCl_3$) δ 0.92 (t, J=7.48 Hz, 3 H), 1.34-1.40 (m, 3 H), 1.86 (m, 2 H), 1.98 (t, J=6.56 Hz, 2 H), 2.78 (t, J=6.56 Hz, 2 H), 2.98 (s, 2 H), 3.97-4.08 (m, 6 H), 4.37 (q, J=7.22 Hz, 2 H).

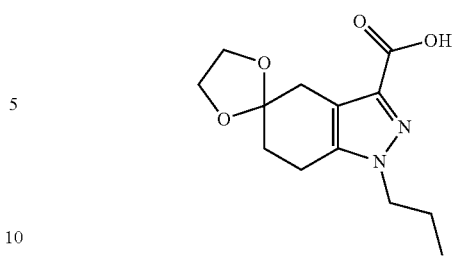

1'-Propyl-1',4',6',7'-tetrahydrospiro((1,3)dioxolane-2,5'-indazole)-3'-carboxylic acid (4): To a mixture of ethyl 1'-propyl-1',4',6',7'-tetrahydrospiro((1,3)dioxolane-2,5'-indazole)-3'-carboxylate 3 (3.3 g, 11.21 mmol) in EtOH (50 ml) was added a 2M solution of NaOH (50 mL) and the reaction mixture stirred at RT for 4 h. The EtOH was evaporated and the aqueous mixture was washed with diethyl ether. The pH of the aqueous layer was adjusted to 5-6. The aqueous layer was then extracted with EtOAc (x3). The combined organic extract was dried using anhydrous Na2SO4, filtered and concentrated under educed pressure to yield 1'-propyl-1',4',6',7'-tetrahydrospiro((1,3)dioxolane-2,5'-indazole)-3'-carboxylic acid 4 (2.5 g, 84%) as an off-white solid. MS (ESI): mass calcd. for $C_{13}H_{18}N_2O_4$, 266.13; m/z found, 267.37 (M+H)+; $^1$H NMR (500 MHz, $CD_3OD$) δ (t, J=7.32 Hz, 3 H), 1.79-1.90 (m, 2 H), 1.94-2.00 (m, 2 H), 2.81 (t, J=6.56 Hz, 2 H), 2.90 (s, 2H), 3.99-4.06 (m, 6 H).

General Procedure I for the Synthesis of Amides 5a, 5b

To a solution carboxylic acid 4a (1.0 equiv) in DCM (0.1M) was added EDC (1.1 equiv) and HOBT (1.0 equiv). The reaction mixture was stirred at RT for 30 min and then the respective amine $R_1NH_2$ (1.0 equiv) and TEA (1.1 equiv) were added to it. The mixture was then stirred at RT for 12 h, diluted with DCM and washed with $H_2O$ and brine. The organic extract was dried over with anhydrous $Na_2SO_4$, filtered and concentrated in vacuo to give a residue which was purified by a short silica gel plug (DCM then 10% MeOH in DCM) to give the amides 5a, 5b.

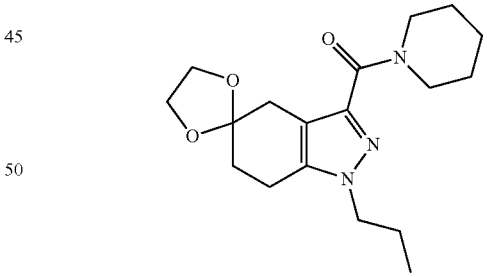

Piperidin-1-yl(1'-propyl-1',4',6',7'-tetrahydrospiro((1,3)dioxolane-2,5'-indazol)-3'-yl)methanone (5a): Prepared according to General procedure I using carboxylic acid 4 (1.5 g, 5.63 mmol) to afford piperidin-1-yl(1'-propyl-1',4',6',7'-tetrahydrospiro((1,3)dioxolane-2,5'-indazol)-3'-yl) methanone 5a (0.8 g, 43%) as an off-white solid. MS (ESI): mass calcd. for $C_{18}H_{27}N_3O_3$, 333.21; m/z found, 334.40 (M+H)+; $^1$H NMR (500 MHz, $CDCl_3$) δ 0.93 (t, J=7.32 Hz, 3 H), 1.54-1.60 (m, 2 H), 1.62-1.69 (m, 4 H), 1.83 (sxt, J=7.32 Hz, 2 H), 1.99 (t,J=6.56 Hz, 2 H), 2.76 (t, J=6.56 Hz, 2 H), 2.90 (s, 2 H), 3.66 (br. s., 2 H), 3.83 (br. s., 2 H), 3.89-3.95 (m, 2 H), 3.96-4.06 (m, 4 H).

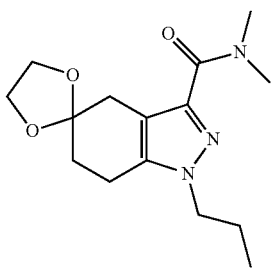 [SMILES: CCCn1nc(C(=O)N(C)C)c2c1CCC1(C2)OCCO1]

N,N-dimethyl-1'-propyl-1',4',6',7'-tetrahydrospiro((1,3)di-oxolane-2,5'-indazole)-3'-carboxamide (5b): Prepared according to General procedure I using carboxylic acid 4 (0.3 g, 1.13 mmol) to afford N,N-dimethyl-1'-propyl-1',4',6',7'-tetrahydrospiro((1,3)dioxolane-2,5'-indazole)-3'-carboxamide 5b (145 mg, 44%) as a pale yellow solid. MS (ESI): mass calcd. for $C_{15}H_{23}N_3O_3$, 293.17; m/z found, 294.30 (M+H)+; $^1$H NMR (500 MHz, CDCl$_3$) δ 0.93 (t, J=7.32 Hz, 3 H), 1.83 (sxt, J=7.32 Hz, 2 H), 1.99 (t, J=6.56 Hz, 2 H), 2.77 (t, J=6.56 Hz, 2 H), 2.93 (s, 2 H), 3.05 (br. s., 3 H), 3.32 (br. s., 3 H), 3.92 (t, J=7.32 Hz, 2 H), 3.97-4.07 (m, 4 H).

General Procedure II for the Synthesis of Ketones 6a, 6b

Amides 5a or 5b (1.0 equiv) were dissolved in THF (0.8M) then 3N HCl (5.0 equiv) was added to the mixture. The resulting solution was heated at 50° C. for 2 h (reaction ~95% complete as analyzed by LCMS). The solvents were evaporated and EtOAc was added. The organic layer was washed with saturated NaHCO$_3$ and H$_2$O. The combined organic layer was dried over anhydrous Na2SO4 and evaporated in vacuo to give the crude product which was purified by a short silica gel plug using 0-10% MeOH in DCM to give the products 6a, 6b.

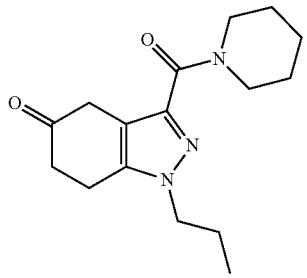 [SMILES: CCCn1nc(C(=O)N2CCCCC2)c2c1CCC(=O)C2]

3-(Piperidine-1-carbonyl)-1-propyl-6,7-dihydro-1H-indazol-5(4H),-one (6a): Prepared according to General procedure II using 5a (1.3 g, 3.9 mmol) to afford 3-(piperidine-1-carbonyl)-1-propyl-6,7-dihydro-1H-indazol-5(4H),-one 6a (0.75 g, 67%) as a clear waxy solid. MS (ESI): mass calcd. for $C_{16}H_{23}N_3O_2$, 289.18; m/z found, 290.31 (M+H)+.

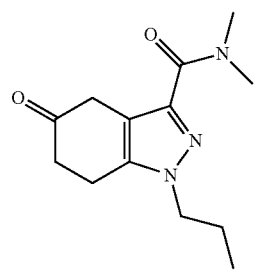 [SMILES: CCCn1nc(C(=O)N(C)C)c2c1CCC(=O)C2]

N,N-dimethyl-5-oxo-1-propyl-4,5,6,7-tetrahydro-1H-indazole-3-carboxamide (6b): Prepared according to General procedure II using 5b (320 mg, 1.1 mmol) to afford N,N-dimethyl-5-oxo-1-propyl-4,5,6,7-tetrahydro-1H-indazole-3-carboxamide 6b (230 mg, 85%) as yellow waxy solid. MS (ESI): mass calcd. for $C_{13}H_{19}N_3O_2$, 249.15; m/z found, 250.24 (M+H)+.

General Procedure III for the Synthesis of Compounds 7a-7d

To a solution of 6a or 6b in THF (0.1M) was added amine R$_2$NH$_2$ (1.2 equiv) and acetic acid (1.2 equiv). The mixture was stirred at RT for 15 min and then MP-Triacetoxyborohydride (2.0 equiv) or MP-Cyanoborohydride (2.0 equiv) was added and the reaction stirred at RT for 12 h. To the reaction mixture was added PS-Benzaldehyde (1.5 equiv) and the scavenging reaction mixture was stirred at RT for 4 h. The solution was filtered and the filtrate was concentrated to dryness to yield a residue which was purified by reversed phase chromatography using C$_{18}$ column (ACN/H2O) to afford the target compounds. In some cases, the compounds could be purified by normal phase chromatography using silica gel (DCM/MeOH),. Acetate salts were obtained for some compounds (NUCC-0000390, NUCC-0054118 and NUCC-0054121) when MP-Triacetoxyborohydride was used as the reducing agent. The formation of the acetate salt could be attributed to hydrolysis of an equivalent of triacetoxyborohydride by the water generated from imine formation prior to reduction.

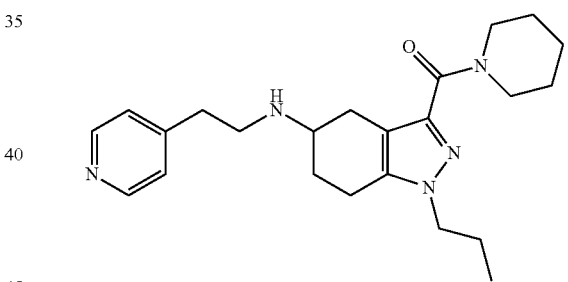

Piperidin-1-yl(1-propyl-5-((2-(pyridin-4-yl)ethyl)amino)-4,5,6,7-tetrahydro-1H-indazol-3-yl)methanone (7a, NUCC-0000390): Prepared according to General procedure III using 6a (100 mg, 0.35 mmol) to afford 7a or NUCC-0000390 (40 mg, 25%) as pale yellow solid (acetate salt). MS (ESI): mass calcd. for $C_{23}H_{33}N_5O$, 395.27; m/z found, 396.40 (M+H)+; $^1$H NMR (500 MHz, CDCl$_3$) δ 0.90 (t, J=7.48 Hz, 3 H), 1.21 (t, J=7.02 Hz, 1 H), 1.56 (br. s., 2 H), 1.63-1.69 (m, 3 H), 1.71-1.77 (m, 1 H), 1.80 (q, J=7.32 Hz, 2 H), 2.05 (s, 3 H), 2.41 (dd, J=15.56, 8.54 Hz, 1 H), 2.53-2.62 (m, 1 H), 2.63-2.72 (m, 1 H), 2.79-2.88 (m, 2 H), 2.94-3.00 (m, 3 H), 3.03-3.09 (m, 4 H), 3.42-3.53 (m, 1 H), 3.67 (br. s., 2 H), 3.78 (br. s., 2 H), 3.90 (td, J=7.17, 1.53 Hz, 2 H), 7.11-7.22 (m, 2 H), 8.47-8.58 (m, 2 H); $^{13}$C NMR (126 MHz, CDCl$_3$) δ 11.34, 19.93, 21.49, 23.60, 24.92, 27.74, 28.86, 35.53, 43.41, 47.16, 48.34, 50.87, 53.80, 115.97, 124.35, 137.95, 142.56, 149.06, 149.70, 163.89, 174.96.

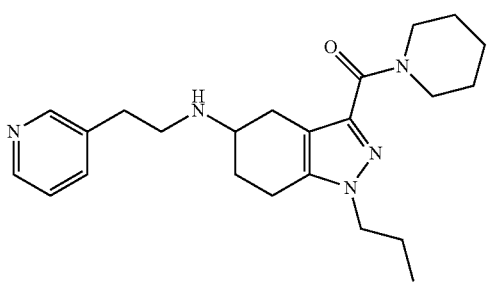 [SMILES: CCCn1nc(C(=O)N2CCCCC2)c2c1CCC(NCCc1cccnc1)C2]

Piperidin-1-yl(1-propyl-5-((2-(pyridin-3-yl)ethyl)amino)-4,5,6,7-tetrahydro-1H-indazol-3-yl)methanone (7b, NUCC-0054118): Prepared according to General procedure III using 6a (100 mg, 0.35 mmol) to afford 7b or NUCC-0054118 (45 mg, 30%) as white solid (acetate salt). MS (ESI): mass calcd. for $C_{23}H_{33}N_5O$, 395.27; m/z found, 396.50 (M+H)+; $^1$HNMR (500 MHz, CD$_3$OD) δ 0.91 (t, J=7.48 Hz, 3 H), 1.59 (br. s., 2 H), 1.64 (br. s., 2 H), 1.69-1.74 (m, 2 H), 1.77-1.85 (m, 3 H), 1.94 (s, 3 H), 2.22-2.30 (m, 1 H), 2.50 (dd, J=15.26, 9.16 Hz, 1 H), 2.69-2.77 (m, 1 H), 2.83-2.90 (m, 1 H), 2.94-3.01 (m, 2 H), 3.06 (dd, J=15.56, 4.58 Hz, 1 H), 3.15-3.21 (m, 2 H), 3.23-3.28 (m, 1 H), 3.65-3.80 (m, 4 H), 4.00 (t, J=7.02 Hz, 2 H), 7.42 (dd, J=7.93, 4.88 Hz, 1 H), 7.80 (d, J=7.93Hz, 1 H), 8.44 (dd, J=4.88, 1.53 Hz, 1 H), 8.48 (s, 1 H); $^{13}$C NMR (126 MHz, CD$_3$OD) δ 11.48, 20.42, 24.48, 25.72, 25.96, 26.92, 27.10, 28.00, 31.12, 44.70, 47.46, 51.92, 56.00, 115.00, 125.67, 134.90, 138.82, 139.60, 143.31, 149.08, 150.54, 165.21.

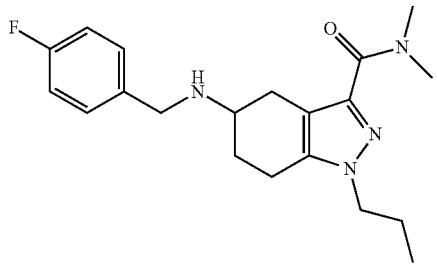 [SMILES: CCCn1nc(C(=O)N(C)C)c2c1CCC(NCc1ccc(F)cc1)C2]

5-((4-Fluorobenzyl)amino)—N,N-dimethyl-1-propyl-4,5,6,7-tetrahydro-1H-indazole-3-carboxamide (7c, NUCC-0054121): Prepared according to General procedure III using 6b (150 mg, 0.6 mmol) to afford 7c or NUCC-0054121 (60 mg, 28%) as light pink solid (acetate salt). MS (ESI): mass calcd. for $C_{20}H_{27}FN_4O$, 358.22; m/z found, 359.40 (M+H)+; $^1$HNMR (500 MHz, CD$_3$OD) δ 0.88-0.93 (m, 3 H), 1.80-1.87 (m, 3 H), 1.95 (s, 3 H), 2.22-2.33 (m, 1 H), 2.52 (dd, J=15.56, 9.46 Hz, 1 H), 2.64-2.74 (m, 1 H), 2.82-2.92 (m, 1 H), 3.08 (s, 3 H), 3.10-3.24 (m, 2 H), 3.26 (s, 3 H), 4.00 (t, J=7.02 Hz, 2 H), 4.05 (s, 2 H), 7.08-7.17 (m, 2 H), 7.42-7.51 (m, 2 H); $^{13}$C NMR (126 MHz, CD$_3$OD) δ 11.48, 20.67, 22.97, 24.50, 27.10, 27.95, 36.10, 39.60, 50.26, 51.86, 55.09, 116.12, 116.71, 116.88, 132.55, 132.61, 139.94, 143.29, 163.37, 167.02.

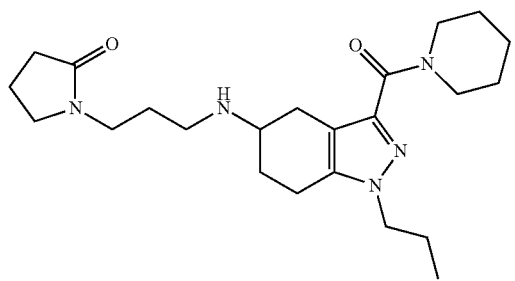 [SMILES: CCCn1nc(C(=O)N2CCCCC2)c2c1CCC(NCCCN1CCCC1=O)C2]

1-(3-((3-(Piperidine-1-carbonyl)-1-propyl-4,5,6,7-tetrahydro-1H-indazol-5-yl)amino)propyl)pyrrolidin-2-one (7d, NUCC-0054120): Prepared according to General procedure III using 6a (100 mg, 0.35 mmol) to afford 7d or NUCC-0054120 (55 mg, 45%) as waxy pink solid. MS (ESI): mass calcd. for $C_{23}H_{37}N_5O_2$, 358.22; m/z found, 359.40 (M+H)+; $^1$H NMR (500 MHz, CD$_3$OD) δ 0.90 (t, J=7.48 Hz, 3 H), 1.58 (br. s., 2 H), 1.62-1.69 (m, 3 H), 1.69-1.75 (m, 3 H), 1.75-1.80 (m, 2 H), 1.80-1.86 (m, 2 H), 2.03-2.09 (m, 2 H), 2.09-2.17 (m, 1 H), 2.27-2.34 (m, 1 H), 2.38 (t, J=8.09 Hz, 2 H), 2.64-2.68 (m, 2 H), 2.77-2.84 (m, 1H), 2.86-2.94 (m, 2 H), 3.36 (t, J=6.87 Hz, 2 H), 3.45-3.50 (m, 2 H), 3.67 (br. s., 4 H), 3.98 (t, J=7.02 Hz, 2 H); $^{13}$C NMR (126 MHz, CD$_3$OD) δ 11.48, 19.00, 20.87, 24.55, 25.72, 27.04, 27.98, 28.23, 29.49, 32.10, 41.44, 44.51, 44.99, 51.68, 55.11, 116.45, 140.55, 143.53, 166.01, 177.97.

General Synthetic Scheme B.

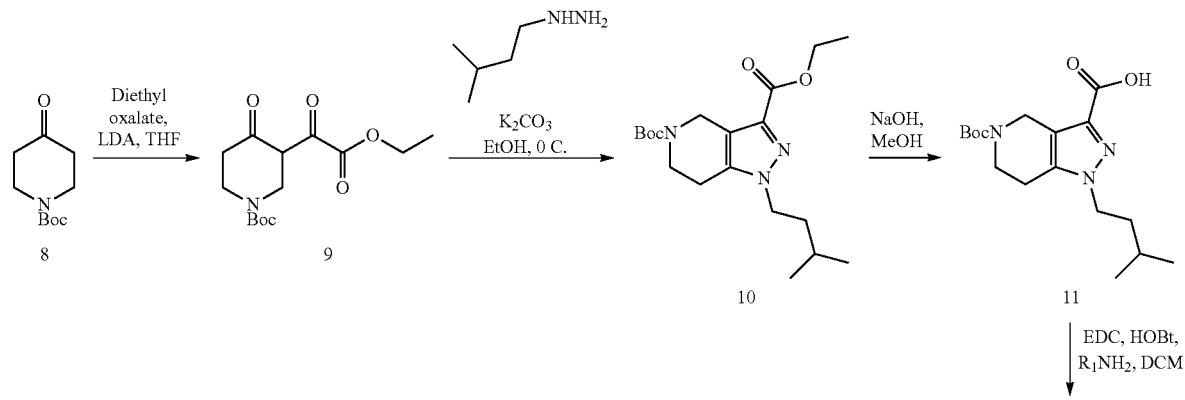

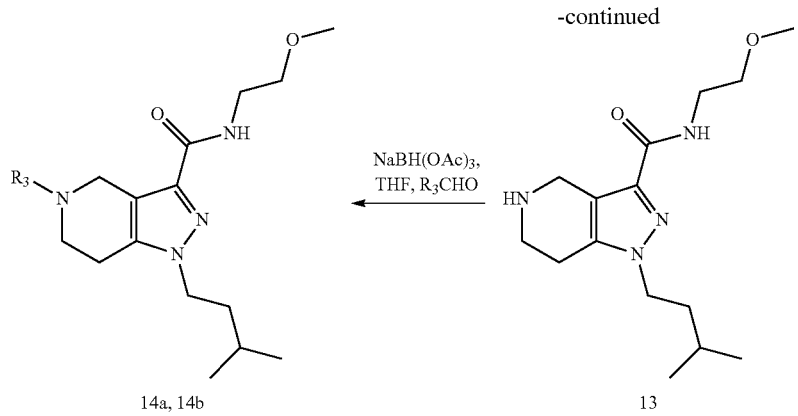

14a, 14b         13

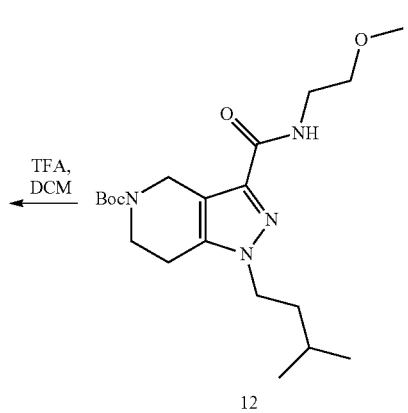

12

Preparation of Intermediates and Final Compounds Shown in Scheme B:

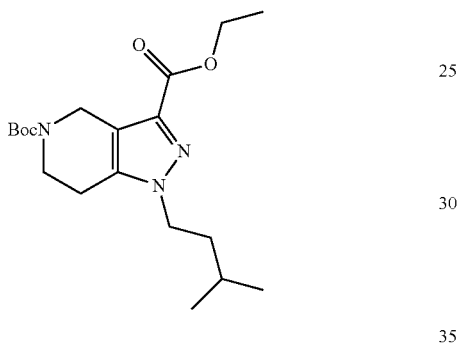

5-tert-Butyl 3-ethyl 1-isopentyl-6,7-dihydro-1H-pyrazolo(4,3-c)pyridine-3,5(4H),-dicarboxylate (10): To a solution of tert-butyl 4-oxopiperidine-1-carboxylate 8 (2 g, 10.04 mmol) in anhydrous THF (15 mL) cooled to −78° C. under a $N_2$ atmosphere was added LDA (5.32 mL, 10.64 mmol) gradually. After stirring for 30 minutes, diethyl oxalate (1.445 mL, 10.64 mmol) was added. The reaction was gradually warmed to RT and stirred for 16 h. The reaction mixture was quenched with 1N HCl and the resulting mixture was extracted with EtOAc, washed with brine and dried over anhydrous $Na_2SO_4$. The solution was filtered and concentrated in vacuo to give tert-butyl 3-(2-ethoxy-2-oxoacetyl)-4-oxopiperidine-1-carboxylate 9 (2.1 g, 70%) as a thick yellow oil which was immediately taken to the next step. MS (ESI): mass calcd. for $C_{14}H_{21}NC_6$, 299.14; m/z found, 300.30 (M+H)+. Isopentylhydrazine.2HCl (0.84 g, 4.8 mmol) was added to a solution of tert-butyl 3-(2-ethoxy-2-oxoacetyl)-4-oxopiperidine-1-carboxylate 9 (1.2 g, 4.01 mmol) and $K_2CO_3$ (0.55 g, 4 mmol) in EtOH (12 ml) The reaction mixture was stirred at RT for 4 h and then the solvent was concentrated in vacuo. The residue was re-dissolved in EtOAc/$H_2O$ and the layers separated. The aqueous layer was extracted with EtOAc and the combined organic extract was washed with brine, dried over anhydrous Na2SO4, filtered and concentrated in vacuo. The residue obtained was purified by silica gel chromatography (0-50% EtOAc in Hexanes) to afford 5-tert-butyl 3-ethyl 1-isopentyl-6,7-dihydro-1H-pyrazolo(4,3-c)pyridine-3,5(4H),-dicarboxylate 10 (550 mg, 38%) as a yellow waxy solid. MS (ESI): mass calcd. for $C_{19}H_{31}N_3O_4$, 365.23; m/z found, 366.46 (M+H)+; $^1$H NMR (500 MHz, CDCl$_3$) δ 0.93 (s, 3 H), 0.94 (s, 3 H), 1.38 (t, J=7.17 Hz, 3 H), 1.48 (s, 9 H), 1.61-1.63 (m, 1 H), 1.69-1.74 (m, 2 H), 2.68 (br. s., 2 H), 3.72 (br. s., 2 H), 4.04-4.10 (m, 2 H), 4.39 (d, J=7.32 Hz, 2 H), 4.60 (s, 2 H).

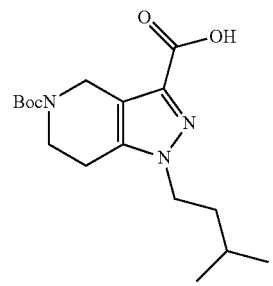 [SMILES: CC(C)CCn1nc(C(=O)O)c2c1CCN(C(=O)OC(C)(C)C)C2]

5-(tert-Butoxycarbonyl)-1-isopentyl-4,5,6,7-tetrahydro-1H-pyrazolo(4,3-c)pyridine-3-carboxylic acid (11): A solution of 5-tert-butyl 3-ethyl 1-isopentyl-6,7-dihydro-1H-pyrazolo(4,3-c)pyridine-3,5(4H),-dicarboxylate 10 (1.2 g, 3.28 mmol) in EtOH (16 mL) was treated with 2M NaOH (8 mL). The reaction mixture was stirred at RT for 2 h and then the solvent concentrated in vacuo. The residue was dissolved in $H_2O$ and washed with diethyl ether. The aqueous layer was acidified to pH 6-7 using 1N HCl and then extracted using EtOAc (×2). The combined organic extract was dried over anhydrous Na2SO4, filtered and concentrated in vacuo to afford 5-(tert-butoxycarbonyl)-1-isopentyl-4,5,6,7-tetrahydro-1H-pyrazolo(4,3-c)pyridine-3-carboxylic acid 11 (1.03 g, 93%) as a white solid. MS (ESI): mass calcd. for $C_{17}H_{27}N_3O_4$, 337.20; m/z found, 338.40 (M+H)+; $^1$H NMR (500 MHz, DMSO-d$_6$) δ 0.90 (s, 2 H), 0.91 (s, 3 H), 1.42 (s, 9 H), 1.51-1.55 (m, 1 H), 1.60 (q, J=7.02 Hz, 2 H), 2.64 (dd, J=4.43, 2.59 Hz, 2 H), 3.58 (t, J=5.80 Hz, 2 H), 3.99 (t, J=7.32 Hz, 2 H), 4.44 (s, 2 H).

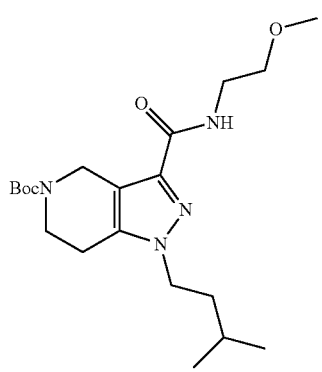 [SMILES: COCCNC(=O)c1nn(CCC(C)C)c2c1CN(C(=O)OC(C)(C)C)CC2]

tert-Butyl 1-isopentyl-3-((2-methoxyethyl)carbamoyl)-6,7-dihydro-1H-pyrazolo(4,3-c)pyridine-5(4H),-carboxylate (12): Prepared according to General procedure I using carboxylic acid 11 (260 mg, 0.77 mmol) to afford tent-butyl 1-isopentyl-3-((2-methoxyethyl)carbamoyl)-6,7-dihydro-1H-pyrazolo(4,3 -c)pyridine-5 (4H),-carboxylate 12 (240 mg, 79%) as a waxy solid. MS (ESI): mass calcd. for $C_{20}H_{34}N_4O_4$, 394.26; m/z found, 395.50 (M+H)+; $^1$H NMR (500 MHz, CDCl$_3$) δ 0.94 (s, 3 H), 0.96 (s, 3 H), 1.45-1.50 (m, 9 H), 1.56-1.62 (m, 1 H), 1.66-1.69 (m, 2 H), 2.66 (t,J=5.04 Hz, 2 H), 3.39 (s, 3 H), 3.52-3.57 (m, 2 H), 3.57-3.62 (m, 2 H), 3.71 (t, J=4.88 Hz, 2 H), 3.94-4.02 (m, 2 H), 4.66 (s, 2 H).

General Procedure IV for the Synthesis of Amines 13

A solution of amide 12 in DCM:TFA (2:1) was stirred at RT for 2 h and then the solvent concentrated in vacuo. The products were dried under high vacuum and used in the subsequent steps without further purification.

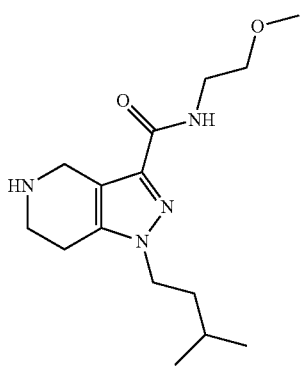 [SMILES: COCCNC(=O)c1nn(CCC(C)C)c2c1CNCC2]

1-Isopentyl-N-(2-methoxyethyl)-4,5,6,7-tetrahydro-1H-pyrazolo(4,3-c)pyridine-3-carboxamide (13): Prepared according to General procedure IV using amide 12 (230 mg, 0.58 mmol) to afford 1-isopentyl-N-(2-methoxyethyl)-4,5,6,7-tetrahydro-1H-pyrazolo(4,3-c)pyridine-3-carboxamide 13 (150 mg, 87%) as a semi solid. MS (ESI): mass calcd. for $C_{15}H_{26}N_4O_2$, 294.21; m/z found, 295.55 (M+H)+; $^1$H NMR (500 MHz, CDCl$_3$) δ 0.97 (s, 3 H), 0.99 (s, 3 H), 1.62 (dt, J=13.35, 6.60 Hz, 1 H), 1.69-1.78 (m, 2 H), 3.04 (t, J=5.80 Hz, 2 H), 3.39-3.45 (m, 3 H), 3.51-3.62 (m, 6 H), 4.00-4.09 (m, 2 H), 4.50 (br. s., 2 H), 9.77 (br. s., 1 H).

General Procedure V for the Synthesis of Compounds 14a

To a mixture of aldehyde R$_3$CHO (1.0 equiv) and amine 13 (1.0 equiv) in DMF:THF (1:8) was added sodium triacetoxyborohydride (1.5 equiv). The reaction mixture was stirred at RT for 12 h and then diluted with EtOAc. H$_2$O was added and the layers were separated. The organic layer was washed with saturated Na$_2$CO$_3$, H$_2$O and brine, dried over anhydrous Na$_2$SO$_4$, filtered and concentrated in vacuo. The residue obtained was purified by silica gel chromatgraphy (0-15% MeOH in DCM) to afford the respective products.

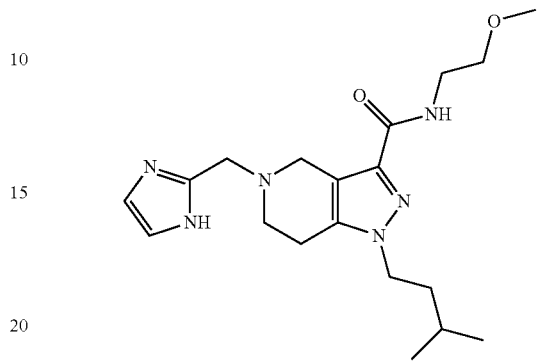

5-((1H-imidazol-2-yl)methyl)-1-isopentyl-N-(2-methoxyethyl)-4,5,6,7-tetrahydro-1H-pyrazolo(4,3-c)pyridine-3-carboxamide (14a NUCC-0000398): Prepared according to General procedure V using amine 13 (60 mg, 0.19 mmol) to afford 14a or NUCC-0000398 (15 mg, 21%) as yellow waxy solid. MS (ESI): mass calcd. for $C_{19}H_{30}N_6C_2$, 374.24; m/z found, 375.76 (M+H)+; $^1$H NMR (500 MHz, CDCl$_3$) δ 0.97 (s, 3 H), 0.98 (s, 3 H), 1.62 (dt, J=13.35, 6.60 Hz, 1 H), 1.68-1.75 (m, 2 H), 2.73 (t, J=5.65 Hz, 2 H), 2.86 (t, J=5.80 Hz, 2 H), 3.41 (s, 3 H), 3.54-3.57 (m, 2 H), 3.57-3.62 (m, 2 H), 3.95 (s, 4 H), 3.97-4.01 (m, 2 H), 7.03 (s, 2 H), 7.11 (t, J=5.49 Hz, 1 H); $^{13}$C NMR (126 MHz, CDCl$_3$) δ 15.43, 21.71, 22.51, 25.83, 38.70, 38.89, 48.04, 48.92, 50.11, 54.16, 58.96, 71.54, 115.73, 137.40, 140.41, 144.85, 162.87.

General Synthetic Scheme C.

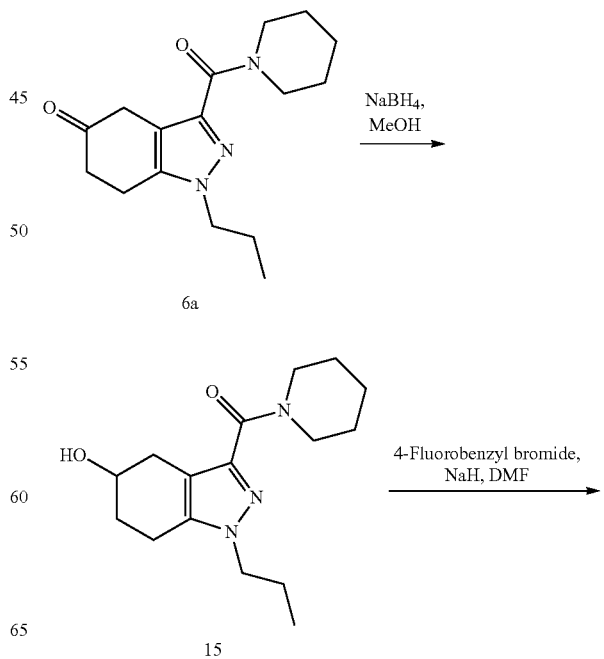

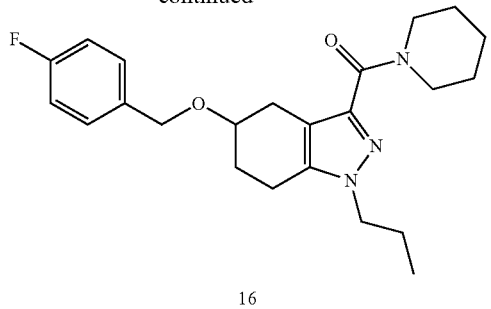

16

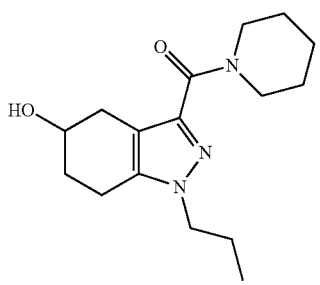 [SMILES: CCCn1nc(C(=O)N2CCCCC2)c2c1CCC(O)C2]

(5-hydroxy-1-propyl-4,5,6,7-tetrahydro-1H-indazol-3-yl)(piperidin-1-yl)methanone (15). A solution of 3-(piperidine-1-carbonyl)-1-propyl-6,7-dihydro-1H-indazol-5(4H)-one (6a, 120 mg, 0.415 mmol) in MeOH (Volume: 1.5 ml) was cooled to 0C. NaBH4 (15.69 mg, 0.415 mmol) was added in portions and the mixture was stirred at 0C. for 1 h. The solvent was evaporated, EtOAc and sat. NH4Cl were added. The organic layer was separated, dried over anhydrous Na2SO4 and evaporated to give the product which was used without additional purification (80mg, 66%). MS (ESI): mass calcd. for $C_{16}H_{25}N_3O_2$, 291.19; m/z found, 292.32 (M+H)+.

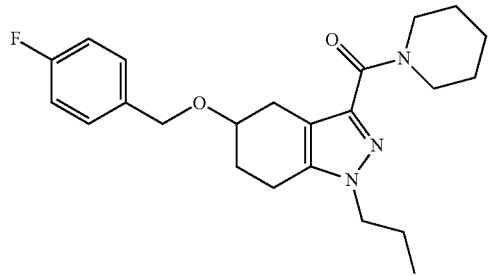 [SMILES: CCCn1nc(C(=O)N2CCCCC2)c2c1CCC(OCc1ccc(F)cc1)C2]

(5-((4-fluorobenzyl)oxy)-1-propyl-4,5,6,7-tetrahydro-1H-indazol-3-yl)(piperidin-1-yl)methanone (16). NaH (7.41 mg, 0.309 mmol) was added to a cooled solution of (5-hydroxy-1-propyl-4,5,6,7-tetrahydro-1H-indazol-3 -yl)(piperidin-1-yl)methanone (60 mg, 0.206 mmol) in DMF (Volume: 1 ml). 1-(Bromomethyl)-4-fluorobenzene (0.028 ml, 0.227 mmol) was then added and the mixture heated to 80C. for 12 h. EtOAc and water were added and the layers separated. The organic extract was washed with brine, dried over anhydrous Na2SO4, filtered and concentrated under redcued pressure. The residue obtained was purified by reversed phase chromatography using ACN/water to afford the product (24.4 mg, 30%). MS (ESI): mass calcd. for $C_{23}H_{30}FN_3O_2$, 399.23; m/z found, 400.52 (M+H)+; $^1$H NMR (500 MHz, CDCl$_3$) δ 0.91 (t, J=7.32 Hz, 3 H) 1.60-1.74 (m, 6 H) 1.81 (sxt, J=7.32 Hz, 2 H) 1.99-2.04 (m, 2 H) 2.54-2.62 (m, 1 H) 2.69-2.79 (m, 2 H) 3.08 (dd, J=16.02, 4.73 Hz, 1 H) 3.64-3.72 (m, 2 H) 3.77-3.85 (m, 3 H) 3.91 (dd, J=7.63, 6.71 Hz, 2 H) 4.52 (d, J=11.90 Hz, 1 H) 4.61 (d, J=11.90 Hz, 1 H) 6.97-7.05 (m, 2 H) 7.27-7.33 (m, 2 H).

Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

REFERENCES

The following references, some of which are cited above by their number/letter, are herein incorporated by reference in their entireties.

(1) (a) Lu, M.; Grove, E. A.; Miller, R. J., Abnormal development of the hippocampal dentate gyrus in mice lacking the CXCR4 chemokine receptor. *Proc Natl Acad Sci USA* 2002, 99 (10), 7090-5; (b) Li, M.; Ransohoff, R. M., Multiple roles of chemokine CXCL12 in the central nervous system: a migration from immunology to neurobiology. *Progress in neurobiology* 2008, 84 (2), 116-31; (c) Mithal, D. S.; Banisadr, G.; Miller, R. J., CXCL12

Signaling in the Development of the Nervous System. *Journal of neuroimmune pharmacology: the official journal of the Society on NeuroImmune Pharmacology* 2012.

(2) (a) Liang, Z.; Zhan, W.; Zhu, A.; Yoon, Y.; Lin, S.; Sasaki, M.; Klapproth, J. M.; Yang, H.; Grossniklaus, H. E.; Xu, J.; Rojas, M.; Voll, R. J.; Goodman, M. M.; Arrendale, R. F.;

Liu, J.; Yun, C. C.; Snyder, J. P.; Liotta, D. C.; Shim, H., Development of a unique small molecule modulator of CXCR4. *PloS one* 2012, 7 (4), e34038; (b) Beider, K.; Begin, M.; Abraham, M.; Wald, H.; Weiss, I. D.; Wald, O.; Pikarsky, E.; Zeira, E.; Eizenberg, O.; Galun, E.; Hardan, I.; Engelhard, D.; Nagler, A.; Peled, A., CXCR4 antagonist 4F-benzoyl-TN14003 inhibits leukemia and multiple myeloma tumor growth. *Experimental hematology* 2011, 39 (3), 282-92; (c) Bridger, G. J.; Skerlj, R. T.; Hernandez-Abad, P. E.; Bogucki, D. E.; Wang, Z.; Zhou, Y.; Nan, S.; Boehringer, E. M.; Wilson, T.; Crawford, J.; Metz, M.; Hatse, S.; Princen, K.; De Clercq, E.; Schols, D., Synthesis and structure-activity relationships of azamacrocyclic C-X-C chemokine receptor 4 antagonists: analogues containing a single azamacrocyclic ring are potent inhibitors of T-cell tropic (X4) HIV-1 replication. *Journal of medicinal chemistry* 2010, 53 (3), 1250-60; (d) Ueda, S.; Kato, M.; Inuki, S.; Ohno, H.; Evans, B.; Wang, Z. X.; Peiper, S. C.; Izumi, K.; Kodama, E.; Matsuoka, M.; Nagasawa, H.; Oishi, S.; Fujii, N., Identification of novel non peptide CXCR4 antagonists by ligand-based design approach. *Bioorganic & medicinal chemistry letters* 2008, 18 (14), 4124-9; (e) Skerlj, R.; Bridger, G.; McEachern, E.; Harwig, C.; Smith, C.; Wilson, T.; Veale, D.; Yee, H.; Crawford, J.; Skupinska, K.; Wauthy, R.; Yang, W.; Zhu, Y.; Bogucki, D.; Di Fluri, M.; Langille, J.; Huskens, D.; De Clercq, E.; Schols, D., Synthesis and SAR of novel CXCR4 antagonists that are potent inhibitors of T tropic (X4) HIV-1 replication. *Bioorganic & medicinal chemistry letters* 2011, 21 (1), 262-6; (f) Thoma, G.; Streiff, M. B.; Kovarik, J.;

Glickman, F.; Wagner, T.; Beerli, C.; Zerwes, H. G., Orally bioavailable isothioureas block function of the chemokine receptor CXCR4 in vitro and in vivo. *Journal of medicinal chemistry* 2008, 51 (24), 7915-20.
(3) (a) Zhou, N.; Luo, Z.; Luo, J.; Liu, D.; Hall, J. W.; Pomerantz, R. J.; Huang, Z., Structural and functional characterization of human CXCR4 as a chemokine receptor and HIV-1 co-receptor by mutagenesis and molecular modeling studies. *J Biol Chem* 2001, 276 (46), 42826-33; (b) Wong, R. S.; Bodart, V.; Metz, M.; Labrecque, J.; Bridger, G.; Fricker, S. P., Comparison of the potential multiple binding modes of bicyclam, monocylam, and noncyclam small-molecule CXC chemokine receptor 4 inhibitors. *Mol. Pharmacol.* 2008, 74 (6), 1485-95; (c) Neves, M. A.; Simoes, S.; Sa e Melo, M. L., Ligand-guided optimization of CXCR4 homology models for virtual screening using a multiple chemotype approach. *J Comput Aided Mol Des* 2010, 24 (12), 1023-33; (d) Perez—Nueno, V. I.; Pettersson, S.; Ritchie, D. W.; Borrell, J. I.; Teixido, J., Discovery of novel HIV entry inhibitors for the CXCR4 receptor by prospective virtual screening. *Journal of chemical information and modeling* 2009, 49 (4), 810-23; (e) Perez—Nueno, V. I.; Ritchie, D. W.; Rabal, O.; Pascual, R.; Borrell, J. I.; Teixido, J., Comparison of ligand based and receptor-based virtual screening of HIV entry inhibitors for the CXCR4 and CCR5 receptors using 3D ligand shape matching and ligand-receptor docking. *Journal of chemical information and modeling* 2008, 48 (3), 509-33; (0 Singh, S.; Malik, B. K.; Sharma, D. K., Targeting HIV-1 through molecular modeling and docking studies of CXCR4: leads for therapeutic development. *Chemical biology & drug design* 2007, 69 (3), 191-203; (g) Vabeno, J.; Nikiforovich, G. V.; Marshall, G. R., Insight into the binding mode for cyclopentapeptide antagonists of the CXCR4 receptor. *Chemical biology & drug design* 2006, 67 (5), 346-54; (h) Carter, P. H.; Tebben, A. J., Chapter 12. The use of receptor homology modeling to facilitate the design of selective chemokine receptor antagonists. *Methods in enzymology* 2009, 461, 249-79.
(4) Wu, B.; Chien, E. Y.; Mol, C. D.; Fenalti, G.; Liu, W.; Katritch, V.; Abagyan, R.; Brooun, A.; Wells, P.; Bi, F. C.; Hamel, D. J.; Kuhn, P.; Handel, T. M.; Cherezov, V.; Stevens, R. C., Structures of the CXCR4 chemokine GPCR with small-molecule and cyclic peptide antagonists. *Science* 2010, 330 (6007), 1066-71.
(5) (a) Tian, S.; Choi, W. T.; Liu, D.; Pesavento, J.; Wang, Y.; An, J.; Sodroski, J. G.; Huang, Z., Distinct functional sites for human immunodeficiency virus type 1 and stromal cell-derived factor 1alpha on CXCR4 transmembrane helical domains. *Journal of virology* 2005, 79 (20), 12667-73; (b) Brelot, A.; Heveker, N.; Montes, M.; Alizon, M., Identification of residues of CXCR4 critical for human immunodeficiency virus coreceptor and chemokine receptor activities. *J. Biol. Chem.* 2000, 275 (31), 23736-44; (c) Zhong, C.; Ding, J., New G-protein-coupled receptor structures provide insights into the recognition of CXCL12 and HIV-1 gp120 by CXCR4. *Acta biochimica et biophysica Sinica* 2011, 43 (5), 337-8.
(6) Mysinger, M. M.; Weiss, D. R.; Ziarek, J. J.; Gravel, S.; Doak, A. K.; Karpiak, J.; Heveker, N.; Shoichet, B. K.; Volkman, B. F., Structure-based ligand discovery for the protein-protein interface of chemokine receptor CXCR4. *Proc. Nat. Acad. Sci.* 2012, 109 (14), 5517-22.
(7) (a) *Common feature pharmacophore generation (Hip-Hop). Discovery Studio* 3.1, Accelrys Inc.: 2011; (b) Accelrys Software Inc., D. S. M. E., Release 4.1 *Discovery Studio. Accelrys Software Inc.,* 2012., 2012.
(8) (a) International, T. 2011-2014 Certara, L.P.210 N Tucker Blvd, Suite 350, St. Louis Mo. 63101, 2011; (b) Jain, A. N., Surflex: fully automatic flexible molecular docking using a molecular similarity-based search engine. *Journal of medicinal chemistry* 2003, 46 (4), 499-511.
(9) Schrodinger LLC, N. *Small-Molecule Drug Discovery Suite* 2014-4: *Glide, version* 6.5, Schrödinger, LLC, New York, N.Y., 2014., 2014.
(10) Cross, J. B.; Thompson, D. C.; Rai, B. K.; Baber, J. C.; Fan, K. Y.; Hu, Y.; Humblet, C., Comparison of several molecular docking programs: pose prediction and virtual screening accuracy. *Journal of chemical information and modeling* 2009, 49 (6), 1455-74.
(11) Schrodinger, P. *Schrödinger Release* 2014-4: *Prime, version* 3.8, Schrödinger, LLC, New York, N.Y., 2014., 3.8.
(12) (a) Busillo, J. M.; Benovic, J. L., Regulation of CXCR4 signaling. *Biochimica et biophysica acta* 2007, 1768 (4), 952-63; (b) Tran, P. B.; Ren, D.; Miller, R. J., The HIV-1 coat protein gp120 regulates CXCR4-mediated signaling in neural progenitor cells. Journal of neuroimmunology 2005, 160 (1-2), 68-76.
(13) (a) Haribabu, B.; Richardson, R. M.; Fisher, I.; Sozzani, S.; Peiper, S. C.; Horuk, R.; Ali, H.; Snyderman, R., Regulation of human chemokine receptors CXCR4. Role of phosphorylation in desensitization and internalization. *J Biol Chem* 1997, 272 (45), 28726-31; (b) Roland, J.; Murphy, B. J.; Ahr, B.; Robert-Hebmann, V.; Delauzun, V.; Nye, K. E.; Devaux, C.; Biard-Piechaczyk, M., Role of the intracellular domains of CXCR4 in SDF-1-mediated signaling. *Blood* 2003, 101 (2), 399-406.
(14) Han, X., Constitutively active chemokine CXC receptors. *Adv Pharmacol* 2014, 70, 265-301.
(15) (a) Guyon, A.; Kussrow, A.; Olmsted, I. R.; Sandoz, G.; Bornhop, D. J.; Nahon, J. -L., Baclofen and other GABAB receptor agents are allosteric modulators of the CXCL12 chemokine receptor CXCR4. *The Journal of neuroscience: the official journal of the Society for Neuroscience* 2013, 33 (28), 11643-54; (b) Quoyer, J.; Janz, J. M.; Luo, J.; Ren, Y.; Armando, S.; Lukashova, V.; Benovic, J. L.; Carlson, K. E.; Hunt, S. W., 3rd; Bouvier, M., Pepducin targeting the C-X-C chemokine receptor type 4 acts as a biased agonist favoring activation of the inhibitory G protein. *P Natl Acad Sci USA* 2013, 110 (52), E5088-97; (c) Zhang, W. -B.; Navenot, J. -M.; Haribabu, B.; Tamamura, H.; Hiramatu, K.; Omagari, A.; Pei, G.; Manfredi, J. P.; Fujii, N.; Broach, J. R.; Peiper, S. C., A point mutation that confers constitutive activity to CXCR4 reveals that T140 is an inverse agonist and that AMD3100 and ALX40-4C are weak partial agonists. *The Journal of biological chemistry* 2002, 277 (27), 24515-21.
(16) Choi, W. T.; Tian, S.; Dong, C. Z.; Kumar, S.; Liu, D.; Madani, N.; An, J.; Sodroski, J. G.; Huang, Z., Unique ligand binding sites on CXCR4 probed by a chemical biology approach: implications for the design of selective human immunodeficiency virus type 1 inhibitors. *Journal of virology* 2005, 79 (24), 15398-404.
(17) Urbano, M.; Guerrero, M.; Rosen, H.; Roberts, E., Modulators of the Sphingosine 1-phosphate receptor 1. *Bioorganic & medicinal chemistry letters* 2013, 23 (23), 6377-89.
(18) Bodner, A.; Toth, P. T.; Oh, S. B.; Lu, M.; Tran, P. B.; Chin, R. K.; Ren, D.; Miller, R. J., CD4 dependence of gp120IIIB-CXCR4 interaction is cell-type specific. *Journal of neuroimmunology* 2003, 140 (1-2), 1-12.

The invention claimed is:
1. A composition comprising a compound or Formula (1):

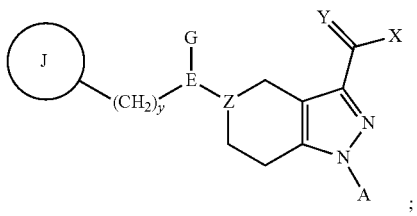

wherein Z is C;
wherein E is C, S, N, O, or absent; when E is absent Z and $(CH_2)_y$ are directly linked by a single covalent bond;
wherein G is $CH_3$, CN, halogen (e.g., Cl, Br, F, etc.), trihalomethane (e.g., $CCl_3$, $CBr_3$, $CF_3$, etc.), OH, $NH_2$, $alkyl_{1-6}$-$CH_3$, $alkyl_{1-6}$-CN, $alkyl_{1-6}$-halogen (e.g., Cl, Br, F, etc.), $alkyl_{1-6}$-trihalomethane (e.g., $CCl_3$, $CBr_3$, $CF_3$, etc.), $alkyl_{1-6}$-OH, or $alkyl_{1-6}$-$NH_2$;
wherein y is 0-6;
wherein

is any carbocycle, heterocycle, aryl, heteroaryl, or multi-ring systems thereof, and

is optionally substituted at any suitable positions with $CH_3$, CN, halogen (e.g., Cl, Br, F, etc.), trihalomethane (e.g., $CCl_3$, $CBr_3$, $CF_3$, etc.), OH, $NH_2$, $alkyl_{1-6}$-$CH_3$, $alkyl_{1-6}$-CN, $alkyl_{1-6}$-halogen (e.g., Cl, Br, F, etc.), $alkyl_{1-6}$-trihalomethane (e.g., $CCl_3$, $CBr_3$, $CF_3$, etc.), $alkyl_{1-6}$-OH, or $alkyl_{1-6}$-$NH_2$;
wherein A is $CH_3$, CN, halogen (e.g., Cl, Br, F, etc.), trihalomethane (e.g., $CCl_3$, $CBr_3$, $CF_3$, etc.), OH, $NH_2$, $alkyl_{1-6}$-$CH_3$, $alkyl_{1-6}$-CN, $alkyl_{1-6}$-halogen (e.g., Cl, Br, F, etc.), $alkyl_{1-6}$-trihalomethane (e.g., $CCl_3$, $CBr_3$, $CF_3$, etc.), $alkyl_{1-6}$-OH, $alkyl_{1-6}$-$NH_2$, a carbocycle, a heterocycle, an aryl, a heteroaryl, a multi-ring system thereof, or absent;
wherein Y is C, S, O, or absent;
wherein X is:

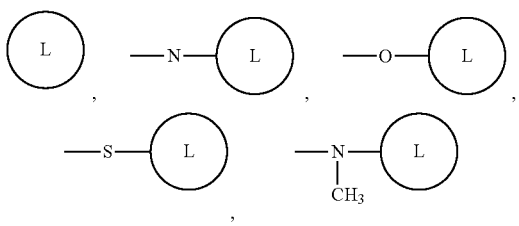

$NH$-$alkyl_{1-6}$, $O$-$alkyl_{1-6}$, $S$-$alkyl_{1-6}$, $CH_2$-$alkyl_{1-6}$, $NH$-$alkyl_{1-6}$-$O$-methyl, $O$-$alkyl_{1-6}$-$O$-methyl, $S$-$alkyl_{1-6}$-$O$-methyl, $CH_2$-$alkyl_{1-6}$-$O$-methyl, and N-dimethyl;
wherein if Y is absent, X is not O-methyl;
wherein

is any carbocycle, heterocycle, aryl, heteroaryl, or multi-ring systems thereof, and

is optionally substituted at any suitable positions with $CH_3$, CN, halogen (e.g., Cl, Br, F, etc.), trihalomethane (e.g., $CCl_3$, $CBr_3$, $CF_3$, etc.), OH, $NH_2$, $alkyl_{1-6}$-$CH_3$, $alkyl_{1-6}$-CN, $alkyl_{1-6}$-halogen (e.g., Cl, Br, F, etc.), $alkyl_{1-6}$-trihalomethane (e.g., $CCl_3$, $CBr_3$, $CF_3$, etc.), $alkyl_{1-6}$-OH, or $alkyl_{1-6}$-$NH_2$; or
a pharmaceutically acceptable salt therof.
2. The composition of claim 1, wherein the compound binds to CXCR4.
3. The composition of claim 1, wherein the compound is a modulator of CXCR4 activity.
4. The composition of claim 3, wherein the compound is a CXCR4 agonist.
5. The composition of claim 3, wherein the compound is a CXCR4 antagonist.
6. The composition of claim 1, wherein the compound is selected from:

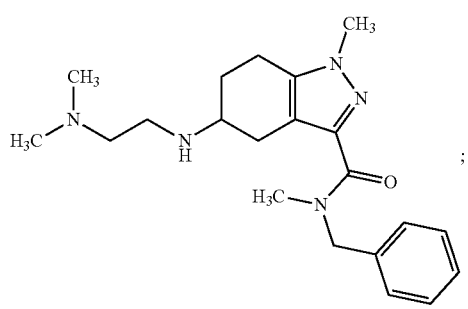

NUCC-0000388

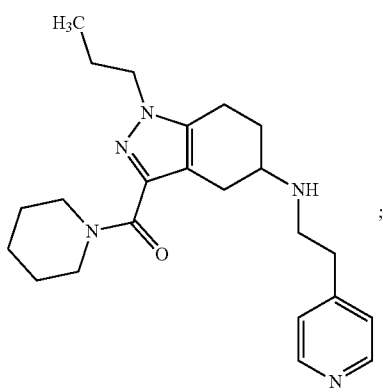

NUCC-0000390

91
-continued
NUCC-000400
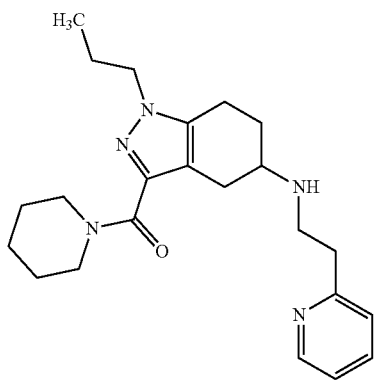
NUCC-0054118
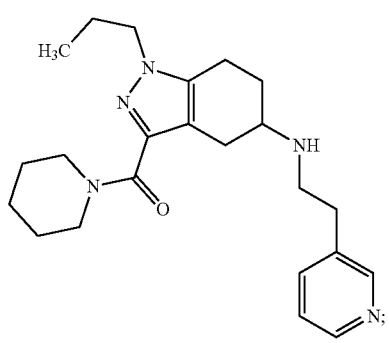
NUCC-0054119
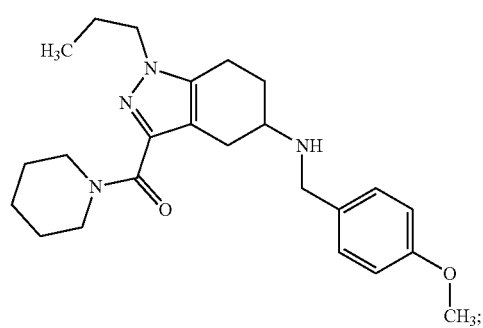
NUCC-0054120
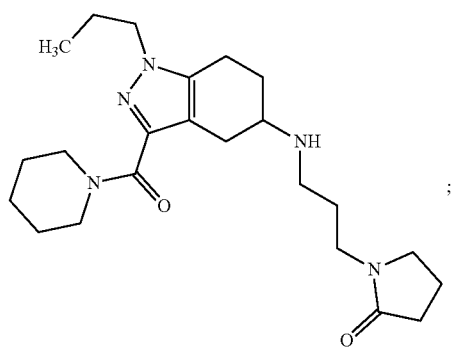
92
-continued
NUCC-0054121
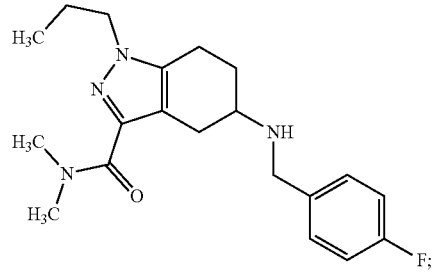
NUCC-0054122
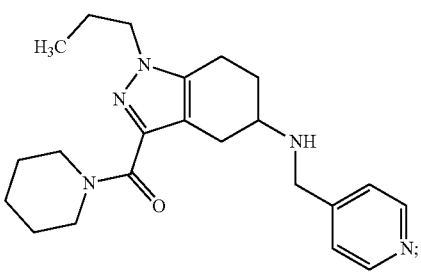
NUCC-0054123
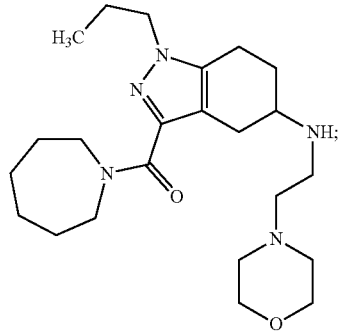
NUCC-0054124
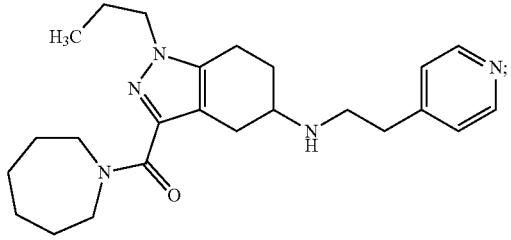
NUCC-0054125
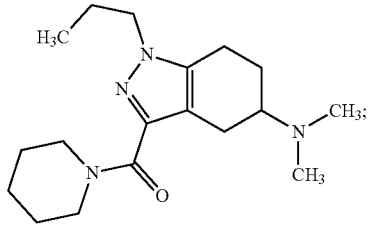

NUCC-0054126
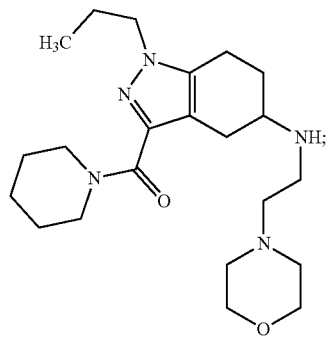
NUCC-0054127
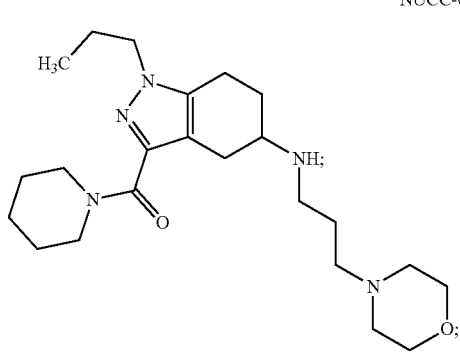
NUCC-0054128
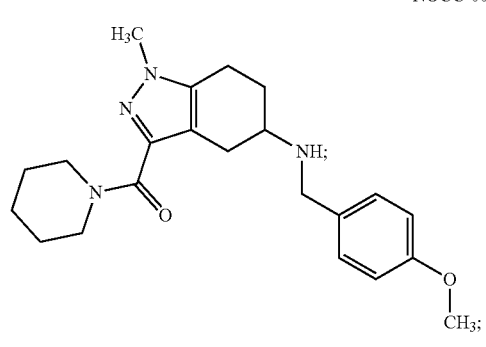
NUCC-0054129
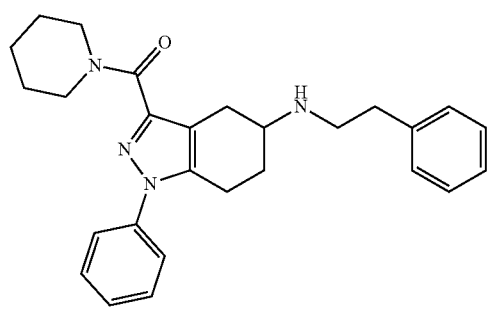
NUCC-0176286
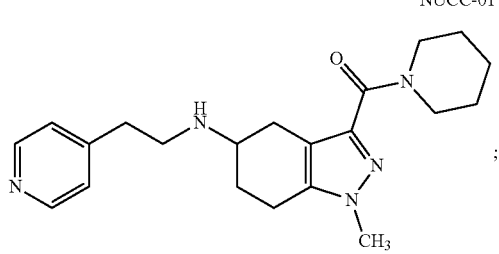
NUCC-0176287
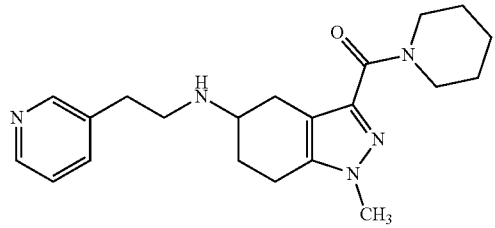
NUCC-0176288
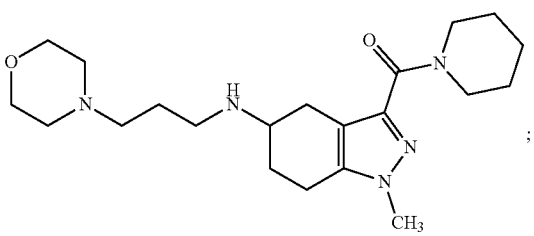
NUCC-0176289
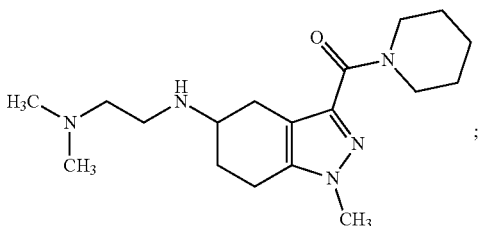
NUCC-0176290
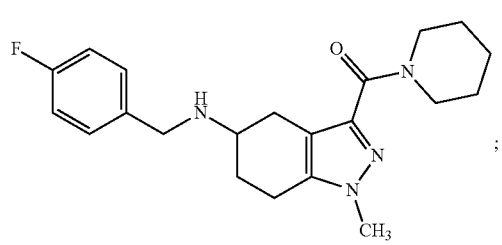
NUCC-0176291
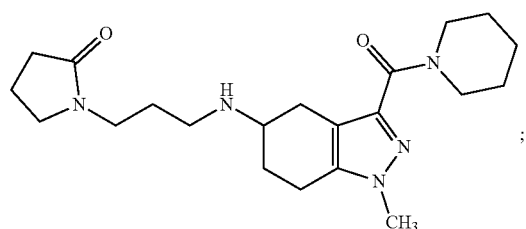
NUCC-0176292
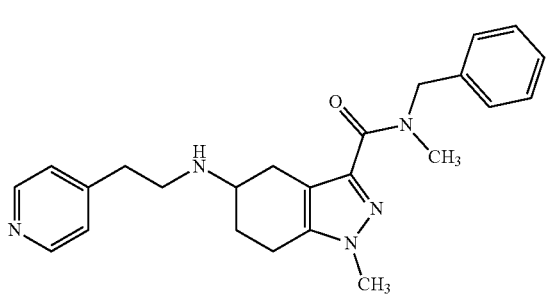

NUCC-0176293
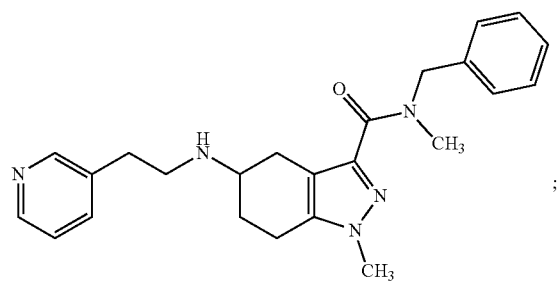
NUCC-0176294
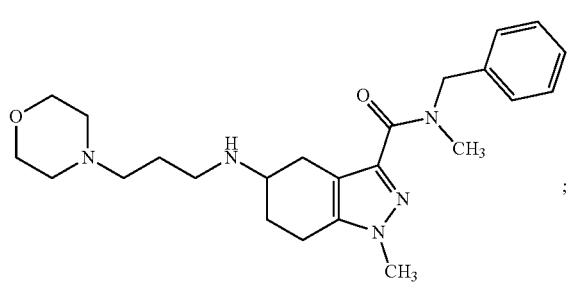
NUCC-017295
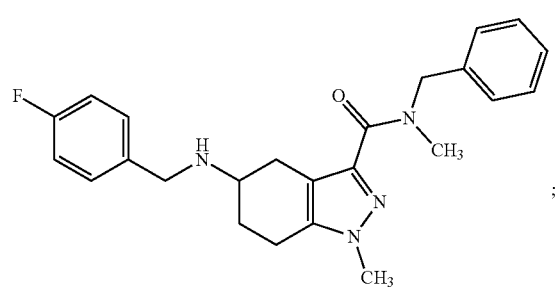
NUCC-0176296
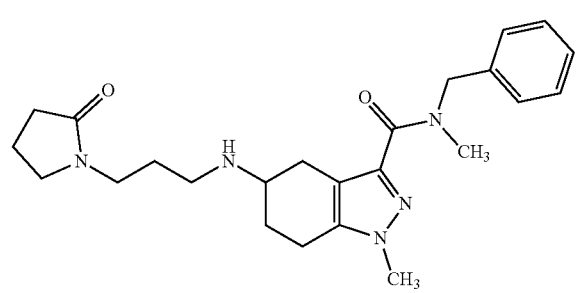
NUCC-0176297
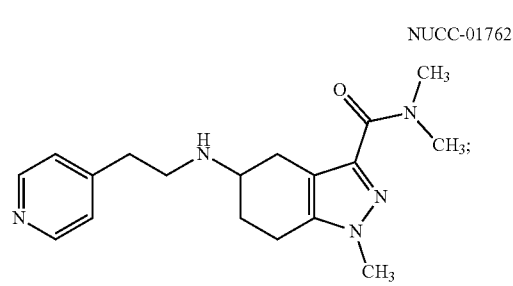
NUCC-0176298
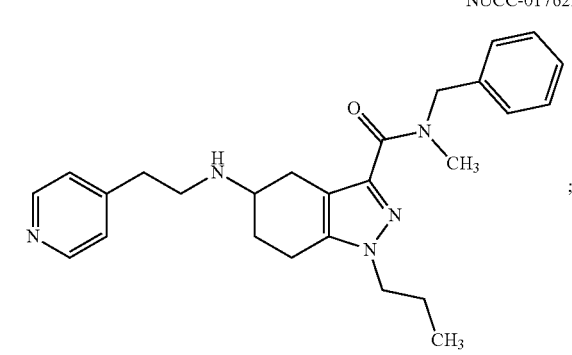
NUCC-0176299
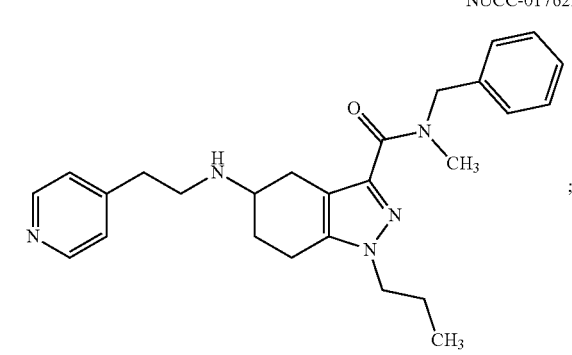
NUCC-0176300
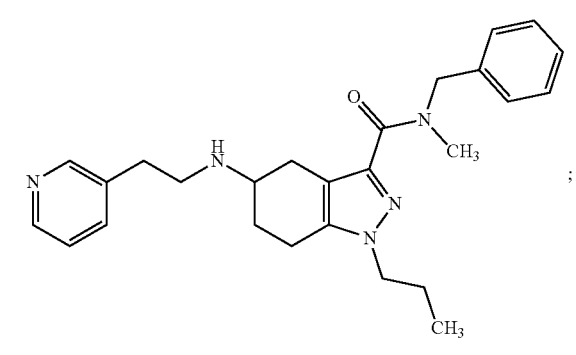
NUCC-0176301
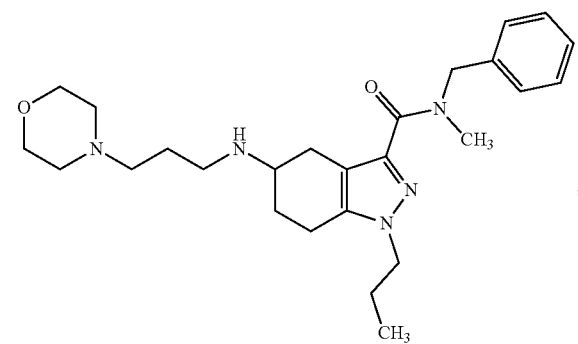

NUCC-0176302

NUCC-0176303

NUCC-0176304

NUCC-0176305

NUCC-0176306

NUCC-0176307

NUCC-0176308

NUCC-0176309

NUCC-0176310

NUCC-0176311
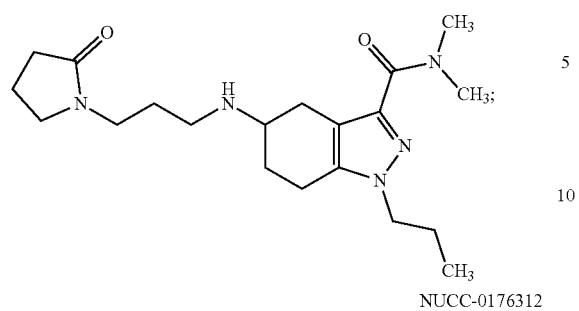
NUCC-0176312
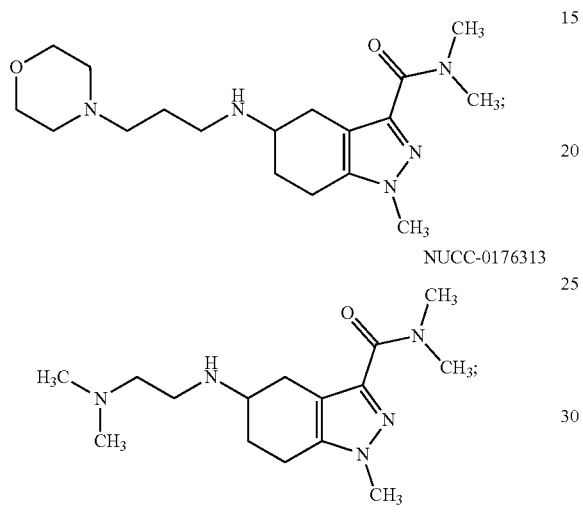
NUCC-0176313
NUCC-0176314
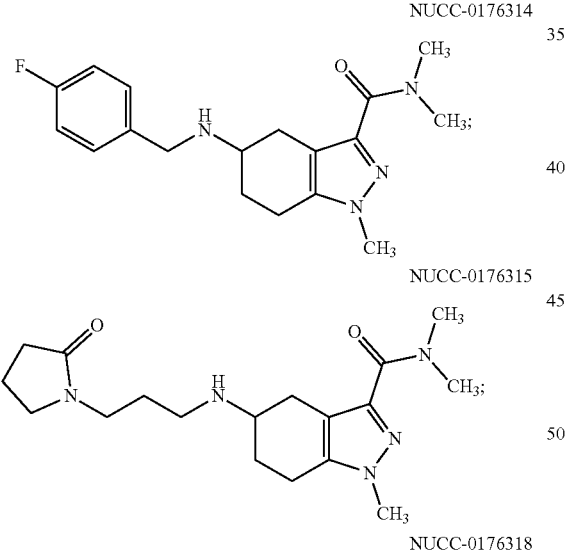
NUCC-0176315
NUCC-0176318
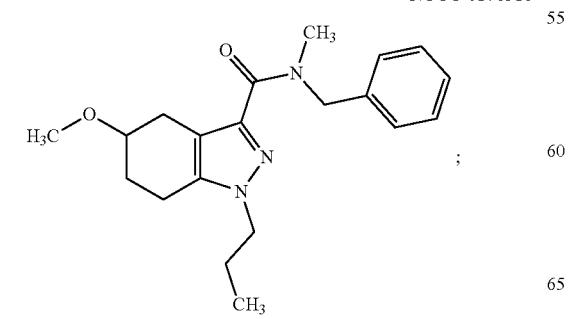
NUCC-0196323
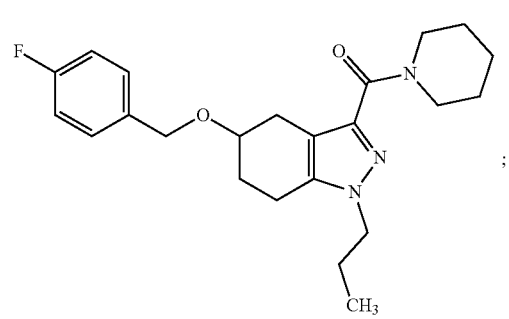
NUCC-0196324
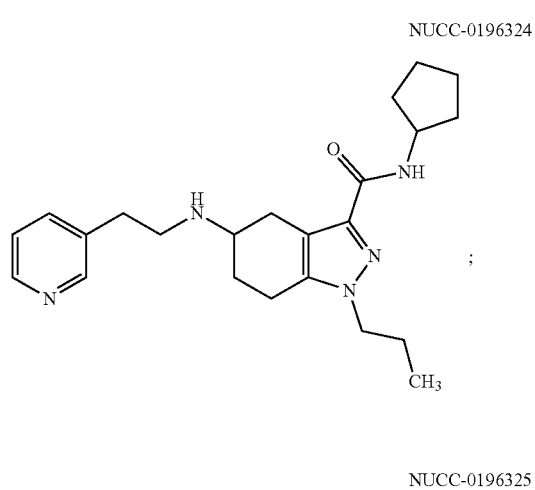
NUCC-0196325
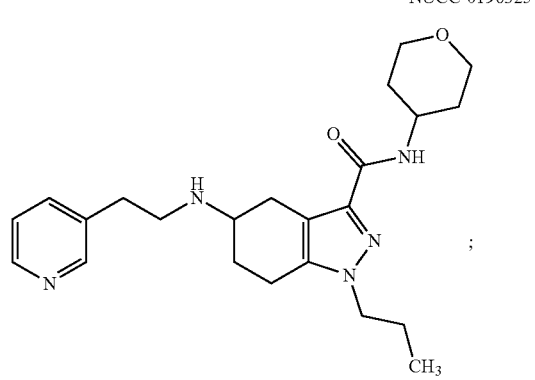
NUCC-0196326
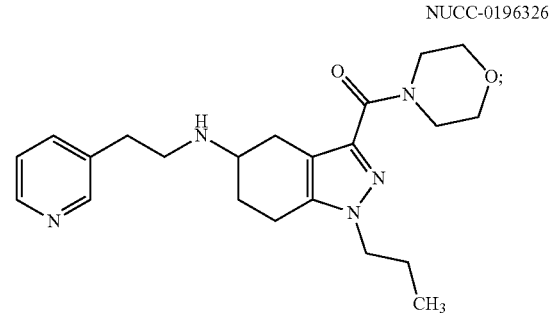

-continued
NUCC-0196327
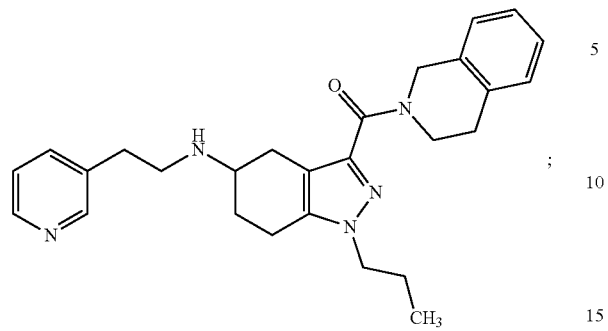
NUCC-0196328
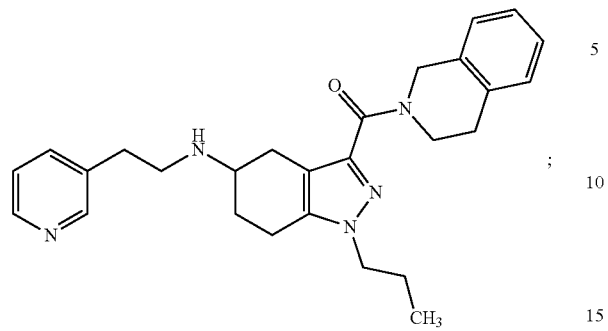
NUCC-0196329
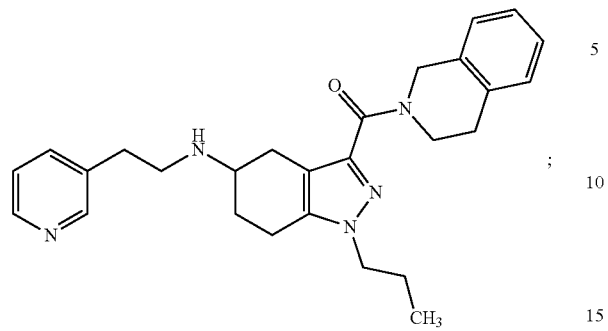
NUCC-0196330
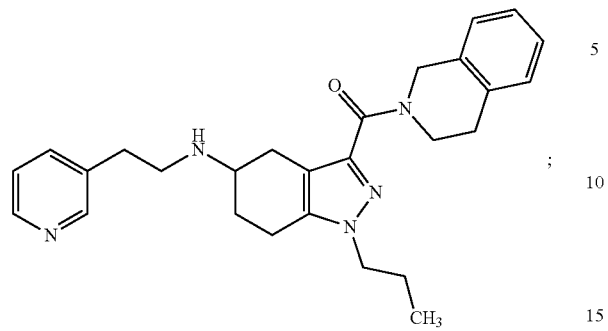
-continued
NUCC-0196331
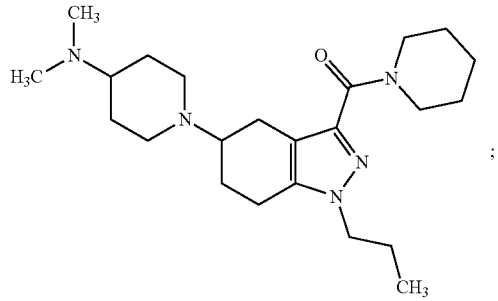
NUCC-0196332
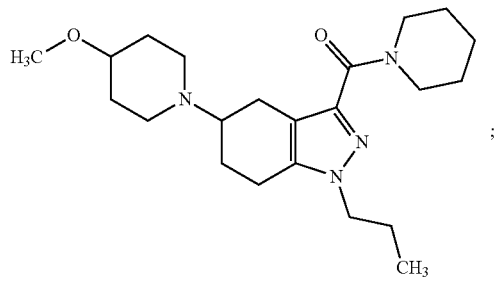
NUCC-0196333
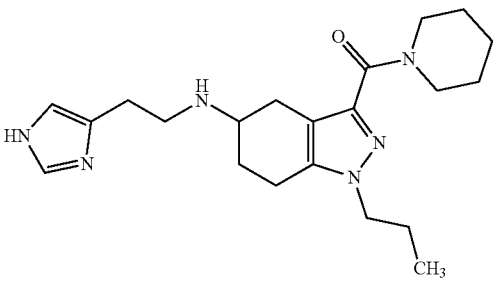
NUCC-0196334
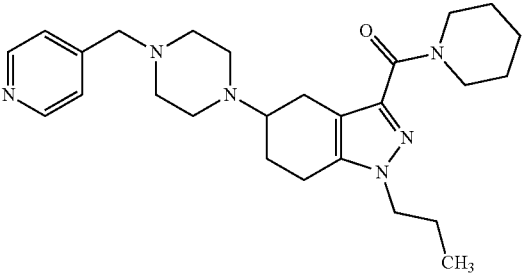
NUCC-0196335
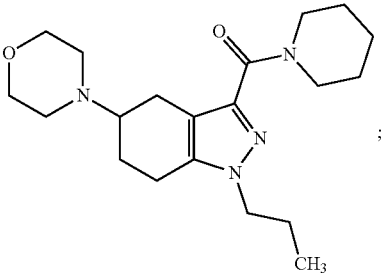

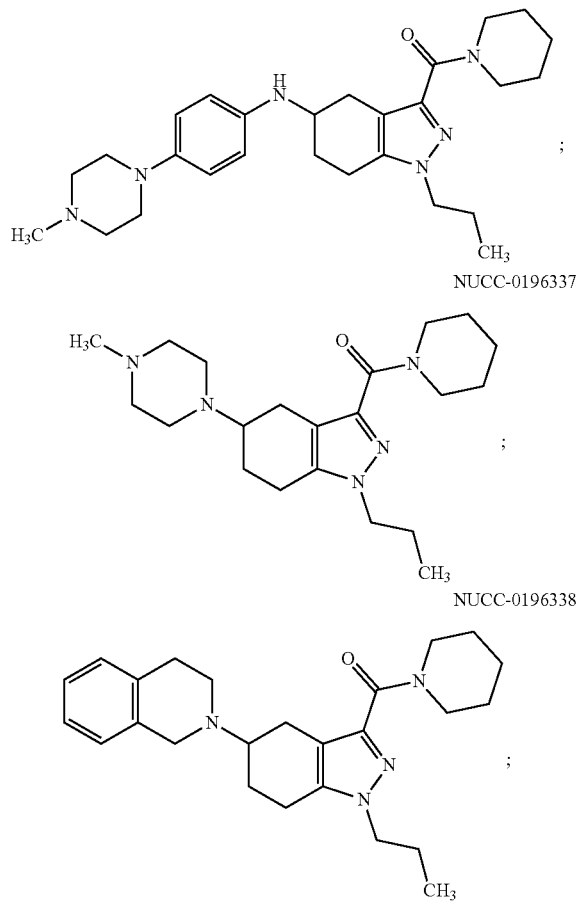

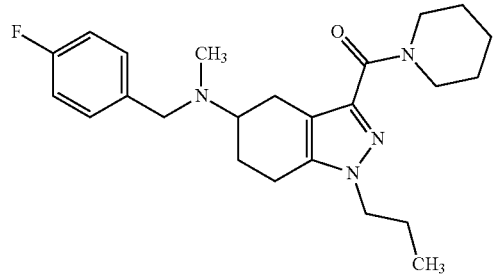

7. The composition of claim 6, wherein the compound is selected from the group consisting of: NUCC-0176286, NUCC-0176287, NUCC-0176288, NUCC-0176289, NUCC-0176290, NUCC-0176291, NUCC-0176292, NUCC-0176293, NUCC-0176294, NUCC-0176295, NUCC-0176296, NUCC-0176297, NUCC-0176298, NUCC-0176299, NUCC-0176300, NUCC-0176301, NUCC-0176302, NUCC-0176303, NUCC-0176304, NUCC-0176305, NUCC-0176306, NUCC-0176307, NUCC-0176308, NUCC-0176309, NUCC-0176310, NUCC-0176311, NUCC-0176312, NUCC-0176313, NUCC-0176314, NUCC-0176315, NUCC-0176318, NUCC-0196323, NUCC-0196324, NUCC-0196325, NUCC-0196326, NUCC-0196327, NUCC-0196328, NUCC-0196329, NUCC-0196330, NUCC-0196331, NUCC-0196332, NUCC-0196333, NUCC-0196334, NUCC-0196335, NUCC-0196336, NUCC-0196337, NUCC-0196338, and NUCC-0196339.

8. A method of modulating CXCR4 activity comprising contacting CXCR4 with a composition of claim 1.

* * * * *

UNITED STATES PATENT AND TRADEMARK OFFICE
CERTIFICATE OF CORRECTION

PATENT NO. : 10,435,375 B2  
APPLICATION NO. : 15/571721  
DATED : October 8, 2019  
INVENTOR(S) : Gary E. Schiltz, Richard J. Miller and Rama K. Mishra Page 1 of 1

It is certified that error appears in the above-identified patent and that said Letters Patent is hereby corrected as shown below:

In the Claims

Claim 6, Column 101, Line 20 to 35, Compound NUCC-0196328 should be corrected to read:

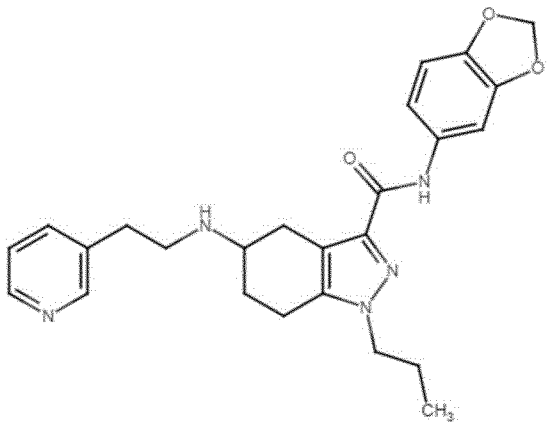

Signed and Sealed this  
Tenth Day of January, 2023

Katherine Kelly Vidal  
*Director of the United States Patent and Trademark Office*